United States Patent
Damiano et al.

(10) Patent No.: US 9,005,614 B2
(45) Date of Patent: Apr. 14, 2015

(54) PRLR-SPECIFIC ANTIBODY AND USES THEREOF

(75) Inventors: Jason Damiano, Moraga, CA (US); Mohammad Luqman, Emeryville, CA (US); Daniel Bedinger, Berkeley, CA (US); Linda Masat, Walnut Creek, CA (US); Amer Mirza, San Francisco, CA (US); Genevieve Nonet, Berkeley, CA (US)

(73) Assignees: Novartis AG, Basel (CH); Xoma Technology Ltd., Berkeley, CA (US)

( * ) Notice: Subject to any disclaimer, the term of this patent is extended or adjusted under 35 U.S.C. 154(b) by 1179 days.

(21) Appl. No.: 12/951,744

(22) Filed: Nov. 22, 2010

(65) Prior Publication Data

US 2011/0150760 A1 Jun. 23, 2011

Related U.S. Application Data

(62) Division of application No. 11/840,267, filed on Aug. 17, 2007, now Pat. No. 7,867,493.

(60) Provisional application No. 60/946,360, filed on Jun. 26, 2007, provisional application No. 60/838,648, filed on Aug. 18, 2006.

(51) Int. Cl.
*A61K 51/10* (2006.01)
*A61K 39/395* (2006.01)
*C07K 16/28* (2006.01)
*A61K 45/06* (2006.01)
*A61K 39/00* (2006.01)

(52) U.S. Cl.
CPC ......... *C07K 16/2869* (2013.01); *A61K 39/3955* (2013.01); *A61K 45/06* (2013.01); *A61K 2039/505* (2013.01); *C07K 2316/96* (2013.01); *C07K 2317/21* (2013.01); *C07K 2317/24* (2013.01); *C07K 2317/56* (2013.01); *C07K 2317/565* (2013.01); *C07K 2317/622* (2013.01); *C07K 2317/732* (2013.01); *C07K 2317/92* (2013.01); *C07K 2319/00* (2013.01); *C07K 2317/34* (2013.01); *C07K 2317/52* (2013.01)

(58) Field of Classification Search
USPC ............. 435/7.1, 85; 530/387.3, 389.1, 391.7
See application file for complete search history.

(56) References Cited

U.S. PATENT DOCUMENTS

| | | | |
|---|---|---|---|
| 30,985 A | 12/1860 | Pye | |
| 3,773,919 A | 11/1973 | Boswell et al. | |
| 4,179,337 A | 12/1979 | Davis et al. | |
| 4,301,144 A | 11/1981 | Iwashita et al. | |
| 4,419,446 A | 12/1983 | Howley et al. | |
| 4,485,045 A | 11/1984 | Regen | |
| 4,495,285 A | 1/1985 | Shimizu et al. | |
| 4,496,689 A | 1/1985 | Mitra | |
| 4,544,545 A | 10/1985 | Ryan et al. | |
| 4,560,655 A | 12/1985 | Baker | |
| 4,601,978 A | 7/1986 | Karin | |
| 4,609,546 A | 9/1986 | Hiratani | |
| 4,640,835 A | 2/1987 | Shimizu et al. | |
| 4,657,866 A | 4/1987 | Kumar | |
| 4,670,417 A | 6/1987 | Iwasaki et al. | |
| 4,675,187 A | 6/1987 | Konishi et al. | |
| 4,766,106 A | 8/1988 | Katre et al. | |
| 4,767,704 A | 8/1988 | Cleveland et al. | |
| 4,791,192 A | 12/1988 | Nakagawa et al. | |
| 4,816,567 A | 3/1989 | Cabilly et al. | |
| 4,892,538 A | 1/1990 | Aebischer et al. | |
| 4,927,762 A | 5/1990 | Darfler | |
| 4,965,199 A | 10/1990 | Capon et al. | |
| 4,975,278 A | 12/1990 | Senter et al. | |
| 5,013,556 A | 5/1991 | Woodle et al. | |
| 5,057,313 A | 10/1991 | Shih et al. | |
| 5,122,469 A | 6/1992 | Mather et al. | |
| 5,229,275 A | 7/1993 | Goroff | |
| 5,283,187 A | 2/1994 | Aebischer et al. | |
| 5,443,953 A | 8/1995 | Hansen et al. | |
| 5,530,101 A | 6/1996 | Queen et al. | |
| 5,545,807 A | 8/1996 | Surani et al. | |
| 5,565,332 A | 10/1996 | Hoogenboom et al. | |
| 5,567,610 A | 10/1996 | Borrebaeck et al. | |
| 5,573,905 A | 11/1996 | Lerner et al. | |
| 5,585,089 A | 12/1996 | Queen et al. | |
| 5,589,369 A | 12/1996 | Seidman et al. | |
| 5,591,669 A | 1/1997 | Krimpenfort et al. | |
| 5,693,762 A | 12/1997 | Queen et al. | |
| 5,766,866 A | 6/1998 | Center et al. | |
| 5,766,886 A | 6/1998 | Studnicka et al. | |

(Continued)

FOREIGN PATENT DOCUMENTS

| | | |
|---|---|---|
| AU | 639241 | 6/1989 |
| EP | 023940 | 2/1981 |

(Continued)

OTHER PUBLICATIONS

McKay, et al., "Tolerance to Single, but Not Multiple, Amino Acid Replacements in Antibody $V_H$ CDR2," The Journal of Immunology, 156: 3285-3291 (1996).

Okamura, et al., "Characterization and Applications of Monoclonal Antibodies to the Prolactin Receptor," Endocrinology, 124: 2499-2508 (1989).

(Continued)

*Primary Examiner* — Lynn Bristol

(74) *Attorney, Agent, or Firm* — Marshall, Gerstein & Borun LLP

(57) ABSTRACT

PRLR-specific antibodies are provided, along with pharmaceutical compositions containing such antibody, kits containing a pharmaceutical composition, and methods of preventing and treating cancer.

24 Claims, 23 Drawing Sheets

(56) References Cited

U.S. PATENT DOCUMENTS

| | | | |
|---|---|---|---|
| 5,770,429 | A | 6/1998 | Lonberg et al. |
| 5,877,293 | A | 3/1999 | Adair et al. |
| 5,892,019 | A | 4/1999 | Schlom et al. |
| 5,939,598 | A | 8/1999 | Kucherlapati et al. |
| 6,054,287 | A | 4/2000 | Gao et al. |
| 6,194,551 | B1 | 2/2001 | Idusogie et al. |
| 6,306,393 | B1 | 10/2001 | Goldenberg |
| 6,489,145 | B1 | 12/2002 | Short |
| 6,605,449 | B1 | 8/2003 | Short |
| 6,737,056 | B1 | 5/2004 | Presta |
| 2002/0004215 | A1 | 1/2002 | Osbourn et al. |
| 2002/0091240 | A1 | 7/2002 | Vasquez et al. |
| 2002/0199213 | A1 | 12/2002 | Tomizuka et al. |
| 2003/0028071 | A1 | 2/2003 | Handy et al. |
| 2003/0031667 | A1 | 2/2003 | Deo et al. |
| 2003/0032995 | A1 | 2/2003 | Handy et al. |
| 2003/0092125 | A1 | 5/2003 | Davis et al. |
| 2003/0118592 | A1 | 6/2003 | Ledbetter et al. |
| 2003/0133939 | A1 | 7/2003 | Ledbetter et al. |
| 2003/0190317 | A1 | 10/2003 | Baca et al. |
| 2003/0194404 | A1 | 10/2003 | Greenfeder et al. |
| 2004/0132101 | A1 | 7/2004 | Lazar et al. |
| 2005/0037421 | A1 | 2/2005 | Honda et al. |
| 2005/0136049 | A1 | 6/2005 | Ledbetter et al. |
| 2006/0121604 | A1 | 6/2006 | Handa et al. |

FOREIGN PATENT DOCUMENTS

| | | |
|---|---|---|
| EP | 0120694 | 10/1984 |
| EP | 0125023 | 11/1984 |
| EP | 0171496 | 2/1986 |
| EP | 0173494 | 3/1986 |
| EP | 315 456 | 5/1989 |
| WO | WO-81/01145 | 4/1981 |
| WO | WO-86/01533 | 3/1986 |
| WO | WO-87/00195 | 1/1987 |
| WO | WO-87/05330 | 9/1987 |
| WO | WO-88/07378 | 10/1988 |
| WO | WO-90/07861 | 7/1990 |
| WO | WO-91/09967 | 7/1991 |
| WO | WO-91/10741 | 7/1991 |
| WO | WO-91/17271 | 11/1991 |
| WO | WO-92/01047 | 1/1992 |
| WO | WO-92/11018 | 7/1992 |
| WO | WO-93/11161 | 6/1993 |
| WO | WO-93/19172 | 9/1993 |
| WO | WO-93/25673 | 12/1993 |
| WO | WO-94/02602 | 2/1994 |
| WO | WO-95/15388 | 6/1995 |
| WO | WO-96/27011 | 9/1996 |
| WO | WO-96/30498 | 10/1996 |
| WO | WO-96/32478 | 10/1996 |
| WO | WO-96/33735 | 10/1996 |
| WO | WO-96/34096 | 10/1996 |
| WO | WO-97/34631 | 9/1997 |
| WO | WO-98/24893 | 6/1998 |
| WO | WO-01/43869 | 6/2001 |
| WO | WO-02/092780 | 11/2002 |
| WO | WO-03/041600 | 5/2003 |
| WO | WO-2004/003019 | 1/2004 |
| WO | WO 2005/068503 | 7/2005 |
| WO | WO-2006055347 A2 | 5/2006 |
| WO | WO-2006/110585 | 10/2006 |
| WO | WO-2007/051112 | 5/2007 |

OTHER PUBLICATIONS

Brown, et al., "Tolerance to Single, but Not Multiple, Amino Acid Replacements in Antibody VH CDR2," The Journal of Immunology, 156: 3285-3291 (1996).

Aplin et al., Preparation, properties, and applications of carbohydrate conjugates of proteins and lipids. *CRC Crit. Rev. Biochem.* 10: 259-306 (1981).

Anderson, Human gene therapy. *Nature.* 392: Suppl. 6679 25-30 (1998).

Angal et al., A single amino acid substitution abolishes the heterogeneity of chimeric mouse/human (IgG4) antibody. *Mol Immunol.* 30: 105-8 (1993).

Arden et al., *AM. Hum. Genet.* 45 suppl.: Abstract A129 (1989).

Arden et al., The receptors for prolactin and growth hormone are localized in the same region of human chromosome 5. *Cytogenet. Cell Gene* 53: 161-5, 1990.

Armour et al., Differential binding to human FcgammaRIIa and FcgammaRIIb receptors by human IgG wildtype and mutant antibodies. *Mol Immunol.* 40: 585-93 (2003).

Ballas et al., Liposomes baring a quaternary ammonium detergent as an efficient vehicle for functional transfer of TMV-RNA into plant protoplasts. *Biochim. Biophys. Acta.* 939: 8-18 (1988).

Barnes et al., Methods for growth of cultured cells in serum-free medium. *Anal. Biochem.* 102: 255-70 (1980).

Batra et al., Recombinant anti-erbB2 immunotoxins containing *Pseudomonas exotoxin. Proc Natl Acad. Sci. USA.* 89: 5867-71 (1992).

Bayer, et al., The avidin-biotin complex in affinity cytochemistry. *Meth Enzym.* 62:308-15 (1979).

Becker et al., An antibody-interleukin 2 fusion protein overcomes tumor heterogeneity by induction of a cellular immune response. *Proc. Natl Acad. Sci. USA.* 93: 7826-31 (1996).

Beckman et al., Antibody constructs in cancer therapy: protein engineering strategies to improve exposure in solid tumors. *Cancer*, 109: 170-9 (2007).

Behr et al., Efficient gene transfer into mammalian primary endocrine cells with lipopolyamine-coated DNA. *Proc. Natl. Acad. Sci. USA.* 86: 6982-6 (1989).

Behr et al., Gene transfer with synthetic cationic amphiphiles: prospects for gene therapy. *Bioconjugate Chem.* 5: 382-9 (1994).

Behr et al., DNA strongly binds to micelles and vesicles containing lipopolyamines or lipointercalants. *Tetrahedron Lett.* 27: 5861-4 (1986).

Better et al., *Escherichia coli* secretion of an active chimeric antibody fragment. *Science.* 240: 1041-3 (1988).

Biocca, et al., Expression and targeting of intracellular antibodies in mammalian cells. *EMBO.* 9: 101-8 (1990).

Bird et al., Single-chain antigen binding protein. *Science.* 242: 423-6 (1988).

Boleti et al., Construction, expression and characterisation of a single chain anti-tumour antibody (scFv)-IL-2 fusion protein. *Ann. Oncol.* 6: 945-7 (1995).

Boulianne et al., Production of functional chimaeric mouse/human antibody. *Nature.* 312: 643-6 (1984).

Brennan et al., Preparation of biospecific antibodies by chemical recombination of monoclonal immunoglobulin G1 fragments. *Science.* 229: 81-3 (1985).

Brinkmann et al., B3(Fv)-PE38KDEL, a single-chain immunotoxin that causes complete regression of a human carcinoma in mice. *Proc. Nat'l Acad. Sci. USA.* 88: 8616-20 (1991).

Brodeur et al., Monoclonal Antibody Production Techniques and Applications, Marcel Dekker, Inc. New York 51-63 (1987).

Brorson et al., Mutational analysis of avidity and fine specificity of anti-levan antibodies. *J. Immunol.*, 163: 6694-701 (1999).

Bruggermann et al., Designer mice: the production of human antibody repertoires in transgenic animals. *Year in Immuno.* 7: 33 (1993).

Brummell et al., Probing the combining site of an anti-carbohydrate antibody by saturation-mutagenesis: role of the heavy-chain CDR3 residues. *Biochemistry*, 32: 1180-7 (1993).

Burks et al., In vitro scanning saturation mutagenesis of an antibody binding pocket. *Proc. Natl. Acad. Sci. USA*, 94: 412-7 (1997).

Burton et al., Human antibodies from combinatorial libraries. *Adv. Immunol.* 57: 191-280 (1994).

Caron et al., Engineered humanized dimeric forms of IgG are more effective antibodies. *J. Exp Med.* 176: 1191-5 (1992).

Carter et al., High level *Escherichia coli* expression and production of a bivalent humanized antibody fragment. *Bio/Technology* 10: 163-7 (1992).

Cassett et al., A peptide mimetic of an anti-CD4 monoclonal antibody by rational design. *Biochem. Biophys. Res. Comm.*, 307: 198-205 (2003).

(56) References Cited

OTHER PUBLICATIONS

Caton et al., Influenza virus hemagglutinin-specific antibodies isolated from a combinatorial expression library are closely related to the immuno response of the donor. *Proc. Natl. Acad. Sci. USA*, 87: 6450-4 (1990).
Cespedes et al., Mouse models in oncogenesis and cancer therapy. *Clin. Transl. Oncol.*, 8(5): 318-29 (2006).
Champe et al., Monoclonal antibodies that block the activity of leukocytes function-associated antigen 1 recognize three discrete epitopes in the inserted domain of CD11a. *J. Biol. Chem.* 270: 1388-94 (1995).
Chappel et al., Identification of the $Fc_\gamma$ receptor class I binding site in human IgG through the use of recombinant IgG1/IgG2 hybrid and point mutated antibodies. *Proc Natl Acad U S A.* 88: 9036-40 (1991).
Chaudhary et al., A recombinant immunotoxin consisting of two antibody variable domains fused to Pseudomonas exotoxin. *Nature.* 339: 394-7 (1989).
Chen et al., Selection and analysis of an optimized anti-VEGF antibody: crystal structure of an affinity-matured Fab in complex with antigen. *J. Mol. Biol.* 293: 865-81 (1999).
Chothia et al., Canonical structures for the hypervariable regions of immunoglobulins. *Mol. Biol.* 196: 901-17 (1987).
Chowdhury, Targeting random mutations to hotspots in antibody variable domains for affinity improvement. *Meth.Mol. Biol.* 178: 269-85 (2002).
Clackson et al., In vitro selection from protein and peptide libraries. *Trends. Biotechnol.* 12: 173-84 (1994).
Co, et al., A humanized antibody specific for platelet integrin gpIIb/IIIa. *J. Immunol.* 152: 2968-76 (1994).
Colby et al., Potent inhibition of huntingtin aggregation and cytotoxicity by a disulfide bond-free single-domain intracellular antibody. *Proc Natl Acad Sci U S A.* 101: 17616-21 (2004).
Coleman, Effects of amino acid sequence changes on antibody-antigen interactions. *Res. Immunol.*, 145: 33-6 (1994).
Conrath et al., Beta-lactamase inhibitors derived from single-domain antibody fragments elicited in the camelidae. *Antimicrob Agents Chemother* 45: 2807-12 (2001).
Cortez-Retamozo et al., Efficient cancer therapy with a nanobody-based conjugate. *Cancer Res.* 64: 2853-57 (2004).
Cunningham et al., High-resolution epitope mapping the hGH-receptor interactions by alanine-scanning mutagenesis. *Science.* 244: 1081-5 (1989).
Dall'Acqua et al., Modulation of the effector functions of a human IgG1 through engineering of its hinge region. *J. Immunol.* 177: 1129-38 (2006).
Daugherty et al., Quantitative analysis of the effect of the mutation frequency on the affinity maturation of single chain Fv antibodies. *Proc Natl Acad Sci U S A.* 97: 2029-34 (2000).
Davies et al., Affinity improvement of single antibody VH domains: Residues in all three hypervariable regions affect antigen binding. *Immunotechnology.* 2: 169-79 (1996).
De Pascalis et al., Grafting of "abbreviated" complementarity-determining regions containing specificity-determining residues essential for ligand contact to engineer a less immonogenic humanized monoclonal antibody. *J. Immunol.* 169: 3076-84 (2002).
Dennis et al., Cancer: off by a whisker. *Nature*, 442: 739-41 (2006).
Desmyter et al., Antigen specificity and high affinity binding provided by one single loop of a camel single domain antibody. *J. Biol. Chem.* 276: 26285-90 (2001).
Dohlsten et al., Monoclonal antibody—superantigen fusion proteins: Tumor-specific agents for T-cell-based tumor therapy. *Proc. Natl Acad. Sci. USA.* 91: 8945-9 (1994).
Edge et al., Deglycosylation of glycoproteins by trifluoromethanesulfonic acid. *Anal Biochem.* 118: 131-7 (1981).
Engvall et al., Enzyme-linked immunosorbent assay, Elisa. 3. Quantitation of specific antibodies by enzyme-labeled anti-immunoglobulin in antigen-coated tubes. *J. Immunol.* 109: 129-35 (1972).

Eppstein et al., Biological activity of liposome-encapsulated murine interferon γ is mediated by a cell membrane receptor. *Proc. Natl. Acad. Sci. USA* 82: 3688-92 (1985).
Evan et al., Isolation of monoclonal antibodies specific for humen c-myc proto-oncogene product. *Mol. Cell. Biol.* 5: 3610-6 (1985).
Ewert et al., Biophysical properties of camelid $V_{HH}$ domains compared to those of human $V_H3$ domains. *Biochemisrty* 41:3628-36, 2002.
Felgner et al., Lipofection: a highly efficient, lipid-mediated DNA-transfection procedure. *Proc. Natl. Acad. Sci USA.* 84: 7413-7 (1987).
Ferrara et al., The carbohydrate at FcgammaRIIIa Asn-162. An element required for high affinity binding to non-fucosylated IgG glycoforms. *J. Biol Chem.* 281: 5032-6 (2006).
Field et al., Purification of a RAS-responsive andenylyl cyclase complex from *Saccharomyces cerevisiae* by use of an epitope addition method. *Mol. Cell. Biol.* 8: 2159-65 (1988).
Fishwild et al., High-avidity human IgG kappa monoclonal antibodies from a novel strain of minilocus transgenic mice. *Nat. Biotechnol.* 14: 845-51 (1996).
Fominaya et al., Target cell-specific DNA transfer mediated by a chimeric multidomain protein. *J. Biol. Chem.* 271: 10560-8 (1996).
Fredericks et al., Identification of potent human anti-IL-1RI antagonist antibodies. *Protein Eng Des Sel.* 17: 95-106 (2004).
Friedman et al., Antitumor activity of the single-chain immunotoxin BR96 sFv-PE40 against established breast and lung tumor xenografts. *J. Immunol.* 150: 3054-61 (1993).
Fujimore et al., A modeling analysis of monoclonal antibody percolation through tumors: a binding-site barrier. *J. Nucl. Med.* 31: 1191-8 (1990).
Gabizon et al., Pharmacokinetics and tissue distribution of doxorubicin encapsulated in stable liposomes with long circulation times. *J. Natl Cancer Inst.* 8: 1484-8 (1989).
Gill et al., Expression of prolactin receptors in normal, benign, and malignant breast tissue: an immunohistological study. *J. Clin Pathol..* 54: 956-60 (2001).
Goding, Conjugation of antibodies with fluorochromes: modifications to the standard methods. *J. Immunol. Meth.* 13: 215-26 (1976).
Graham et al., Characteristics of a human cell line transformed by DNA from human adenovirus type 5. *J. Gen Virol..* 36: 59-74 (1977).
Greenburg et al., A new antigen receptor gene family that undergoes rearrangement and extensive somatic diversification in sharks. *Nature.* 374:168-73 (1995).
Gruber et al., Efficient tumor cell lysis mediated by a bispecific single chain antibody expressed in *Escherichia coli*. *J. Immunol.* 152: 5368-74 (1994).
Guss et al., Structure of the IgG-binding regions of streptococcal protein G. *EMBO* 5: 1567-5 (1986).
Hamers-Casterman et al., Naturally occurring antibodies devoid of light chains. *Nature* 363: 446-8 (1993).
Hank et al., Activation of human effector cells by a tumor reactive recombinant anti-ganglioside GD2 interleukin-2 fusion protein (ch14.18-IL2). *Clin Cancer Res.* 2: 1951-9 (1996).
Hawkins et al., Selection of phage antibodies by binding affinity. Mimicking affinity maturation. *J. Mol Biol.* 226: 889-96 (1992).
Heng et al., Making cell-permeable antibodies (Transbody) through fusion of protein transduction domains (PTD) with single chain variable fragment (scFv) antibodies: potential advantages over antibodies expressed within the intracellular environment (Intrabody). *Med Hypotheses.* 64: 1105-8 (2005).
Hollinger et al., "Diabodies": Small bivalent and bispecific antibody fragments. *Proc. Natl. Acad. Sci. USA*, 90: 6444-8 (1993).
Holm et al., Functional mapping and single chain construction of the anti-cytokeratin 8 monoclonal antibody TS1. *Mol. Immunol.* 44: 1075-84 (2007).
Holt et al., Domain antibodies: Proteins for therapy. *Trends Biotechnol.* 21: 484-90 (2003).
Hoogenboom et al., By-passing immunisation. Human antibodies from synthetic repertoires of germline VH gene segments rearranged in vitro. *J. Mol. Biol.* 227:381-8 (1991).
Hu et al., A chimeric Lym-1/interleukin 2 fusion protein for increasing tumor vascular permeability and enhancing antibody uptake. *Cancer Res.* 56: 4998-5004 (1996).

(56) References Cited

OTHER PUBLICATIONS

Hu et al., Isolation and characterization of two novel forms of the human prolactin receptor generated by alternative splicing of a newly identified exon 11. *J. Biol. Chem.* 276: 41087 (2001).
Hu et al., The human prolactin receptor gene structure and alternative promoter utilization: the generic promoter hPIII and a novel human promoter hP(N). *J. Clin. Endocr. Metab.* 84: 1153-6 (1999).
Huls et al., Tumor cell killing by in vitro affinity-matured recombinant human monoclonal antibodies. *Cancer Immunol Immunother.* 50: 163-71 (2001).
Huston et al., Protein engineering of antibody binding sites: Recovery of specific activity in an anti-digoxin single-chain Fv analogue produced in *Escherichia coli. Proc. Natl. Acad. Sci. USA* 85: 5879-83 (1988).
Hwang et al., Hepatic uptake and degradation of unilamellar sphingomyelin/cholecterol liposomes: A kinetic study. *Proc. Natl. Acad. Sci. USA.* 77: 4030-4 (1980).
Isaacs et al., Therapy with monoclonal antibodies. II. The contribution of Fc gamma receptor binding and the influence of C(H)1 and C(H)3 domains on in vivo effector function. *J. Immunol.* 161: 3862-9 (1998).
Ishida et al., Production of human monoclonal and polyclonal antibodies in TransChromo animals. *Cloning Stem Cells.* 4: 91-102 (2002).
Jakobovitis et al., Analysis of homozygous mutant chimeric mice: Deletion of the immunoglobulin heavy-chain joining region blocks B-cell development and antibody production. *Proc. Natl. Acad. Sci. USA.* 90: 2551-5 (1993).
Jakobovits et al., Germ-line transmission and expression of a human-derived yeast artificial chromosome. *Nature.* 362: 255-8 (1993).
Jang et al., The structural basis for DNA binding by an anti-DNA autoantibody. *Mol. Immunol.* 35: 1207-17 (1998).
Jespers et al., Guiding the selection of human antibodies from phage display repertoires to a single epitope of an antigen. *Bio/Technology.* 12: 899-903 (1994).
Jones et al., Replacing the complementarity-determining regions in a human antibody with those from a mouse. *Nature* 312: 522-5 (1986).
Jones, Proteinase mutants of *Saccharomyces cerevisiae. Genetics.* 85: 23-33 (1977).
Kettleborough et al., Humanization of a mouse monoclonal antibody by CDR-grafting: the importance of framework residues on loop conformation. *Protein Eng...* 4: 773-83 (1991).
Kline et al., Identification and characterization of the prolactin-binding protein in human serum and milk. *J. Biol. Chem.,* 276(27): 24760-6 (2001).
Kobayashi et al., Tryptophan H33 plays an important role in pyrimidine (6-4) pyrimidone photoproduct binding by a high-affinity antibody. *Protein Eng.* 12: 879-84 (1999).
Kohler et al., Continuous cultures of fused cells secreting antibody of predefined specificity. *Nature.* 256: 495-7 1975.
Kozbor, A human hybrid myeloma for production of human monoclonal antibodies. *J. Immunol.,* 133: 3001-5 (1984).
Kreitman et al., Cytotoxic activities of recombinant immunotoxins composed of *Pseudomonas* toxin or diphtheria toxin toward lymphocytes from patients with adult T-cell leukemia. *Leukemia.* 7: 553-62 (1993).
Kuan et al., Recombinant immunotoxin containing a disulfide-stabilized Fv directed at erbB2 that does not require proteolytic activation. *Biochemisrty.* 35: 2872-7 (1996).
Kumar et al., Molecular cloning and expression of the Fabs of human autoantibodies in *Escherichia coli.* Determination of the heavy or light chain contribution to the anti-DNA/-cardiolipin activity of the Fab. *J. Biol. Chem.,* 275: 35129-36 (2000).
Letsinger, Cholesteryl-conjugated oligonucleotides: Synthesis, properties, and activity as inhibitors of replication of human Immunodeficiency virus in cell culture. *Proc Natl Acad Sci USA.* 86: 6553-6 (1989).
Leung et al., Engineering a unique glycosylation site for site-specific conjugation of haptens to antibody fragments. *J. Immunol.* 154: 5919-26 (1995).

Li et al., Activation of signal transducer and activator of transcription 5 in human prostate cancer is associated with high histological grade. *Cancer Res..* 64: 4774-82 (2004).
Lindmark et al., Binding of immunoglobulins to protein A and immunoglobulin levels in mammalian sera. *J. Immunol. Meth.* 62: 1-13 (1983).
Low et al., Mimicking somatic hypermutation: affinity maturation of antibodies displayed on bacteriophage using a bacterial mutator strain. *J. Mol. Biol.* 260: 359-68 (1996).
MacCallum et al., Antibody-antigen interactions: contact analysis and binding site topography. *J. Mol. Biol.,* 262: 732-45 (1996).
Malone et al., Cationic liposome-mediated RNA transfection. *Proc. Natl Acad. Sci. USA.* 86: 6077-81 (1989).
Marks et al., By-passing immunization. Human antibodies from V-gene libraries displayed on phage. *J. Mol. Biol.* 222: 581-97 (1991).
Marks et al., Selection of human antibodies from phage display libraries. *Methods Mol Biol.* 248:161-76 (2004).
Martin et al., Irreversible coupling of immunoglobulin fragments to preformed vesicles. *J. Biol. Chem.* 257: 286-8 (1982).
Massey, Catalytic antibodies catching on. *Nature.* 328: 457-8 (1987).
Mather et al., Culture of testicular cells in hormone-supplemented serum-free medium. *Annals N.Y. Acad. Sci.* 383: 44-68 (1982).
Mather, Establishment and characterization of two distinct mouse testicular epithelial cell lines. *Biol. Reprod.* 23: 243-251 (1980).
Mhashilkar et al., Inhibition of HIV-1 Tat-mediated LTR transactivation and HIV-1 infection by anti-Tat single chain intrabodies. *EMBO.* 14: 1542-51 (1995).
Miller, Human gene therapy comes of age. *Nature:* 357: 455-60 (1992).
Monoclonal Anti-human Prolactin R Antibody, MAB1167, RND Systems, Jun. 6, 2005.
Morimoto et al., Single-step purification of F(ab')2 fragments of mouse monoclonal antibodies (immunoglobulins G1) by hydrophobic interaction high performance liquid chromatography using TSKgel Phenyl-5PW. *J. Biochem. Biophys. Meth.* 24:; 107-17 (1992).
Morrison et al., Genetically engineered antibody molecules. *Adv. Immunol.,* 44: 65-92 (1988).
Morrison et al., Chimeric human antibody molecules; Mouse anitgen binding domains with human constant region domains. *Proc. Natl. Acad. Sci. USA.* 81: 6851-55 (1984).
Munson et al., Ligand: a versatile computerized approach for characterization of ligand-binding systems. *Anal. Biochem.* 107: 220-39 (1980).
Neri et al., High-affinity antigen binding by chelating recombinant antibodies (CRAbs). *Mol Biol.* 246: 367-73 (1995).
Neuberger et al., Recombinant antibodies possessing novel effector functions. *Nature.* 312: 604-8 (1984).
Nguyen et al., The specific variable domain of camel heavy-chain antibodies is encoded in the germline. *J.Mol. Biol.* 275: 413-8 (1998).
Nicholls et al., Characterization of single-chain antibody (sFv)-toxin fusion proteins produced in vitro in rabbit reticulocyte lysate. *J. Biol. Chem.* 268: 5302-8 (1993).
Nishimiya et al., Thermodynamic consequences of grafting enhanced affinity toward the mutated antigen onto an antibody. *J. Biol. Chem.* 275: 12813-20 (2000).
Nuttall et al., Isolation of the new antigen receptor from wobbegong sharks, and use as a scaffold for the display of protein loop libraries. *Mol Immunol.* 38: 313-26 (2001).
Ohmori et al., The enhancing effect of anionic alpha-helical peptide on cationic peptide-mediating transfection systems. *Biochem Biophys Res Commun.* 235: 726-9 (1997).
Olafsen et al., Characterization of engineered anti-p185$^{HER-2}$ (scFv-$C_H3$)$_2$ antibody fragments (minibodies) for tumor targeting. *Protein Eng Des Sel...* 17: 315-23 (2004).
Paborsky et al., Mammalian cell transient expression of tissue factor for the production of antigen. *Protein Eng.* 3: 547-53 (1990).
Padlan, A possible procedure for reducing the immunogenicity of antibody variable domains while preserving their ligand-binding properties. *Molec. Immun.* 28: 489-98 (1991).
Padlan, Anatomy of the antibody molecule. *Molec. Immunol.* 31: 169-217 (1994).

(56) References Cited

OTHER PUBLICATIONS

Pastan et al., Immunotoxins. *Cell.* 47: 641-8 (1986).
Peirce et al., Quantification of prolactin receptor mRNA in multiple human tissues and cancer cell lines by real time RT-PCR. *J. Endocr.* 171: R1-R4 (2001).
Perrot-Applanat et al., Dominant negative and cooperative effects of mutant forms of prolactin receptor. *Molec. Endocr.* 11: 1020-32 (1997).
Pinnaduwage et al., Use of a quaternary ammonium detergent in liposome mediated DNA transfection of mouse L-cells. *Biochim. Biophys. Acta.* 985: 33-7 (1989).
Pluckthun, The Pharmacology of Monoclonal Antibodies, Springer-Verlag, New York. 113: 269-315 (1994).
Pollard et al., Polyethylenimine but not cationic lipids promotes transgene delivery to the nucleus in mammalian cells. *J. Biol. Chem.* 273: 7507-11 (1998).
Powers et al., Expression of single-chain Fv-Fc fusions in *Pichia pastoris*. *Immunol Methods.* 251: 123-35 (2001).
Presta et al., Engineering therapeutic antibodies for improved function. *Biochem. Soc. Trans.* 30: 487-90 (2001).
Rajpal et al., A general method for greatly improving the affinity of antibodies by using combinatorial libraries. *Proc Natl Acad Sci USA.* 102: 8466-71 (2005).
Reichman et al., Single domain antibodies: comparison of camel VH and camelised human VH domains. *Immunol. Methods.* 231: 25-38 (1999).
Reyes et al., Expression of human beta-interferon cDNA under the control of a thymidine kinase promoter from herpes simplex virus. *Nature.* 297: 598-601 (1982).
Riechmann et al., Reshaping human antibodies for therapy. *Nature.* 332: 323-7 (1988).
Rose et al., A new cationic liposome reagent mediating nearly quantitative transfection of animal cells. *Biotechnique.* 10: 520-5 (1991).
Roth et al., VDJ recombination: a transposase goes to work. *Cell.* 94: 411-4 (1998).
Rothman et al., Antibody-dependent cytotoxicity mediated by natural killer cells is enhanced by castanospermine-induced alterations of IgG glycosylation. *Mol Immunol.* 26: 1113-23 (1989).
Rudnick et al., Affinity and avidity in antibody-based tumor targeting. *Cancer Biother. Radiopharm.*, 24: 155-62 (2009).
Salfeld et al., Isotype selection in antibody engineering. *Nat. Biotech.*, 25(12): 1369-72 (2007).
Santos et al., Cloning, characterization, and tissue distribution of prolactin receptor in the sea bream (*Sparus aurata*). *Gen. Comp. Endocrinol.*, 121(1): 32-47 (2001).
Sarmay et al., Mapping and comparison of the interaction sites on the Fc region of IgG responsible for triggering antibody dependent cellular cytotoxicity (ADCC) through different types of human Fc gamma receptor. *Molec. Immunol.* 29: 633-9 (1992).
Schmidt et al., A bivalent single-chain antibody-toxin specific for ErbB-2 and the EGF receptor. *Int. J. Cancer.* 65: 538-46 (1996).
Schoonjans et al., Fab chains as an efficient heterodimeration scaffold for the production of recombinant bispecific and trispecific antibody derivatives. *J. Immunol.* 165: 7050-7 (2000).
Schuurman et al., The inter-heavy chain disulfide bonds of IgG4 are in equilibrium with intra-chain disulfide bonds. *Mol Immunol.* 38: 1-8 (2001).
Shalaby et al., Development of humanized bispecific antibodies reactive with cytotoxic lymphocytes and tumor calls overexpressing the HER2 protooncogene. *J. Exp. Med.* 175: 217-25 (1992).
Shields et al., Lack of fucose on human IgG1 N-linked oligosaccharide improves binding to human FcγRIII and antibody-dependent cellular toxicity. *J. Biol Chem.* 277: 26733-40 (2002).
Shih et al., A fluorouridine-anti-CEA immunoconjugate is therapeutically effective in a human colonic cancer xenograft model. *Int. J. Cancer.* 46: 1101-6 (1990).
Shih et al., Site-specific linkage of methotrexate to monoclonal antibodies using an intermediate carrier. *Int J. Cancer.* 41: 832-9 (1988).
Shinkawa et al., The absence of fucose but not the presence of galactose or bisecting N-acetylglucosamine of human IgG1 complex-type oligosaccharide shows the critical role of enhancing antibody-dependent cellular cytotoxicity. *J. Biol Chem.* 278: 3466-73 (2003).
Shopes, A genetically engineered human IgG mutant with enhanced cytolytic activity. *J. Immunol.* 148: 2918-22 (1992).
Shu et al., Secretion of a single-gene-encoded immunoglobulin from myeloma cells. *Proc. Natl. Acad. Sci. USA.* 90: 7995-8 (1993).
Sissom et al., Anti-growth action on mouse mammary and prostate glands of a monoclonal antibody to prolactin receptor. *Am. J. Pathol.* 133: 589-95 (1988).
Skerra et al., Assembly of a functional immunoglobulin Fv fragment in *Escherichia coli*. *Science.* 240: 1038-41 (1988).
Smith-Gill et al., Contributions of immunoglobulin heavy and light chains to antibody specificity for lysozyme and two haptens. *J. Immunol.*, 139: 4135-44 (1987).
Sojar et al., A chemical method for the deglycosylation of proteins. *Arch. Biochem. Biophys.* 259: 52-7 (1987).
Song et al., Light chain of natural antibody plays a dominant role in protein antigen binding. *Biochem. Biophys. Res. Comm.*, 268: 390-4 (2000).
Stella et al., Prodrugs: A chemical approach to targeted drug delivery. Directed Drug Delivery. 247-67, Humana Press (1985).
Stemmer, DNA shuffling by random fragmentation and reassembly: In vitro recombination for molecular evolution. *Proc. Natl. Acad. Sci. U S A.* 91: 10747-51 (1994).
Steplewski et al., Biological activity of human-mouse IgG1, IgG2, IgG3, and IgG4 chimeric monoclonal antibodies with antitumor specificity. *Proc Natl Acad Sci U S A.* 85: 4852-6 (1988).
Sternberger, et al., The unlabeled antibody enzyme method of immunohistochemistry: preparation and properties of soluble antigen-antibody complex (horseradish peroxidase-antihorseradish peroxidase) and its use in identification of spirochetes. *J. Histochem. Cytochem.* 18: 315-33 (1970).
Stevenson et al., A chimeric antibody with dual Fc regions (bisFabFc) prepared by manipulations at the IgG hinge. *Anti-Cancer Drug Design.* 3: 219-30 (1989).
Stinchcomb et al., Isolation and characterisation of a yeast chromosomal replicator. *Nature*, 282: 39-43 (1979).
Studnicka et al., Human-engineered monoclonal antibodies retain full specific binding activity by preserving non-CDR complementarity-modulating residues. *Protein Eng.* 7: 805-14 (1994).
Swartzman et al., Quantification of prolactin receptor mRNA in multiple human tissues and cancer cell lines by real time RT-PCR. *Anal Biochem.* 271: 143-51 (1999).
Talmadge et al., Murine models to evaluate novel and conventional therapeutic strategies for cancer. *Am. J. Pathol.*, 170(3): 793-804 (2007).
Thompson et al., An anti-CD3 single-chain immunotoxin with a truncated diphtheria toxin avoids inhibition by pre-existing antibodies in human blood. *J. Biol. Chem.* 270: 28037 (1995).
Thotakura et al., Enzymatic deglycosylation of glycoproteins. *Meth. Enzymol.* 138: 350-9 (1987).
Thurber et al., Antibody tumor penetration: transport opposed by systemic and antigen-mediated clearance. *Adv. Drug Deliv. Rev.*, 60: 1421-34 (2008).
Touraine et al., Increased expression of prolactin receptor gene assessed by quantitative polymerase chain reaction in human breast tumors versus normal breast tissues. *Clin Endocrinol Metab.*, 83: 667-74 (1998).
Tutt et al., Trispecific F(ab')3 derivatives that use cooperative signaling via the TCR/CD3 complex and CD2 to activate and redirect resting cytotoxic T cells. *J. Immunol.* 147: 60-9 (1991).
Tworoger et al., Association between plasma prolactin concentrations and risk of breast cancer among predominately premenopausal women. *Cancer Res.* 66: 2476-82 (2006).
Tworoger et al., Plasma prolactin concentrations and risk of postmenopausal breast cancer. *Cancer Res.* 64: 6814-9 (2004).
Umana et al., Engineered glycoforms of an antineuro-blastoma IgG1 with optimized antibody-dependent cellular cytotoxic activity. *Nat Biotechnol.* 17: 176-80 (1999).
Urlaub et al., Isolation of Chinese hamster cell mutants deficient in dihydrofolate reductase activity. *Proc. Natl. Acad. Sci. USA.* 77: 4216-20 (1980).

(56) References Cited

OTHER PUBLICATIONS

Vajdos et al., Comprehensive functional maps of the antigen-binding site of an anti-ErbB2 antibody obtained with shotgun scanning mutagenesis. *J. Mol. Biol.* 320: 415-28 (2002).

Vallera et al., Anti-graft-virus-host disease effect of DT390-AntiCD3sFv, a single-chain Fv fusion immunotoxin specifically targeting the CD3e moiety of the T-cell receptor. *Blood.* 88: 2342-53 (1996).

Verhoeyer et al., Reshaping human antibodies: Grafting an antilysozyme activity. *Science.* 239: 1534-6 (1988).

Verma, Gene therapy. *Sci. Am.* 263: 68-84 (1990).

Voskoglou-Nomikos et al., Clinical predictive value of the in vitro cell line, human xenograft, and mouse allograft preclinical cancer models. *Clin. Cancer Res.*, 9: 4227-39 (2003).

Ward et al., Binding activities of a repertoire of single immunoglobulin variable domains secreted from *Escherichia coli*. *Nature.* 341: 544-6 (1989).

Wels et al., EGF receptor and p185erbB-2-specific single-chain antibody toxins differ in their cell-killing activity on tumor cells expressing both receptor proteins. *Int. J. Can.* 60: 137-44 (1995).

Wennbo et al., Activation of the prolactin receptor but not the growth hormone receptor is important for induction of mammary tumors in transgenic mice. *Clin Invest.* 100: 2744-51 (1997).

Wheeler et al. Intrabody-based strategies for inhibition of vascular endothelial growth factor receptor-2: effects on apoptosis, cell growth, and angiogenesis. *FASEB J.* 17: 1733-5 (2003).

Willems et al., Optimizing expression and purification from cell culture medium of trispecific recombinant antibody derivatives. *Chromatogr. B Analyt Technol. Biomed. Life Sci.* 786: 161-76 (2003).

Wilman, Prodrugs in cancer chemotherapy. *Biochem. Soc. Trans.* 14: 375-82 615th Meeting Belfast (1986).

Winter et al., Making antibodies by phage display technology. *Annu. Rev. Immunol.* 12: 433-55 (1994).

Wolff et al., Monoclonal antibody homodimers: enhanced antitumor activity in nude mice. *Cancer Res.* 53: 2560-5 (1993).

Wu et al., Humanization of a murine monoclonal antibody by simultaneous optimization of framework and CDR residues. *J. Mol. Biol.*, 294: 151-62 (1999).

Xu et al., A molecular mimic of phosphorylated prolactin markedly reduced tumor incidence and size when DU145 human prostate cancer cells were grown in nude mice. *Cancer Res . . .* 61: 6098-104 (2001).

Xu et al., Residue at position 331 in the IgG1 and IgG4 CH2 domains contributes to their differential ability to bind and activate complement. *J. Biol Chem.* 269: 3469-74 (1994).

Yamane-Ohnuki et al., Establishment of FUT8 knockout Chinese hamster ovary cells: an ideal host cell line for producing completely defucosylated antibodies with enhanced antibody-dependent cellular cytotoxicity. *Biotechnol Bioeng.* 87: 614-22 (2004).

Yaniv, Enhancing elements for activation of eukaryotic promoters. *Nature.* 297: 17-8 (1982).

Yu et al., Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells. *Int. J. Cancer.* 56: 244-8 (1994).

Zaccolo et al., The effect of high-frequency random mutagenesis on in vitro protein evolution: a study on TEM-1 beta-lactamase. *Mol. Biol.* 285: 775-83 (1999).

Zapata et al., Engineering linear F(ab')2 fragments for efficient production in *Escherchia coli* and enhanced antiproliferative activity. *Protein Eng.* 8: 1057-62 (1995).

Zhou et al., Lipophilic polylysines mediate efficient DNA transfection in mammalian cells. *Biochim. Biophys. Acta.* 1065: 8-14 (1991).

International Search Report and Written Opinion, PCT/US2007/076160, Aug. 14, 2008.

Figure 2: PRLR-specific antibodies inhibit pERK 1/2 phosphorylation
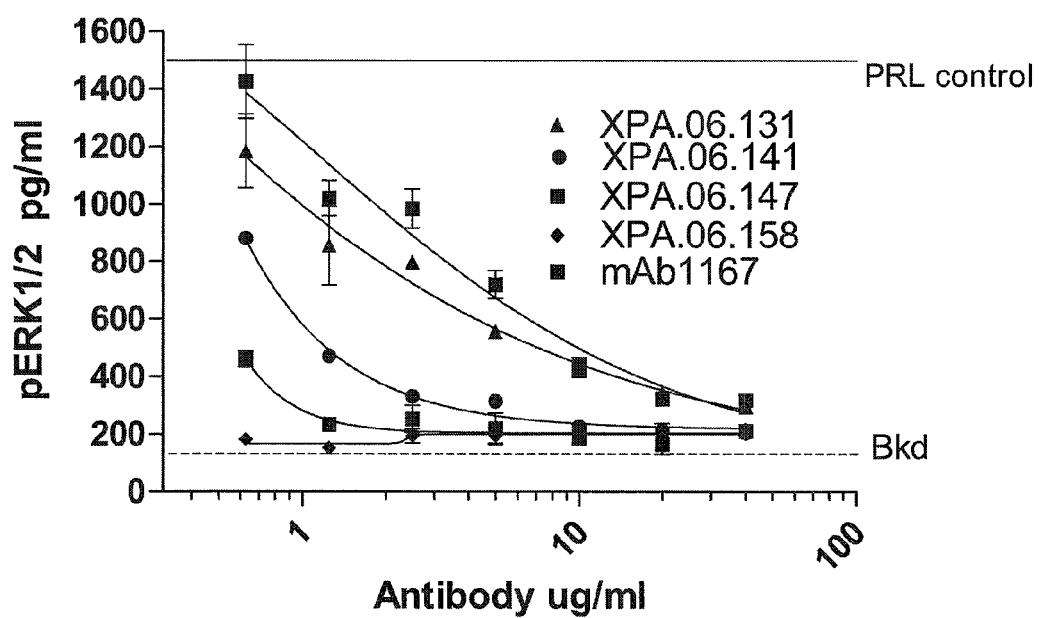

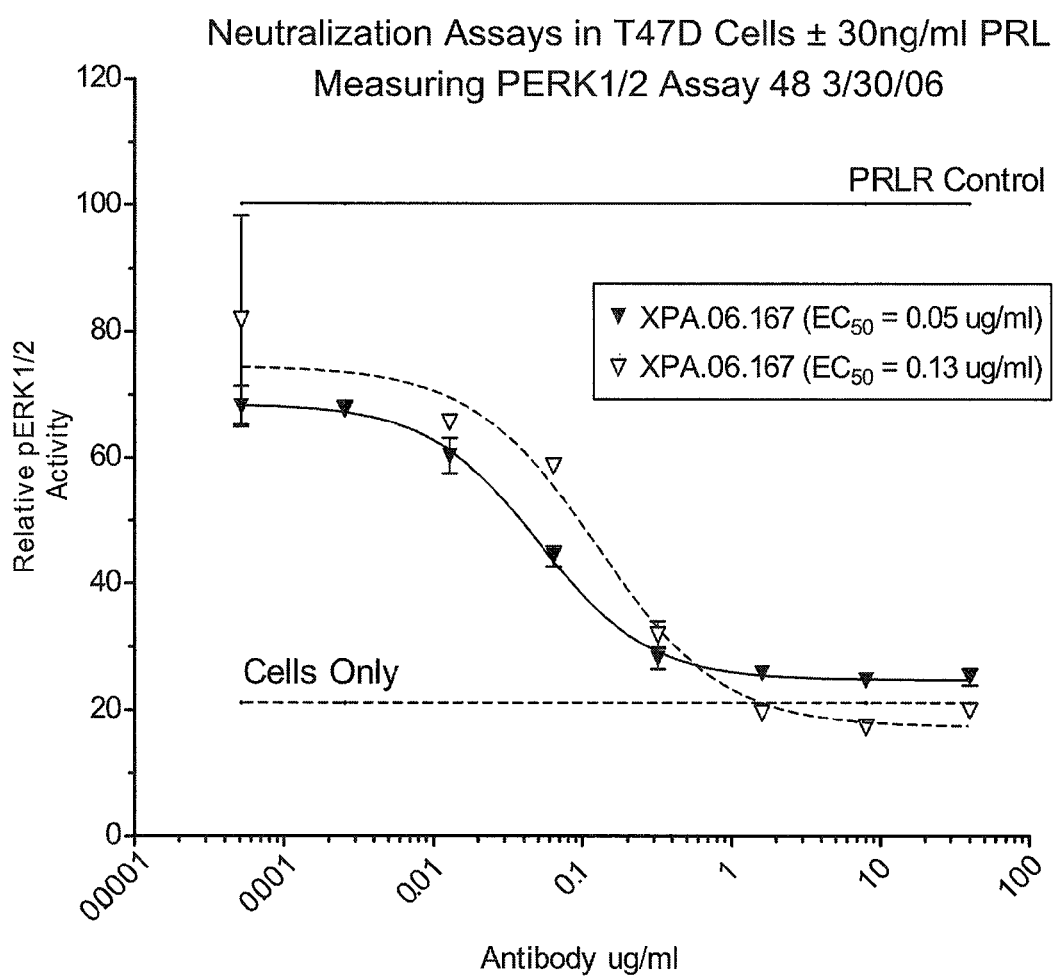
Figure 3: PRLR-specific antibodies inhibit pERK 1/2 phosphorylation

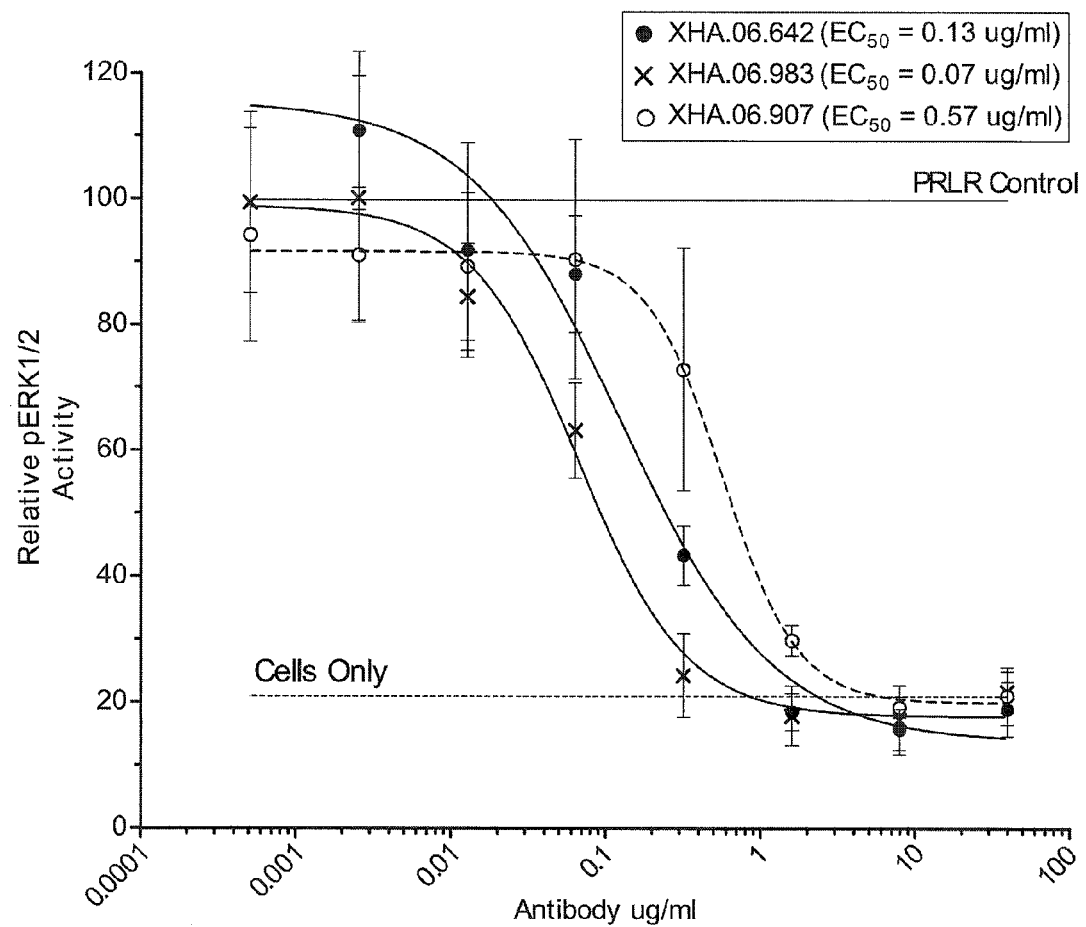
Figure 4: PRLR-specific antibodies inhibit pERK 1/2 phosphorylation

Figure 5: scFv at 5 ug/ml inhibits proliferation of tumor cell line
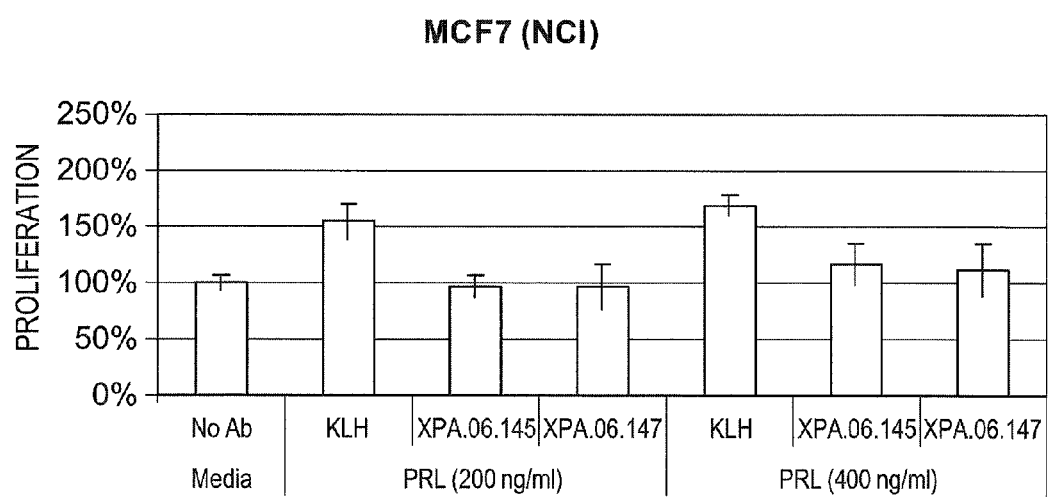

Figure 6: PRLR-specific antibodies inhibit PRL-induced receptor phosphorylation
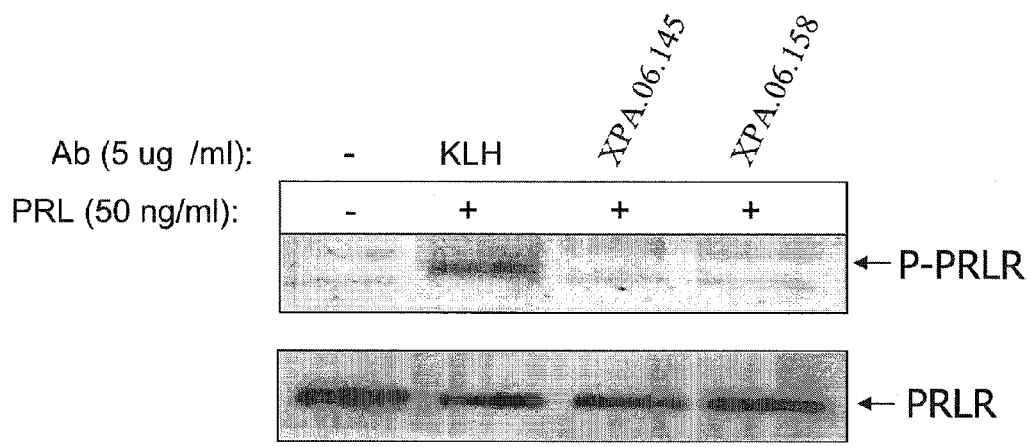

FIGURE 7A

SEQ ID NO: 20
EVQLLESGGGLVQPGGSLRLSCAASGFTFSNYGMHWVRQAPGKGLEWVAVISYDGSNKYYADSVKGRFTISRDNS
KNTLYLQMNSLRAEDTAVYYCATPVVVAPGYWGQGTLVTV
SEQ ID NO: 21
QSVLTQPPSASGTPGQRVTISCSGSSSNIGSNTVNWYQQLPGTAPKLLIYDNNNRPSGVPDRFSGSKSGTSASLAISG
LRSEDEADYYCAAWDDSLSGPVFGGGTKLTVL

SEQ ID NO: 22
EVQLLESGGGLVQPGGSLRLSCAASGFTFDDYGMSWVRQAPGKGLEWVAIISYDGSYTYYADSVKGRFTISRDNS
KNTLYLQMNSLRAEDTAVYYCARASSTSDYWGQGTLVTV
SEQ ID NO: 23
QSVLTQPPSASGTPGQRVTISCSGSSSNIGNNAVNWYQQLPGTAPKLLIYDNYRRPPGIPDRFSGSKSGTSASLAISGL
RSEDXADYYCAVWDGRLNGPVFGGGTKLTVL

SEQ ID NO: 24
EVQLLESGGGLVQPGGSLRLSCAASGFTFDDYGMSWVRQAPGKGLEWVSGISWNSGVVAYADSVKGRFTISRDNS
KNTLYLQMNSLRAEDTAVYYCTTYVPYSRWGQGTLVTV
SEQ ID NO: 25
QSVLTQPPSASGTPGQRVTISCSGSSSNIGSNTVNWYQQLPGTAPKLLIYDNNKRPSGVPDRFSGSKSGTSASLAISG
LRSEDEADYYCAAWDDSLSGPLFGGGTKLTVL

SEQ ID NO: 26
EVQLLESGGGLVQPGGSLRLSCAASGFTFNSYPVHWVRQAPGKGLEWVAVISYDGNTKYYADSVKGRFTISRDNS
KNTLYLQMNSLRAEDTAVYYCARDNPPFDYWGQGTLATV
SEQ ID NO: 27
QSVLTQPPSASGTPGQRVTISCSGSSSNIGNNYVSWYQQLPGTAPKLLIYDNNNRPSGVPDRFSGSKSGTSASLAISG
LRSEDEADYYCEAWDDTLNGPHVVFGGGTKLTVL

SEQ ID NO: 28
EVQLLESGGGLVQPGGSLRLSCAASGFTFSNSGMHWVRQAPGKGLEWVAAISYDGSNKYYADSVKGRFTISRDNS
KNTLYLQMNSLRAEDTAVYYCARADSSGTVDYWGQGTLVTV
SEQ ID NO: 29
QSVLTQPPSASGTPGQRVTISCSGSNSNIGSNTVNWYQQLPGTAPKLLIYDNYNRPSGVPDRFSGSKSGTSASLAISG
LRSKDEADYYCAAWDDSLNGLVFGGGTKLTVL

SEQ ID NO: 30
EVQLLESGGGLVQPGGSLRLSCAASGFTFSSYGMHWVRQAPGKGLEWVSAIGGRGVSTYYADSVKGRFTISRDNS
KNTLYLQMNSLRAEDTAVYYCARGSNWTHALGFDPWGQGTLVTV
SEQ ID NO: 31
QSVLTQPPSASGTPGQRVTISCSGSSSNIGSNTVNWYQQLPGTAPKLLIYGNSNRPSGVPDRFSGSKSGTSASLAISGL
RSEDEADYYCAGWDGRLIGWVFGGGTKLTVL

SEQ ID NO: 32
EVQLLESGGGLVQPGGSLRLSCAASGFTFDDYGMSWVRQAPGKGLEWVSLISWDGGSTYYADSVKGRFTISRDNS
KNTLYLQMNSLRAEDTAVYYCATGIAVAGFDYWGQGTLVTV
SEQ ID NO: 33
QSVLTQPPSASGTPGQRVTISCSGSSSNIGSNAVNWYQQLPGTAPKLLIYDSNKRPSGVPDRFSGSKSGTSASLAISGL
RSEDEADYYCAAWDNSLNGWVFGGGTKLTVL

SEQ ID NO: 34
EVQLLESGGGLVQPGGSLRLSCAASGFTFSSYGMHWVRQAPGKGLEWVSLISWDGYRTHYADSVKGRFTISRDNS
KNTLYLQMNSLRAEDTAMYYCTTGASYHALWGQGTLVTV
SEQ ID NO: 35
QSVLTQPPSASGTPGQRVTISCSGSRSNIGNNYVSWYQQLPGTAPKLLIYDDIKRPSGVPDRFSGSKSGTSASLAISGL
RSEDEADYYCATWDDSLNGPVFGGGTKLTVL

SEQ ID NO: 36
EVQLLESGGGLVQPGGSLRLSCAASGFTFSDYGMHWVRQAPGKGLEWVALISFDGSKTNYGGPVQGRFTISRDNS
ENTLYLQMNSLRAEDTAVYYCTRGAFDIWGQGTLVTV
SEQ ID NO: 37
QSVLTQPPSASGTPGQRVTISCSGSSSNIGSNYVYWYQQLPGTAPKLLIYDNNKRPSGVPDRFSGSKSGTSASLAISG
LRSEDEADYYCAAWDDSLKPVFGGGTKLTVL

FIGURE 7B

SEQ ID NO: 38
EVQLLESGGGLVQPGGSLRLSCAASGFTFS<u>SYGMS</u>WVRQAPGKGLEWVA<u>FISYDGNKESYADSVK</u>GRFTISRDNSK
NTLYLQMNSLRAEDTAVYYCAK<u>GGYGLFDY</u>WGQGTLVTV
SEQ ID NO: 39
QSVLTQPPSASGTPGQRVTISC<u>SGNSSNIGSNYVY</u>WYQQLPGTAPKLLIY<u>DNNKRPS</u>GVPDRFSGSKSGTSASLAISG
LRSEDEADYYC<u>AAWDDSLSGRV</u>FGGRTKLTVL

SEQ ID NO: 40
EVQLLESGGGLVQPGGSLRLSCAASGFTFG<u>SYGMH</u>WVRQAPGKGLEWVS<u>LISWDGGSTYYADSVK</u>GRFTISRDNS
KNTLYLQMNSLRAEDTAVYYCAS<u>SISAAATGLDY</u>WGQGTLVTV
SEQ ID NO: 41
QSVLTQPPSASGTPGQRVTISC<u>SGSTSNIGSNTVN</u>WYQQLPGTVPKLLIY<u>ENKKRPS</u>GVPDRFSGSKSGTSASLAISGL
RSEDEADYYC<u>AAWDDSLSGWV</u>FGGGTKLTVL

SEQ ID NO: 42
EVQLLESGGGLVQPGGFLRLSCAASGFTFS<u>SYSMN</u>WVRQAPGKGLEWVA<u>FIRYDGSNKYYADSVK</u>GRFTISRDNS
KNTLYLQMNSLRAEDTAVYYCAT<u>RRAIAVAGAFDI</u>WGQGTLVTV
SEQ ID NO: 43
QSVLTQPPSASGTPGQRVTISC<u>SGSASNIGINGVN</u>WYQQLPGTAPKLLIY<u>DNNKRPS</u>GVPDRFSGSKSGTSASLAISG
LRSEDEADYYC<u>AAWDDSLSGQVV</u>FGGGTKLTVL

SEQ ID NO: 44
EVQLLESGGGLVQPGGSLRLSCAASGFTFD<u>DYGMS</u>WVRQVPGKGLEWVS<u>LISWDGGSTYYADSVK</u>GRFTISRDNS
KNTLYLQMNSLRAEDTAVYYCAR<u>PSGAYPTPFDN</u>WGQGTLVTV
SEQ ID NO: 45
QSVLTQPPSASGTPGQRVTISC<u>SGSTSNIGSNYVY</u>WYQQLPGTAPKLLIY<u>DNNKRPS</u>GVPDRFSGSKSGTSASLAISG
LRSEDEADYYC<u>AAWDDSLSGWV</u>FGGGTKLTVL

SEQ ID NO: 46
EVQLLESGGGLVQPGGSLRLSCAASGFTFT<u>SGPMS</u>WVRQAPGKGLEWVA<u>VISYDGSNKYYADSVK</u>GRFTISRDNS
KNTLYLQMNSLRAEDTAVYYCAR<u>GAEIFDI</u>WGQGTLVTV
SEQ ID NO: 47
QSVLTQPPSASGTPGQRVTISC<u>SGSSSNIGSNTVN</u>WYQQLPGTAPKLLIY<u>GNNRPS</u>GVPDRFSGSKSGTSASLAISG
LRSEDEADYYC<u>ASWDDSLSGVV</u>FGGGTKLTVL

SEQ ID NO: 48
EVQLLESGGGLVQPGGSLRLSCAASGFTFD<u>DYGMS</u>WVRQAPGKGLEWVS<u>LISWDGGSTYYADSVK</u>GRFTISRDNS
KNTLYLQMNSLRAEDTAVYYCTR<u>GFDP</u>WGQGTLVTV
SEQ ID NO: 49
QSVLTQPPSASGTPGQRVTISC<u>SGSSSNIGSNTVN</u>WYQQLPGTAPKLLIY<u>DNNKRPS</u>GVPDRFSGSKSGTSASLAISG
LRSEDEADYYC<u>MIWPSNAWV</u>FGGRTKLTVL

SEQ ID NO: 50
EVQLLESGGGLVQPGGSLRLSCAASGFTFK<u>SSPMH</u>WVRQAPGKGLEWVS<u>GVSWNGSRTHYVDSVKR</u>RFTISRDNS
KNTLYLQMNSLRAEDTAVYYCAR<u>GAPAFDI</u>WGQGTLVTV
SEQ ID NO: 51
QSVLTQPPSASGTPGQRVTISC<u>SGTTSSIGSNTVN</u>WYQQLPGTAPKLLIY<u>DNNKRPS</u>GVPDRFSGSKSGTSASLAISGL
RSEDEADYYC<u>AAWDDSLNGVV</u>FGGGTKLTVL

SEQ ID NO: 52
EVQLLESGGGLVQPGGSLRLSCAASGFTFS<u>SYAMS</u>WVRQAPGKGLEWVS<u>GVGSSGVNTYYADSVK</u>GRFTISRDNS
KNTLYLQMNSLRAEDTAVYYCAR<u>VGATSSTHFDY</u>WGQGTLVTV
SEQ ID NO: 53
QSVLTQPPSASGTPGQRVTISC<u>SGSRFNIGSNTVN</u>WYQQLPGTAPKLLIY<u>RNENRPS</u>GVPDRFSGSKSGSSASLAISGL
RSEDEADYYC<u>AAWDGSLSAWV</u>FGGGTKLTVL

SEQ ID NO: 54
EVQLLESGGGLVQPGGSLRLSCAASGFTFS<u>SYGMH</u>WVRQAPGKGLEWVA<u>AISYEGSTKFYADSVK</u>GRFTISRDNS
KNTLYLQMNSLRAEDTAVYYCAS<u>GVYYXGMDV</u>WGQGTLVTV
SEQ ID NO: 55
QSVLTQPPSASGTPGQRVTISC<u>SGSTSNIGNSHVY</u>WYQQLPGTAPKLLIY<u>NDNLRPS</u>GVPDRFSGSKSGTSASLAISG
LRSEDEADYYC<u>QSYDSSLIGWM</u>FGGGTKLKVL

FIGURE 7C

SEQ ID NO: 56
EVQLLESGGGLVQPGGSLRLSCAASGFTFS<u>SYSMN</u>WVRQAPGKGLEWVA<u>VISYDGSNKYYADSVK</u>GRFTISRDNS
KNTLYLQMNSLRAEDTAMYYCAR<u>LNRAGAFDI</u>WGQGTLVTV

SEQ ID NO: 57
QSVLTQPPSASGTPGQRVTISC<u>SGRSSNIGSNTVN</u>WYQQLPGTAPKLLIY<u>KNNQRPS</u>GVPDRFSGSKSGTSASLAISG
LRSEDEADYYC<u>AVWDGSLSGW</u>AFGGRTKLTVL

SEQ ID NO: 58
EVQLLESGGGLVQPGGSLRLSCAASGFTFS<u>SYGMH</u>WVRQAPGKGLEWVS<u>LISWDGGSTYYADSVK</u>GRFTISRDNS
KNTLYLQMNSLRAEDTAVYYCAR<u>GWFDP</u>WGQGTLVTV

SEQ ID NO: 59
QSVLTQPPSASGTPGQRVTISC<u>SGSSSNIGSNYVY</u>WYQQLPGTAPKLLIY<u>DNNKRPS</u>GVPDRFSGSKSGTSASLAISG
LRSEDEADYYC<u>AAWDGSLNGPV</u>FGGGTKLTVL

SEQ ID NO: 60
EVQLLESGGGLVQPGGSLRLSCAASGFTFR<u>NYAMS</u>WVRQAPGKGLEWVS<u>GVSWNGSRTHYADSVK</u>GRFTISRDN
SKNTLYLQMNSLRAEDTAVYYCTT<u>VSLY</u>WGQGTLVTV

SEQ ID NO: 61
QSVLTQPPSASGTPGQRVTISC<u>TGSSSNIGAGYDVH</u>WYQQLPGTAPKLLIY<u>DNNKRPS</u>GVPDRFSGSKSGTSASLAIS
GLRSEDEADYYC<u>QSYDSSLSRW</u>VFGGGTKLTVL

SEQ ID NO: 62
EVQLLESGGGLVQPGGSLRLSCAASGFTFS<u>SYAMH</u>WVRQAPGKGLEWVS<u>SISSSSSSIYYADSVK</u>GRFTISRDNSKN
TLYLQMNSLRAEDTAVYYCAR<u>GGGQQLGAFDI</u>WGQGTLVTV

SEQ ID NO: 63
QSVLTQPPSASGTPGQRVTISC<u>SGSSSNIGSNFVT</u>WYQQLPGTAPKLLIY<u>GNNNRPS</u>GVPDRFSGSKSGTSASLAISGL
RSEDEADYYC<u>AAWDGSLSGW</u>VFGGGTKLTVL

SEQ ID NO: 64
EVQLLESGGGLVQPGGSLRLSCAASGFTFD<u>DYGMS</u>WVRQAPGKGLEWVA<u>VISYDGSNKYYADSVK</u>GRFTISRDNS
KNTLYLQMNSLRAEDTAVYYCAT<u>AFTGPDAFDI</u>WGQGTLVTV

SEQ ID NO: 65
QSVLTQPPSASGTPGQRVTISC<u>SGSSSNIGSNAVN</u>WYQQLPGTAPKLLIY<u>TNTNRPS</u>GVPDRFSGSKSGTSASLAISGL
RSEDEADYYC<u>AAWDDSLNGW</u>VFGGGTKLTVL

SEQ ID NO: 66
EVQLLESGGGLVQPGGSLRLSCAASGFTFS<u>YYPMT</u>WVRQAPGKGLEWVA<u>VISYDASQTYYAEPVK</u>GRFTISRDNS
KNTLYLQMNSLRAEDTAVYYCAR<u>GTYGLLDY</u>WGQGTLVTV

SEQ ID NO: 67
QSVLTQPPSXSGTPGQRVTISC<u>SGSSSNIGNNYVS</u>WYXQLPGTAPKLLIY<u>DNNKRPS</u>GVPDRFSGSKSGTSASLAISG
LRSEDEADYYC<u>AAWDDSLSGV</u>FGGRTKLTVL

SEQ ID NO: 68
EVQLLESGGGLVQPGGSLRLSCAASGFTFS<u>NYGMH</u>WVRQAPGKGLEWVS<u>LISWDGGSTYYADSVK</u>GRFTISRDNS
KNTLYLQMNSLRAEDTAVYYCIG<u>SWFDP</u>WGQGTLVTV

SEQ ID NO: 69
QSVLTQPPSASGTPGQRVTISC<u>SGSSSNIGSNTVN</u>WYQQLPGTAPKLLIY<u>DNDRRPL</u>GVPDRFSGSKSGTSXSLAISG
LRSXDEADYYC<u>AAWDDSLSGV</u>VFGGGTKLTVL

SEQ ID NO: 70
EVQLLESGGGLVQPGGSLRLSCAASGFTFD<u>NYGMS</u>WVRQAPGKGLEWVA<u>VISYDGSNKYYADSVK</u>GRFTISRDNS
KNTLYLQMNSLRAEDTAVYYCAS<u>WLQVDAFDL</u>WGQGTLVTV

SEQ ID NO: 71
QSVLTQPPSASGTPGQRVTISC<u>SGSSSNIGSNYVY</u>WYQQLPGTAPKLLIY<u>GNSNRPS</u>GVPDRFSGSKSGTSASLAISGL
RSEDEADYYC<u>ATWDDSLNGW</u>VFGGGTKLTVL

SEQ ID NO: 72
EVQLLESGGGLVQPGGSLRLSCAASGFTFS<u>DYGMH</u>WVRQAPGKGLEWVA<u>LISFDGSKTNYGGPVQ</u>GRFTISRDNS
ENTLYLQMNSLRAEDTAVYYCTR<u>GAFDI</u>WGQGTLVTV

SEQ ID NO: 73
QSVLTQPPSASGTPGQRVTISC<u>SGSSSNIGSNYVY</u>WYQQLPGTAPKLLIY<u>DNNKRPS</u>GVPDRFSGSKSGTSASLAISG
LRSEDEADYYC<u>AAWDDSLKPV</u>FGGGTKLTVL

FIGURE 8

SEQ ID NO: 74
EVQLLESGGGLVQPGGSLRLSCAASGFTFS<u>NYGMH</u>WVRQAPGKGLEWVS<u>LISWDGGRTSYTDSVKGR</u>
FTISRDNSKNTLYLQMNSLRAEDTAVYYCAR<u>GLIGDN</u>WGQGTLVTVSS
SEQ ID NO: 75
QSVLTQPPSASGTPGQRVTISC<u>TGSSSNIGAGYDVH</u>WYQQLPGTAPKLLIY<u>DNNKRPS</u>GVPDRFSGSKS
GTSASLAISGLRSEDEADYYC<u>AAWDDSLNGWV</u>FGGGTKLTVL

FIGURE 9

XHA.06.983 LC variable region (SEQ ID NO: 76)
atgaagtcacagacccaggtcttcgtattctactgctctgtgtgtctggtgctcatgggagtattgtga
tgacccagactcccaaattcctgcttgtatcagcaggagacagggttaccataacctgcaaggccagtca
gggtgtgagtaatgatgtagcttggttccagcagaagccagggcagtctcctaaactgctgatatactct
gcatccactcgctacactggagtccctgatcgcctcactggcagtggatatgggacggatttcactttca
ccatcaacactgtgcaggctgaagacctggcagtttacttctgtcagcaggattatacctctccgacgtt
cggtggaggcaccaagctggaaatcaaacgggct

XHA.06.983 HC variable region (SEQ ID NO: 77)
atggactccaggctcaatttagtttccttgtccttatttaaaaggtgtccagtgtgacgtgcagctgg
tggagtctgggggaggcttggtgcagcctggagggtcccggaaactctcctgtgcagcctctggattcgc
tttcagtagtttggaatgcagtgggttcgtcaggctccagagaaggggctggagtgggtcgcatatatt
agtagtggcagtagtaccatctactatgcagacacagtgaagggccgattcaccatctccagagacaatc
ccaagaacaccctgttcctgcaaatgaccagtctaaggtctgaggacacggccatgtattactgtgtaag
atctgggagggactactggggtcaaggaacctcagtcaccgtcagctca

XHA.06.275 LC variable region (SEQ ID NO: 78)
atgaggttccaggttcaggttctgggggctccttctgctctggatatcaggtgcccagtgtgatgtccagataacccagtctccatcttatcttgct
gcatctcctggagaaaccattactcttaattgcagggcaagtaagaacatttacaaatatttagcctggtatcaagaaaaacctgggaaaact
aataaccttcttatctactctggatccactttgcattctggaattccatcaaggttcagtggcagtggatctggtacagatttcactctcaccatca
gtagcctggatcctgaagattttgcaatgtattactgtcaacagcataatgattacccgtacacgttcggaggggggaccaagctggagata
aaacgggct

XHA.06.275 HC variable region (SEQ ID NO: 79)
atgagagtgctgattctttgtggctgttcacagcctttcctggtatcctgtctgatgtgcagcttcaggagtcgggacctggcctggtgaagcc
ttctcagtctctgtccctcacctgcactgtcactggctactcaatcaccagtgattatgcctggaactggatccggcagtttccaggaaacaaa
ctggagtggatgggctacataagttacagtggtagtactagctacaacccatctctcaaaagtcgaatctctatcactcgagacacatccaag
aaccagttcttcctgcagttgaattctgtgactactgaggacacagccacatatttttgtgcaagagactacggctacgtctttgactactgggg
ccaaggcaccactctcacagtctcctca

XHA.06.642 LC variable region (SEQ ID NO: 80)
atggagacagacacactcctgttatgggtactgctgctctgggttccaggttccactggtgacattgtgctgacacagtctcctgcttccttag
ctgtatctctgggggcaggggggccaccatctcatgcagggccagcaaaagtgtcagtacatctggctatacttatatgcactggtaccaacag
aaaccaggacagccacccaaactcctcatctatcttgcatccaacctagaatctggggtccctgccaggttcagtggcagtgggtctggga
cagacttcaccctcaacatccatcctgtggaggaggaggatgctgcaacctattactgtcagcacagtggggagcttcctcccctcgttcgga
gggggaccaagctggaaataaaacgggct

XHA.06.642 HC variable region (SEQ ID NO: 81)
atgaacttcgggctcagcttgattttccttgccctcatttaaaaggtgtccagtgtgaggtgcagctggtggagtctgggggagacttagtga
agcctggagggtccctgaaactctcctgtgcagtctctggattcactttcagtagctatggcatgtcttgggttcgccagactccagacaaga
ggctggagtgggtcgcaaccgttagtagtggtggtacttacacctactatccagacagtgtgaaggggcgattcaccatctccagagacaa
tgccaagaacaccctgtacctgcaaatgagcagtctgaagtctgaggactcagccatgtattactgtgcaagacataggggaaactactatg
ctacttattactatgctatggactactggggtcaaggaacctcagtcaccgtctcctcg

FIGURE 10

XHA.06.983 VL (SEQ ID NO: 82)

SIVMTQTPKFLLVSAGDRVTITCKASQGVSNDVAWFQQKPGQSPKLLIYSASTRYTG
VPDRLTGSGYGTDFTFTINTVQAEDLAVYFCQQDYTSPTFGGGTKLEIKRA

XHA.06.983 VH (SEQ ID NO: 83)

DVQLVESGGGLVQPGGSRKLSCAASGFAFSSFGMQWVRQAPEKGLEWVAYISSGSS
TIYYADTVKGRFTISRDNPKNTLFLQMTSLRSEDTAMYYCVRSGRDYWGQGTSVTV
SS

XHA.06.275 VL (SEQ ID NO: 84)

DVQITQSPSYLAASPGETITLNCRASKNIYKYLAWYQEKPGKTNNLLIYSGSTLHSGIP
SRFSGSGSGTDFTLTISSLDPEDFAMYYCQQHNDYPYTFGGGTKLEIKRA

XHA.06.275 VH (SEQ ID NO: 85)

DVQLQESGPGLVKPSQSLSLTCTVTGYSITSDYAWNWIRQFPGNKLEWMGYISYSGS
TSYNPSLKSRISITRDTSKNQFFLQLNSVTTEDTATYFCARDYGYVFDYWGQGTTLTV
SS

XHA.06.642 VL (SEQ ID NO: 86)

DIVLTQSPASLAVSLGQGATISCRASKSVSTSGYTYMHWYQQKPGQPPKLLIYLASNL
ESGVPARFSGSGSGTDFTLNIHPVEEEDAATYYCQHSGELPPSFGGGTKLEIKRA

XHA.06.642 VH (SEQ ID NO: 87)

EVQLVESGGDLVKPGGSLKLSCAVSGFTFSSYGMSWVRQTPDKRLEWVATVSSGGT
YTYYPDSVKGRFTISRDNAKNTLYLQMSSLKSEDSAMYYCARHRGNYYATYYYAM
DYWGQGTSVTVSS

Figure 15
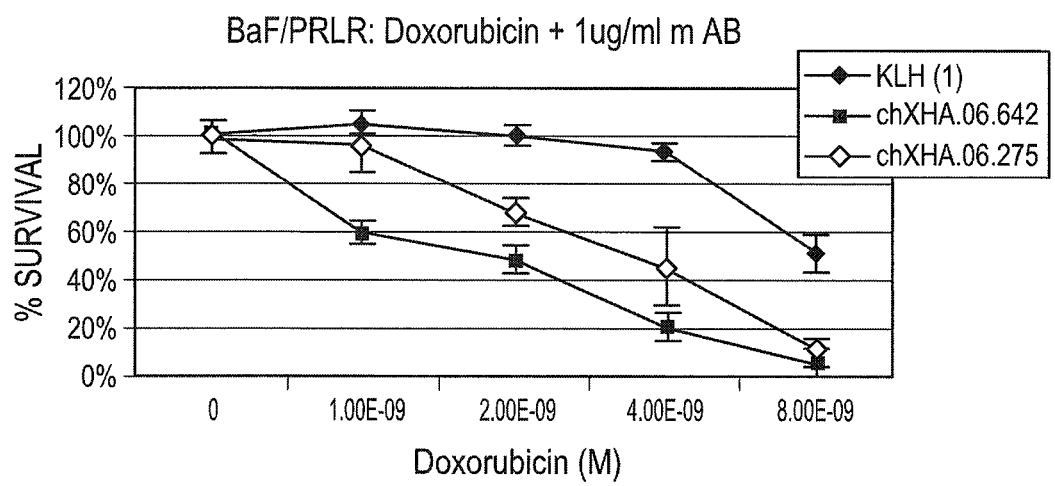
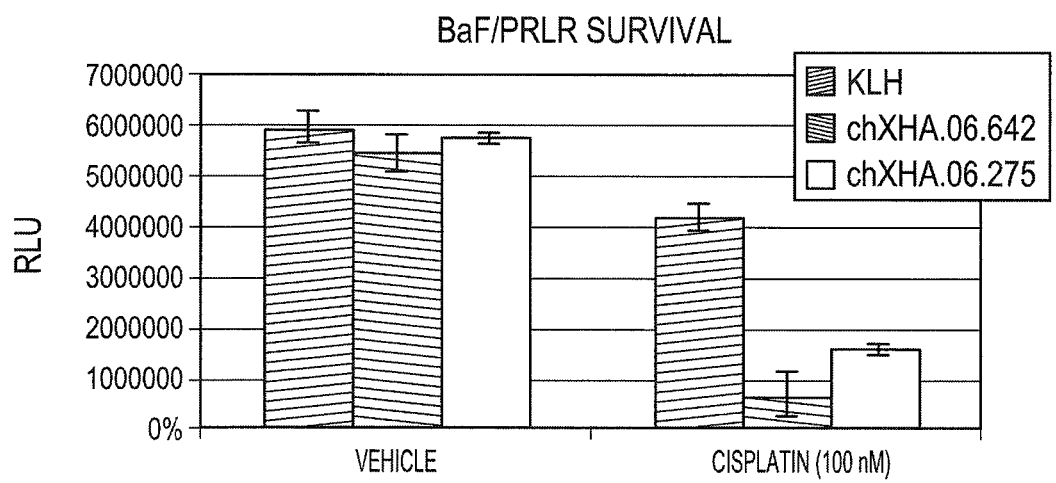

Figure 18
A.
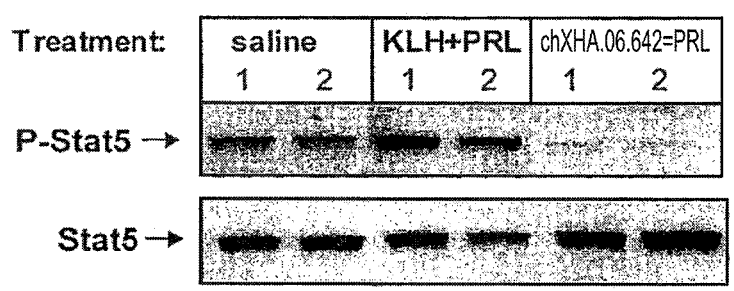
B.
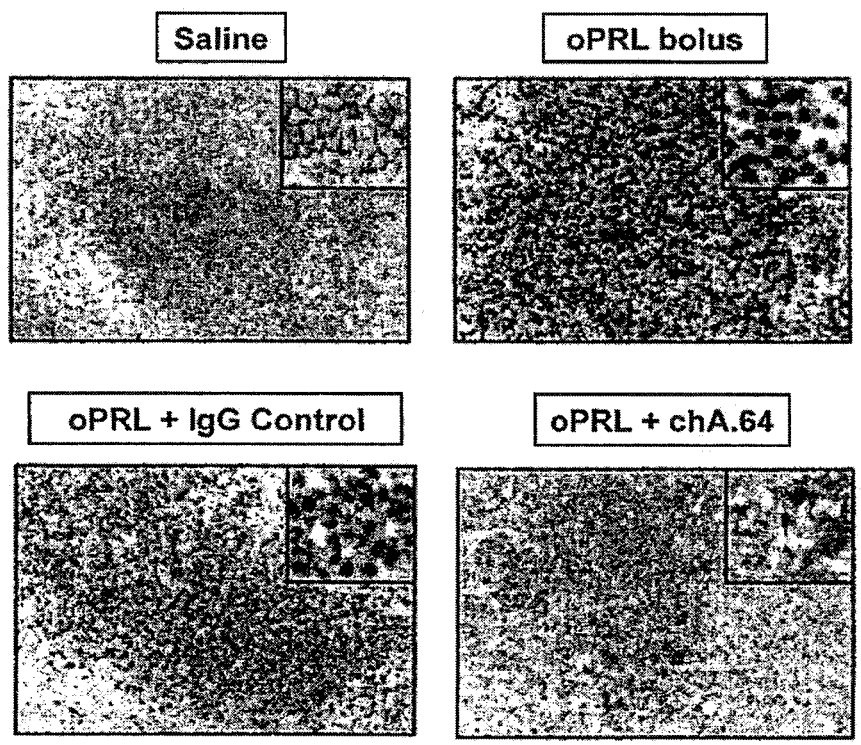

Figure 21
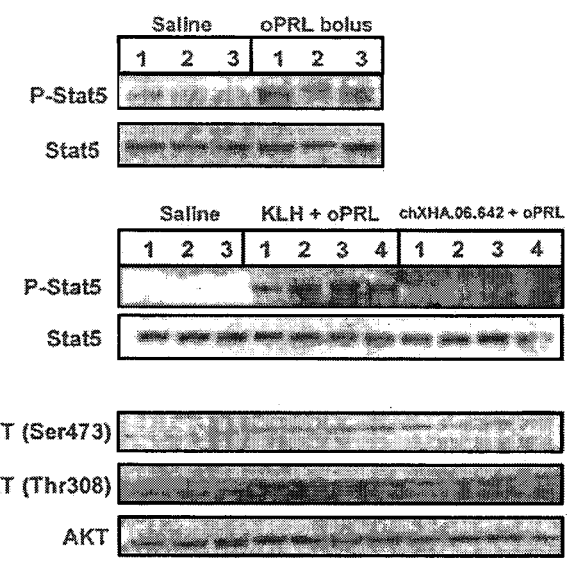
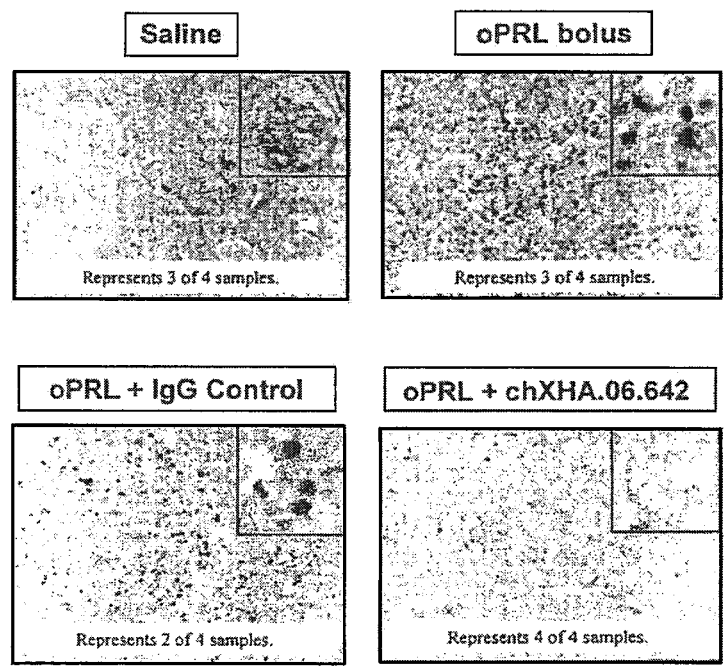

PRLR-SPECIFIC ANTIBODY AND USES THEREOF

CROSS-REFERENCE TO RELATED APPLICATIONS

This application is a divisional of U.S. patent application Ser. No. 11/840,267 filed Aug. 17, 2007 now U.S. Pat. No. 7,867,493 which claims priority to U.S. Provisional Patent Application No. 60/946,360 filed Jun. 26, 2007 and U.S. Provisional Patent Application No. 60/838,648 filed Aug. 18, 2006.

TECHNICAL FIELD

This invention relates to methods for preventing and treating cancer by administering PRLR-specific antibodies.

BACKGROUND OF THE INVENTION

Cancer is the second leading cause of death in the United States. Although "cancer" is used to describe many different types of cancer, i.e. breast, prostate, lung, colon, pancreas, each type of cancer differs both at the phenotypic level and the genetic level. The unregulated growth characteristic of cancer occurs when the expression of one or more genes becomes dysregulated due to mutations, and cell growth can no longer be controlled.

Genes are often classified in two classes, oncogenes and tumor suppressor genes. Oncogenes are genes whose normal function is to promote cell growth, but only under specific conditions. When an oncogene gains a mutation and then loses that control, it promotes growth under all conditions. However, it has been found that for cancer to be truly successful the cancer must also acquire mutations in tumor suppressor genes. The normal function of tumor suppressor genes is to stop cellular growth. Examples of tumor suppressors include p53, p16, p21, and APC, all of which, when acting normally, stop a cell from dividing and growing uncontrollably. When a tumor suppressor is mutated or lost, that brake on cellular growth is also lost, allowing cells to now grow without restraints.

Prolactin receptor (PRLR) is a single membrane-spanning class 1 cytokine receptor that is homologous to receptors for members of the cytokine superfamily, such as the receptors for IL2, IL3, IL4, IL6, IL7, erythropoietin, and GM-CSF. PRLR is involved in multiple biological functions, including cell growth, differentiation, development, lactation and reproduction. It has no intrinsic tyrosine kinase activity; ligand binding leads to receptor dimerization, cross-phosphorylation of Jak2 and downstream signaling. Human prolactin receptor cDNA was originally isolated from hepatoma and breast cancer libraries (Boutin, J.-M. et al., Molec. Endocr. 3: 1455-1461, 1989). The nucleotide sequence predicted a mature protein of 598 amino acids with a much longer cytoplasmic domain than the rat liver PRL receptor. The prolactin receptor gene resides in the same chromosomal region as the growth hormone receptor gene, which has been mapped to 5; 13-p12 (Arden, K. C. et al. Cytogenet. Cell Gene 53: 161-165, 1990; Arden, K. C. et al., (Abstract) AM. J. Hum. Genet. 45 (suppl.): A129 only, 1989). Growth hormone also binds to the prolactin receptor and activates the receptor.

The genomic organization of the human PRLR gene has been determined (Hu, Z.-Z. et al., J. Clin. Endocr. Metab. 84: 1153-1156, 1999). The 5-prime-untranslated region of the PRLR gene contains 2 alternative first exons: E13, the human counterpart of the rat and mouse E13, and a novel human type of alternative first exon termed E1N. The 5-prime-untranslated region also contains a common noncoding exon 2 and part of exon 3, which contains the translation initiation codon. The E13 and E1N exons are within 800 basepairs of each other. These 2 exons are expressed in human breast tissue, breast cancer cells, gonads, and liver. Overall, the transcript containing E13 is prevalent in most tissues. The PRLR gene product is encoded by exons 3-10, of which exon 10 encodes most of the intracellular domain. The E13 and E1N exons are transcribed from alternative promoters PIII and PN, respectively. The PIII promoter contains Sp1 and C/EBP elements that are identical to those in the rodent promoter and is 81% similar to the region-480/-106 in the rat and mouse. The PN promoter contains putative binding sites for ETS family proteins and a half-site for nuclear receptors.

PRLR exists in a number of different isoforms that differ in the length of their cytoplasmic domains. Four PRLR mRNA isoforms (L, I, S1a, and S1b) have been demonstrated in human subcutaneous abdominal adipose tissue and breast adipose tissue (Ling, C. et al., J. Clin. Endocr. Metab. 88: 1804-1808, 2003). In addition, they detected L-PRLR and I-PRLR protein expression in human subcutaneous abdominal adipose tissue and breast adipose tissue using immunoblot analysis. PRL reduced the lipoprotein lipase activity in human adipose tissue compared with control. Ling et al. suggest that these results demonstrated a direct effect of PRL, via functional PRLRs, in reducing the LPL activity in human adipose tissue, and that these results suggested that LPL might also be regulated in this fashion during lactation. The function of these PRLR isoforms in rat has been elucidated (Perrot-Applanat, M. et al., Molec. Endocr. 11: 1020-1032, 1997). Like the known long form (591 amino acids), the Nb2 form, which lacks 198 amino acids of the cytoplasmic domain, is able to transmit a lactogenic signal. In contrast, the short form, which lacks 291 amino acids of the cytoplasmic domain, is inactive. The function of the short form was examined after cotransfection of both the long and short forms. These results show that the short form acts as a dominant-negative inhibitor through the formation of inactive heterodimers, resulting in the inhibition of Janus kinase 2 activation. Perrot-Applanat et al. suggest that heterodimerization of PRLR can positively or negatively activate PRL transcription.

Recent reports have suggested that PRLR is over-expressed in human breast cancer and prostate cancer tissues (Li et al., Cancer Res., 64:4774-4782, 2004; Gill et al., J Clin Pathol., 54:956-960, 2001; Touraine et al., J Clin Endocrinol Metab., 83:667-674, 1998). Li et al., reported that Stat5 activation and PRLR expression is associated with high histological grade in 54% of prostate cancer specimens (Li et al., supra). Other reports have suggested that primary breast cancer specimens are responsive to PRL in colony formation assays and that plasma PRL concentrations correlate with breast cancer risk (Tworoger et al., Cancer Res., 64:6814-6819, 2004; Tworoger et al., Cancer Res., 66:2476-2482, 2006). Another report indicated that PRL transgenic mice develop malignant mammary carcinomas or prostate hyperplasia (Wennbo et al., J Clin Invest., 100:2744-2751, 1997; Wennbo et al., Endocrinology, 138:4410-4415, 1997).

A PRLR monoclonal antibody diminished the incidence of mammary tumors in mice (Sissom et al., Am. J. Pathol. 133: 589-595, 1988). In addition, a PRL antagonist (S179D mutant PRL) inhibited proliferation of a human prostate carcinoma cell line, DU-145, in vitro and DU-145 induced tumors in vivo (Xu et al., Cancer Res., 61:6098-6104, 2001).

Thus, there is a need to identify compositions and methods that modulate PRLR and its role in such cancers. The present invention is directed to these, as well as other, important needs.

SUMMARY OF THE INVENTION

The nucleotide sequence for PRLR is set out in SEQ ID NO: 1, and the amino acid sequence is set out in SEQ ID NO: 2. The extracellular domain (ECD) consists of amino acids 25 through 234 of SEQ ID NO: 2, which can be divided into two major domains, S1 (amino acids 25-122) and S2 (amino acids 123-234). A number of different isoforms of PRLR have been identified: long (L), intermediate (I), ΔS1, an inactive soluble form (PRLBP), and inactive short forms S1a and S1b. The exons and nucleotide regions contained within each isoform are displayed in FIG. 1. In exemplary embodiments, the invention contemplates antibodies that bind to the S1 domain and/or to the S2 domain. Such antibodies that bind to the S2 domain may target all active isoforms. The invention also contemplates antibodies that bind specifically to one isoform and not another (e.g. intermediate and not S1a or S1b), or to the active isoforms (long, intermediate and ΔS1) but not to the inactive isoforms (S1a and S1b).

The materials and methods of the present invention fulfill the aforementioned and other related needs in the art.

In one embodiment, an antibody that binds the extracellular domain of PRLR with an equilibrium dissociation constant ($K_D$) of $10^{-6}$ M or lower and competes with any of antibodies chXHA.06.642, chXHA.06.275, he.06.642-1, he.06.642-2, he.06.275-1, he.06.275-2, he.06.275-3, he.06.275-4, XPA.06.128, XPA.06.129, XPA.06.130, XPA.06.131, XPA.06.141, XPA.06.147, XPA.06.148, XPA.06.158, XPA.06.159, XPA.06.163, XPA.06.167, XPA.06.171, XPA.06.178, XPA.06.181, XPA.06.192, XPA.06.202, XPA.06.203, XPA.06.206, XPA.06.207, XPA.06.210, XPA.06.212, XPA.06.217, XPA.06.219, XPA.06.229, XPA.06.233, XPA.06.235, XPA.06.239, XPA.06.145, XHA.06.567, XHA.06.642, XHA.06.983, XHA.06.275, XHA.06.189, or XHA.06.907 for binding to PRLR by more than 75% is provided. By the term "an equilibrium dissociation constant ($K_D$) of $10^{-6}$M or lower" it is meant an equilibrium dissociation constant of, e.g., $10^{-6}$, $10^{-7}$ M, $10^{-8}$ M, $10^{-9}$ M, $10^{-10}$ M, $10^{-11}$ M or $10^{-12}$ M (i.e., a number lower than $10^{-6}$ M). In another embodiment, the antibody binds to the same epitope of PRLR as any of antibodies chXHA.06.642, chXHA.06.275, he.06.642-1, he.06.642-2, he.06.275-1, he.06.275-2, he.06.275-3, he.06.275-4, XPA.06.128, XPA.06.129, XPA.06.130, XPA.06.131, XPA.06.141, XPA.06.147, XPA.06.148, XPA.06.158, XPA.06.159, XPA.06.163, XPA.06.167, XPA.06.171, XPA.06.178, XPA.06.181, XPA.06.192, XPA.06.202, XPA.06.203, XPA.06.206, XPA.06.207, XPA.06.210, XPA.06.212, XPA.06.217, XPA.06.219, XPA.06.229, XPA.06.233, XPA.06.235, XPA.06.239, XPA.06.145, XHA.06.567, XHA.06.642, XHA.06.983, XHA.06.275, XHA.06.189, or XHA.06.907.

In another embodiment, an aforementioned antibody comprises 1, 2, 3, 4, 5 or 6 CDRs of any of antibodies chXHA.06.642, chXHA.06.275, he.06.642-1, he.06.642-2, he.06.275-1, he.06.275-2, he.06.275-3, he.06.275-4, XPA.06.128, XPA.06.129, XPA.06.130, XPA.06.131, XPA.06.141, XPA.06.147, XPA.06.148, XPA.06.158, XPA.06.159, XPA.06.163, XPA.06.167, XPA.06.171, XPA.06.178, XPA.06.181, XPA.06.192, XPA.06.202, XPA.06.203, XPA.06.206, XPA.06.207, XPA.06.210, XPA.06.212, XPA.06.217, XPA.06.219, XPA.06.229, XPA.06.233, XPA.06.235, XPA.06.239, XPA.06.145, XHA.06.567, XHA.06.642, XHA.06.983, XHA.06.275, XHA.06.189, or XHA.06.907. In another embodiment, an aforementioned antibody is a chimeric antibody, a humanized antibody, a human engineered antibody, a human antibody, a single chain antibody or an antibody fragment. In yet another embodiment, an aforementioned antibody is provided in which at least one amino acid within a CDR is substituted by a corresponding residue of a corresponding CDR of another anti-PRLR antibody. In an exemplary embodiment, an aforementioned antibody is provided in which at least one amino acid within a CDR from an antibody selected from the group consisting of chXHA.06.642, chXHA.06.275, he.06.642-1, he.06.642-2, he.06.275-1, he.06.275-2, he.06.275-3, he.06.275-4, XPA.06.128, XPA.06.129, XPA.06.130, XPA.06.131, XPA.06.141, XPA.06.147, XPA.06.148, XPA.06.158, XPA.06.159, XPA.06.163, XPA.06.167, XPA.06.171, XPA.06.178, XPA.06.181, XPA.06.192, XPA.06.202, XPA.06.203, XPA.06.206, XPA.06.207, XPA.06.210, XPA.06.212, XPA.06.217, XPA.06.219, XPA.06.229, XPA.06.233, XPA.06.235, XPA.06.239, XPA.06.145, XHA.06.567, XHA.06.642, XHA.06.983, XHA.06.275, XHA.06.189, or XHA.06.907 is substituted by a corresponding residue of a corresponding CDR of another anti-PRLR antibody. In another exemplary embodiment, an aforementioned antibody is provided in which at least one amino acid within a CDR from an antibody selected from the group consisting of chXHA.06.642, chXHA.06.275, he.06.642-1, he.06.642-2, he.06.275-1, he.06.275-2, he.06.275-3, he.06.275-4, XPA.06.128, XPA.06.129, XPA.06.130, XPA.06.131, XPA.06.141, XPA.06.147, XPA.06.148, XPA.06.158, XPA.06.159, XPA.06.163, XPA.06.167, XPA.06.171, XPA.06.178, XPA.06.181, XPA.06.192, XPA.06.202, XPA.06.203, XPA.06.206, XPA.06.207, XPA.06.210, XPA.06.212, XPA.06.217, XPA.06.219, XPA.06.229, XPA.06.233, XPA.06.235, XPA.06.239, XPA.06.145, XHA.06.567, XHA.06.642, XHA.06.983, XHA.06.275, XHA.06.189, or XHA.06.907 is substituted by a corresponding residue of a corresponding CDR of another antibody selected from the group consisting of chXHA.06.642, chXHA.06.275, he.06.642-1, he.06.642-2, he.06.275-1, he.06.275-2, he.06.275-3, he.06.275-4, XPA.06.128, XPA.06.129, XPA.06.130, XPA.06.131, XPA.06.141, XPA.06.147, XPA.06.148, XPA.06.158, XPA.06.159, XPA.06.163, XPA.06.167, XPA.06.171, XPA.06.178, XPA.06.181, XPA.06.192, XPA.06.202, XPA.06.203, XPA.06.206, XPA.06.207, XPA.06.210, XPA.06.212, XPA.06.217, XPA.06.219, XPA.06.229, XPA.06.233, XPA.06.235, XPA.06.239, XPA.06.145, XHA.06.567, XHA.06.642, XHA.06.983, XHA.06.275, XHA.06.189, or XHA.06.907. In still another embodiment, an aforementioned antibody is provided in which one or two amino acids within a CDR have been modified.

In another embodiment of the invention, an aforementioned antibody is provided that retains at least 60, 65, 70, 75, 80, 85, 90, 91, 92, 93, 94, 95, 96, 97, 98, or 99% identity over either the variable light or heavy region to the antibodies of chXHA.06.642, chXHA.06.275, he.06.642-1, he.06.642-2, he.06.275-1, he.06.275-2, he.06.275-3, he.06.275-4, XPA.06.128, XPA.06.129, XPA.06.130, XPA.06.131, XPA.06.141, XPA.06.147, XPA.06.148, XPA.06.158, XPA.06.159, XPA.06.163, XPA.06.167, XPA.06.171, XPA.06.178, XPA.06.181, XPA.06.192, XPA.06.202, XPA.06.203, XPA.06.206, XPA.06.207, XPA.06.210, XPA.06.212, XPA.06.217, XPA.06.219, XPA.06.229, XPA.06.233, XPA.06.235, XPA.06.239, XPA.06.145, XHA.06.567, XHA.06.642, XHA.06.983, XHA.06.275, XHA.06.189, or XHA.06.907.

In another embodiment, an aforementioned antibody comprises a constant region of a human antibody sequence and one or more heavy and light chain variable framework regions of a human antibody sequence. In yet another embodiment of the invention, an aforementioned antibody is provided wherein the human antibody sequence is an individual human sequence, a human consensus sequence, an individual human germline sequence, or a human consensus germline sequence.

In still another embodiment, an aforementioned antibody is provided wherein the heavy chain constant region is a modified or unmodified IgG, IgM, IgA, IgD, IgE, a fragment thereof, or combinations thereof. In another embodiment, an aforementioned antibody is provided wherein the heavy chain constant region is a modified or unmodified IgG1, IgG2, IgG3 or IgG4. In another embodiment, an aforementioned antibody is provided that has an equilibrium dissociation constant of $10^{-6}$, $10^{-7}$, $10^{-8}$ or $10^{-9}$ M or lower to PRLR. In yet another embodiment, an aforementioned antibody is provided comprising a conservative substitution in the CDRs. In another embodiment, an aforementioned antibody is provided comprising a conservative or non-conservative change in low and moderate risk residues. In still another embodiment, an aforementioned antibody is provided wherein the light chain constant region is a modified or unmodified lambda light chain constant region, a kappa light chain constant region, a fragment thereof, or combinations thereof.

In yet another embodiment, an aforementioned antibody is provided that inhibits PRLR dimerization, inhibits PRLR intracellular phosphorylation, inhibits the induction of MAPK phosphorylation, inhibits the induction of Stat5 phosphorylation, inhibits the induction of AKT phosphorylation, and/or inhibits the binding of PRL to PRLR.

In other embodiments, an aforementioned antibody further inhibits VEGF production and/or angiogenesis.

In yet another embodiment, an aforementioned antibody is provided that inhibits the proliferation of a cancer cell. In yet another embodiment, the antibody inhibits proliferation of a breast, prostate, or lung cancer cell.

In addition to cancer, another embodiment of the invention provides an aforementioned antibody for the prevention and/or treatment of autoimmune and inflammatory diseases or disorders. The antibodies are especially useful in preventing, ameloriating, or treating diseases comprising an autoimmune and/or inflammatory component. These diseases include, but are not limited to, autoimmune and inflammatory diseases such as systemic lupus erythematosus (SLE), discoid lupus, lupus nephritis, sarcoidosis, inflammatory arthritis, including, but not limited to, juvenile arthritis, rheumatoid arthritis, psoriatic arthritis, Reiter's syndrome, ankylosing spondylitis, and gouty arthritis, rejection of an organ or tissue transplant, hyperacute, acute, or chronic rejection and/or graft versus host disease, multiple sclerosis, hyper IgE syndrome, polyarteritis nodosa, primary biliary cirrhosis, inflammatory bowel disease, Crohn's disease, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hashimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, Type I and Type II diabetes mellitus, type 1, 2, 3 and 4 delayed-type hypersensitivity, allergy or allergic disorders, unwanted/unintended immune responses to therapeutic proteins, asthma, Churg-Strauss syndrome (allergic granulomatosis), atopic dermatitis, allergic and irritant contact dermatitis, urtecaria, IgE-mediated allergy, atherosclerosis, vasculitis, idiopathic inflammatory myopathies, hemolytic disease, Alzheimer's disease, chronic inflammatory demyelinating polyneuropathy, and the like.

In another embodiment, an aforementioned antibody is provided that is conjugated to another diagnostic or therapeutic agent.

In still another embodiment, a method of screening for an antibody to the extracellular domain of a PRLR protein useful for the treatment of cancer is provided comprising the steps of: contacting a polypeptide comprising the ECD of PRLR with a candidate antibody that contains at least 1, 2, 3, 4, 5, or 6 CDRs of antibodies chXHA.06.642, chXHA.06.275, he.06.642-1, he.06.642-2, he.06.275-1, he.06.275-2, he.06.275-3, he.06.275-4, XPA.06.128, XPA.06.129, XPA.06.130, XPA.06.131, XPA.06.141, XPA.06.147, XPA.06.148, XPA.06.158, XPA.06.159, XPA.06.163, XPA.06.167, XPA.06.171, XPA.06.178, XPA.06.181, XPA.06.192, XPA.06.202, XPA.06.203, XPA.06.206, XPA.06.207, XPA.06.210, XPA.06.212, XPA.06.217, XPA.06.219, XPA.06.229, XPA.06.233, XPA.06.235, XPA.06.239, XPA.06.145, XHA.06.567, XHA.06.642, XHA.06.983, XHA.06.275, XHA.06.189, and XHA.06.907; detecting binding affinity of the candidate antibody to the polypeptide, and identifying said candidate antibody as an antibody useful for the treatment of cancer if an equilibrium dissociation constant of $10^{-6}$ M or lower is detected.

In another embodiment, a method of systematically altering antibodies and screening for an antibody to the extracellular domain of a PRLR protein useful for the treatment of cancer is provided comprising the steps of preparing a candidate antibody that contains modifications to one or two amino acids within the CDRs of antibodies chXHA.06.642, chXHA.06.275, he.06.642-1, he.06.642-2, he.06.275-1, he.06.275-2, he.06.275-3, he.06.275-4, XPA.06.128, XPA.06.129, XPA.06.130, XPA.06.131, XPA.06.141, XPA.06.147, XPA.06.148, XPA.06.158, XPA.06.159, XPA.06.163, XPA.06.167, XPA.06.171, XPA.06.178, XPA.06.181, XPA.06.192, XPA.06.202, XPA.06.203, XPA.06.206, XPA.06.207, XPA.06.210, XPA.06.212, XPA.06.217, XPA.06.219, XPA.06.229, XPA.06.233, XPA.06.235, XPA.06.239, XPA.06.145, XHA.06.567, XHA.06.642, XHA.06.983, XHA.06.275, XHA.06.189, and XHA.06.907; contacting a polypeptide comprising the ECD of PRLR with said candidate antibody; detecting binding affinity of the candidate antibody to the polypeptide; and identifying said candidate antibody as an antibody useful for the treatment of cancer if an equilibrium dissociation constant of $10^{-6}$ M or lower is detected.

In still another embodiment, a method of screening for an antibody to the extracellular domain of a PRLR protein useful for the treatment of cancer comprising the steps of contacting a breast, lung, or prostate cell with a candidate antibody that contains at least 1, 2, 3, 4, 5 or 6 CDRs of antibodies chXHA.06.642, chXHA.06.275, he.06.642-1, he.06.642-2, he.06.275-1, he.06.275-2, he.06.275-3, he.06.275-4, XPA.06.128, XPA.06.129, XPA.06.130, XPA.06.131, XPA.06.141, XPA.06.147, XPA.06.148, XPA.06.158, XPA.06.159, XPA.06.163, XPA.06.167, XPA.06.171, XPA.06.178, XPA.06.181, XPA.06.192, XPA.06.202, XPA.06.203, XPA.06.206, XPA.06.207, XPA.06.210, XPA.06.212, XPA.06.217, XPA.06.219, XPA.06.229, XPA.06.233, XPA.06.235, XPA.06.239, XPA.06.145, XHA.06.567, XHA.06.642, XHA.06.983, XHA.06.275, XHA.06.189, and XHA.06.907 or an antibody that contains a modification of one or two amino acids within one or more CDRs; detecting proliferation or survival of said cell; and identifying said candidate antibody as an antibody useful for the treatment of cancer if a decrease in cell proliferation or survival is detected.

In still another embodiment, a method of treating a subject suffering from cancer, including a subject suffering from stage 0, I, II, III, IV or V cancer, comprising the step of administering an aforementioned antibody in a therapeutically effective amount. In a related embodiment, the cancer is breast, lung or prostate cancer. In another embodiment, a second therapeutic agent is administered. In an exemplary embodiment, the second therapeutic agent is doxorubicin, daunorubicin, or other anthracycline or topoisomerase inhibitor. In further embodiments, any of the foregoing topoisomerase inhibitors are administered with chXHA.06.642, chXHA.06.275, he.06.642-1, he.06.642-2, he.06.275-1, he.06.275-2, he.06.275-3, he.06.275-4. In still another embodiment, the subject is further treated with radiation therapy or surgery. In still another embodiment of the invention, the subject is positive for PRLR expression and HER2-neu expression, and wherein said second therapeutic agent is an anti-Her2-neu antibody. In a related embodiment, the subject is positive for PRLR expression and ER expression, and wherein said second therapeutic agent is an anti-ER antibody. In a further embodiment, the invention provides an antibody of the invention for use in medicine, including for use in treating a cancer. In other embodiments, the invention provides the use of an antibody of the invention in the manufacture of a medicament for treating a cancer. The medicament may be administered to a patient in combination with a second therapeutic agent, and/or with radiation therapy.

In another embodiment of the invention, a method of targeting a tumor cell expressing PRLR is provided comprising the step of administering an aforementioned antibody conjugated to a radionuclide or other toxin. In another embodiment, the subject is a mammal. In still another embodiment, the subject is a human.

In still another embodiment, an isolated nucleic acid molecule is provided comprising a nucleotide sequence that encodes the heavy chain or light chain of an aforementioned antibody. In still another embodiment, an expression vector comprising the aforementioned nucleic acid molecule operably linked to a regulatory control sequence is provided. In yet another embodiment, a host cell comprising the aforementioned vector or the aforementioned nucleic acid molecule is provided.

In still another embodiment, a method of using the aforementioned host cell to produce an antibody, comprising culturing the host cell under suitable conditions and recovering said antibody is provided. In still another embodiment, the antibody produced by the aforementioned method is provided.

In still another embodiment, an aforementioned antibody that is purified to at least 95% homogeneity by weight is provided. In another embodiment, a pharmaceutical composition comprising the aforementioned antibody and a pharmaceutically acceptable carrier is provided.

In yet another embodiment, a kit comprising an aforementioned antibody comprising a therapeutically effective amount of an antibody of the invention, packaged in a container, the kit optionally containing a second therapeutic agent, and further comprising a label attached to or packaged with the container, the label describing the contents of the container and providing indications and/or instructions regarding use of the contents of the container to treat cancer, is provided. In another embodiment, the kit is provided wherein the container is a vial or bottle or prefilled syringe.

In another embodiment of the invention, an antibody that binds the extracellular domain of PRLR comprising a variable light chain amino acid sequence selected from the group consisting of SEQ ID NO: 21, 23, 25, 27, 29, 31, 33, 35, 37, 39, 41, 43, 45, 47, 49, 51, 53, 55, 57, 59, 61, 63, 65, 67, 69, 71, 73, 75, 82, 84, 86, 88, 91, 95 and 96, is provided. In another embodiment, an antibody that binds the extracellular domain of PRLR is provided comprising a variable heavy chain amino acid sequence selected from the group consisting of SEQ ID NO: 20, 2, 24, 26, 28, 30, 32, 34, 36, 38, 40, 42, 44, 46, 48, 50, 52, 54, 56, 58, 60, 62, 64, 66, 68, 70, 72, 74, 83, 85, 87, 89, 90, 93, 94, 97 and 98. In yet another embodiment, an antibody that binds the extracellular domain of PRLR comprising a variable light chain amino acid sequence SEQ ID NO: 88, and a variable heavy chain amino acid sequence of SEQ ID NO: 89, is provided. In still another embodiment, an antibody that binds the extracellular domain of PRLR comprising a variable light chain amino acid sequence SEQ ID NO: 88, and a variable heavy chain amino acid sequence of SEQ ID NO: 90 is provided.

In yet another embodiment of the invention, an antibody is provided that binds the extracellular domain of PRLR comprising a variable light chain amino acid sequence of SEQ ID NO: 91, and a variable heavy chain amino acid sequence of SEQ ID NO: 93. In another embodiment, an antibody that binds the extracellular domain of PRLR comprising a variable light chain amino acid sequence of SEQ ID NO: 91, and a variable heavy chain amino acid sequence of SEQ ID NO: 94 is provided. In still another embodiment, an antibody that binds the extracellular domain of PRLR comprising a variable light chain amino acid sequence of SEQ ID NO: 92, and a variable heavy chain amino acid sequence of SEQ ID NO: 93. In yet another embodiment of the invention, an antibody that binds the extracellular domain of PRLR is provided comprising a variable light chain amino acid sequence of SEQ ID NO: 92, and a variable heavy chain amino acid sequence of SEQ ID NO: 94.

In still another embodiment of the invention, an antibody that binds the extracellular domain of PRLR is provided comprising a variable light chain amino acid sequence of SEQ ID NO: 95, and a variable heavy chain amino acid sequence of SEQ ID NO: 97. In another embodiment, an antibody that binds the extracellular domain of PRLR comprising a variable light chain amino acid sequence of SEQ ID NO: 95, and a variable heavy chain amino acid sequence of SEQ ID NO: 98 is provided. In yet another embodiment, an antibody that binds the extracellular domain of PRLR comprising a variable light chain amino acid sequence of SEQ ID NO: 96, and a variable heavy chain amino acid sequence of SEQ ID NO: 97 is provided. In another embodiment, an antibody that binds the extracellular domain of PRLR is provided comprising a variable light chain amino acid sequence of SEQ ID NO: 96, and a variable heavy chain amino acid sequence of SEQ ID NO: 98.

In another embodiment of the invention, an antibody that binds the extracellular domain of human PRLR with a KD of at least 10 to 25,000 fold, 100 to 20,000 fold, 1,000 to 18,000 fold, 5,000 to 17,000 fold, 8,000 to 16,000 fold, 10,000 to 15,000 fold, 12,000 to 15,000 fold, or 13,000 to 14,000 fold, fold lower than the extracellular domain of murine PRLR is provided. In a related embodiment, the aforementioned antibody binds the same epitope as he.06.275-4. In still another embodiment, an antibody that binds the extracellular domain of human PRLR, the extracellular domain of murine PRLR, and the extracellular domain of rat PRLR is provided. In another embodiment, an antibody that binds the extracellular domain of human, murine and rat PRLR with an equilibrium dissociation constant ($K_D$) of $10^{-6}$ M or lower is provided. In a related embodiment, the aforementioned antibody binds the same epitope as he.06.642-2.

In still another embodiment, the above methods can be used to identify a subject in need of treatment with an anti-PRLR antibody by, for example, (a) obtaining a sample from the subject; and (b) analyzing the sample for level of phosphorylation of PRLR, Jak2, Mapk, Stat5, Erk1/2 and/or Akt; wherein the level of phosphorylation of PRLR, Jak2, Mapk, Stat5, Erk1/2 and/or Akt is indicative of a need for treatment with an anti-PRLR antibody. In another embodiment, a method of monitoring cancer therapy in a subject afflicted with cancer is provided comprising the steps of: (a) analyzing a first sample from the subject for level of phosphorylation of PRLR prior to the initiation of treatment with a cancer therapeutic; and (b) analyzing a second sample after the initiation of the treatment with the cancer therapeutic, wherein a reduction in the level of phosphorylated PRLR after the initiation of the treatment with the cancer therapeutic indicates the patient is receiving a therapeutically effective dose of the cancer therapeutic. In a related embodiment, the cancer therapeutic is an antibody according to any one of the above described embodiments.

BRIEF DESCRIPTION OF THE DRAWINGS

FIGS. 2, 3 and 4 show effect of selected PRLR-specific antibodies on pERK1/2 phosphorylation. [mAb 1167 is a control murine anti-PRLR monoclonal antibody; R&D Systems, catalog #MAB 1167]

FIG. 5 shows the effect of PRLR-specific antibody on proliferation of a PRL-responsive tumor cell line.

FIG. 6 shows the effect of PRLR-specific antibody on PRLR intracellular phosphorylation.

FIG. 7A-7C shows the VH and VL amino acid sequences, as well as the location of the CDRs (underlined), of antibodies XPA.06.128, XPA.06.129, XPA.06.130, XPA.06.131, XPA.06.141, XPA.06.147, XPA.06.148, XPA.06.158, XPA.06.159, XPA.06.163, XPA.06.167, XPA.06.171, XPA.06.178, XPA.06.181, XPA.06.192, XPA.06.202, XPA.06.203, XPA.06.206, XPA.06.207, XPA.06.210, XPA.06.212, XPA.06.217, XPA.06.219, XPA.06.229, XPA.06.233, XPA.06.235, XPA.06.239 which had greater than 80% inhibition in the pERK assay.

FIG. 8 shows the VH and VL amino acid sequence of antibody XPA.06.145.

FIG. 9 shows the leader and VH and VL nucleotide sequences of antibodies XHA.06.983, XHA.06.275, and XHA.06.642.

FIG. 10 shows the VH and VL amino acid sequences of antibodies XHA.06.983, XHA.06.275, and XHA.06.642 (CDRs underlined).

FIG. 15 shows Anti-PRLR mAbs synergize with cytotoxic drugs in combination studies. Doxorubicin (top panel) and Cisplatin (bottom panel) were co-administered with anti-KLH control Ab, anti-PRLR mAb chXHA.06.642, or anti-PRLR mAb chXHA.06.275 (all at 1 ug/ml). Cell survival was determined by CellTiter Glo analysis and is reported aS RLU (y-axis).

FIGS. 18A and B show inhibition of p-STAT5 in Nb2-C11 tumors of chXHA.06.642 treated animals. Athymic mice with subcutaneous Nb2-c11 tumors were injected intraperitoneally with chXHA.06.642 or KLH control IgG1 mAb. Two days later a 20 ug bolus intraperitoneal injection of oPRL was administered. Control animals were injected with saline. Two days later a 20 ug bolus injection of oPRL was administered intraperitoneally, and 40 minutes later tumors were collected and evaluated for p-STAT5 by immunoblot or IHC. FIG. 18A, Western blot of 80 ug of Tyr694 p-STAT5; FIG. 18B, IHC of Tyr694 p-STAT5.

FIG. 20A displays tumor volume.

FIGS. 21A and B show intraperitoneal bolus injection of oPRL induces p-STAT5, and treatment with chA64.1 inhibits p-STAT5 induction in T47D human breast xenografts. chXHA.06.642 or KLH control IgG1 were injected intraperitoneally into T47D tumor bearing immunocompromised mice implanted with 0.18 mg/day estradiol ($E_2$) pellets to support growth. Two days later a 20 ug bolus injection of oPRL was administered intraperitoneally, and 40 minutes later T47D tumors were collected and evaluated for p-STAT5 by immunoblot or IHC. p-ERK or p-AKT levels were also evaluated by immunoblot. FIG. 21A, Western blot of 80 ug of Tyr694 p-STAT5; FIG. 21B, IHC of Tyr694 p-STAT5.

DETAILED DESCRIPTION

Figure 1:
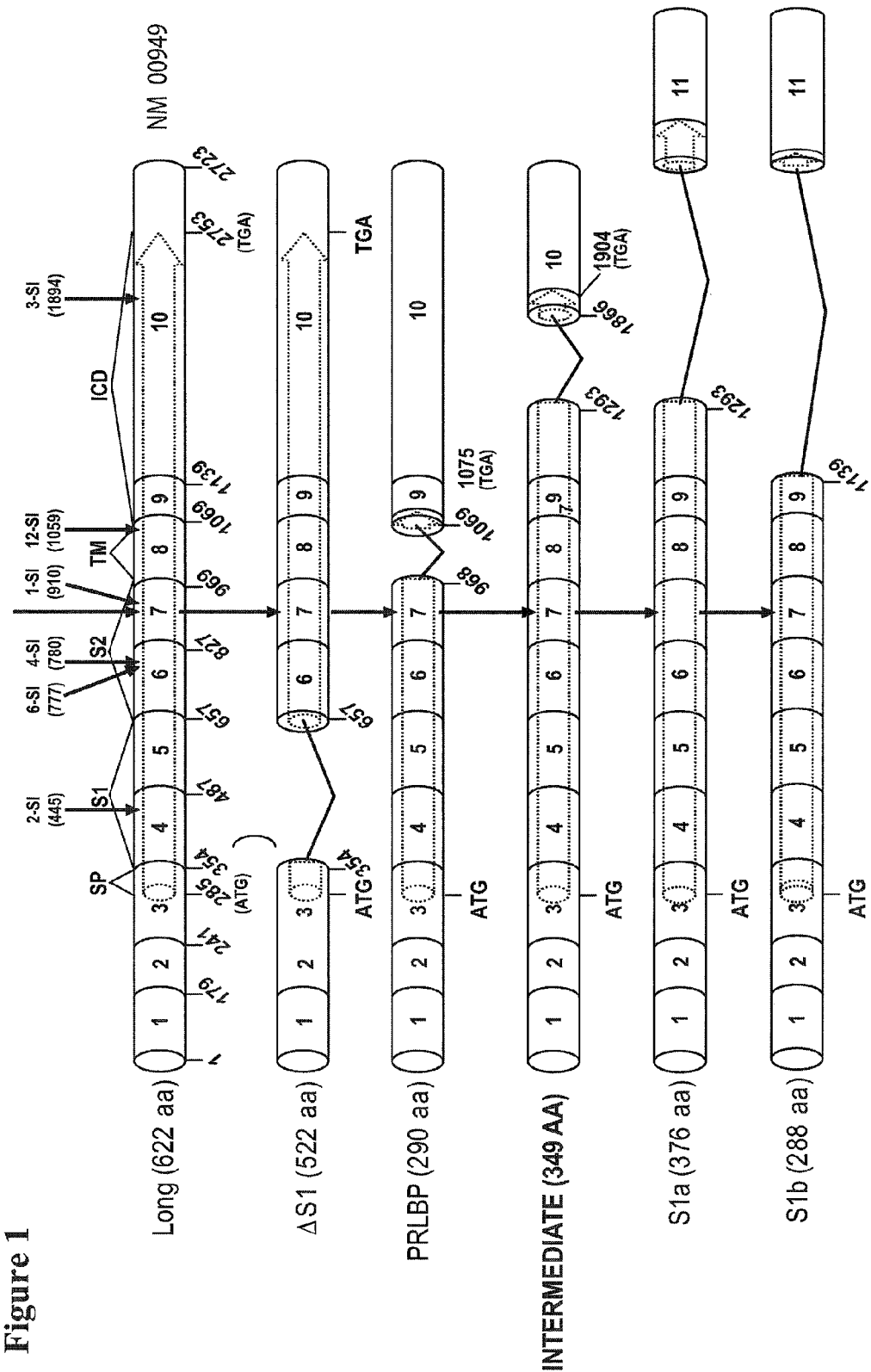
FIG. 1 shows the gene arrangement and exons in various isoforms of PRLR.

The present invention provides PRLR-specific antibodies, pharmaceutical formulations containing such antibodies, methods of preparing the antibodies and pharmaceutical formulations, and methods of treating patients with the pharmaceutical formulations and compounds. Antibodies according to the present invention may have a desired biological activity of binding to PRLR and/or inhibiting the dimerization of PRLR and/or inhibiting PRLR intracellular phosphorylation, and/or inhibiting PRLR downstream signaling, e.g. through phosphorylation of Jak2, Mapk, Stat5, Erk1/2 and/or Akt, and inhibiting cellular proliferation associated with cancer or tumors. In this way, direct analysis of PRLR activation by detection of its phosphorylation or by assessing the phosphorylation status of other downstream signaling partners such as Jak2, Stat5, Erk1/2 and/or Akt, is contemplated. Analysis of downstream signaling pathways may thus be used to identify patients in need of anti-PRLR antibodies or used to monitor patients who have been treated with anti-PRLR antibodies.

Antibodies according to the present invention may alternatively (or in addition) have a desired biological activity of binding to PRLR expressed on cancer cells, thus serving to target cytotoxic therapies to the cancer cells.

The invention further relates to screening assays to identify antagonists or agonists of a PRLR gene or gene product and variants thereof. Thus, the invention relates to methods for identifying agonists or antagonists of a PRLR gene or gene product and variants thereof, and the use of said agonist or antagonist to treat or prevent cancer as described herein. Additionally, the present invention contemplates use of the nucleic acid molecules, polypeptides, and/or antagonists or agonists of gene products encoded a PRLR gene to screen, diagnose, prevent and/or treat disorders characterized by aberrant expression or activity of PRLR, which include, cancers, such as but not limited to cancer of the lung, breast, and prostate.

Several preferred murine or chimeric antibodies with high affinity and potency as measured by in vitro assays are modified to be less immunogenic in humans based on the Human Engineering™ method of Studnicka et al. Briefly, surface exposed amino acid residues of the heavy chain and light chain variable regions are modified to human residues in positions determined to be unlikely to adversely effect either antigen binding or protein folding, while reducing its immunogenicity with respect to a human environment. Synthetic genes containing modified heavy and/or light chain variable regions are constructed and linked to human γ heavy chain and/or kappa light chain constant regions. Any human heavy chain and light chain constant regions may be used in combination with the HUMAN ENGINEERED™ antibody variable regions. The human heavy and light chain genes are introduced into mammalian cells and the resultant recombinant immunoglobulin products are obtained and characterized.

Exemplary antibodies according to the invention include chXHA.06.642, chXHA.06.275, he.06.642-1, he.06.642-2, he.06.275-1, he.06.275-2, he.06.275-3, he.06.275-4, XPA.06.128, XPA.06.129, XPA.06.130, XPA.06.131, XPA.06.141, XPA.06.147, XPA.06.148, XPA.06.158, XPA.06.159, XPA.06.163, XPA.06.167, XPA.06.171, XPA.06.178, XPA.06.181, XPA.06.192, XPA.06.202, XPA.06.203, XPA.06.206, XPA.06.207, XPA.06.210, XPA.06.212, XPA.06.217, XPA.06.219, XPA.06.229, XPA.06.233, XPA.06.235, XPA.06.239, XPA.06.145, XHA.06.567, XHA.06.642, XHA.06.983, XHA.06.275, XHA.06.189, and XHA.06.907. The following antibody-secreting hybridomas were deposited with the American Type Culture Collection (ATCC), 10801 University Blvd., Manassas, Va. 20110-2209 (USA), pursuant to the provisions of the Budapest Treaty, on Aug. 17, 2006:

| HYBRIDOMA NAME | ATCC DEPOSIT NUMBER |
|---|---|
| XHA.06.567 | PTA-7794 |
| XHA.06.642 | PTA-7795 |
| XHA.06.983 | PTA-7796 |
| XHA.06.275 | PTA-7797 |
| XHA.06.189 | PTA-7798 |
| XHA.06.907 | PTA-7799 |

The definitions below are provided as an aid to understanding the invention more completely.

GENERAL DEFINITIONS

The target antigen human "PRLR" as used herein refers to a human polypeptide having substantially the same amino acid sequence as SEQ ID NO: 2 and naturally occurring allelic and/or splice variants thereof. "ECD of PRLR" as used herein refers to the extracellular portion of PRLR represented by amino acids 25 to 234 of SEQ ID NO: 2.

"Tumor", as used herein, refers to all neoplastic cell growth and proliferation, whether malignant or benign, and all precancerous and cancerous cells and tissues.

The terms "cancer" and "cancerous" refer to or describe the physiological condition in mammals that is typically characterized by unregulated cell growth. Examples of cancer include but are not limited to breast cancer, colon cancer, kidney cancer, liver cancer, lung cancer, lymphoid cancer, ovary cancer, pancreas cancer, prostate cancer, uterine cancer, cervix cancer or skin cancer.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. Treatment of patients suffering from clinical, biochemical, radiological or subjective symptoms of the disease may include alleviating some or all of such symptoms or reducing the predisposition to the disease. The "pathology" of cancer includes all phenomena that compromise the well being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, etc. Thus, improvement after treatment may be manifested as decreased tumor size, decline in tumor growth rate, destruction of existing tumor cells or metastatic cells, and/or a reduction in the size or number of metastases.

"Mammal" for purposes of treatment refers to any animal classified as a mammal, including humans, domestic and farm animals, and zoo, sports, or pet animals, such as dogs, horses, cats, cows, etc. Preferably, the mammal is human.

As used herein, the phrase "therapeutically effective amount" is meant to refer to an amount of therapeutic or prophylactic antibody that would be appropriate for an embodiment of the present invention, that will elicit the desired therapeutic or prophylactic effect or response, including alleviating some or all of such symptoms of disease or reducing the predisposition to the disease, when administered in accordance with the desired treatment regimen.

Antibodies

"Affinity" or "binding affinity" are often measured by equilibrium association constant ($K_A$) or equilibrium dissociation constant ($K_D$). The term "immunospecific" or "specifically binding" means that the antibody binds to PRLR or its ECD with an equilibrium association constant ($K_A$) of greater than or equal to about $10^6 M^{-1}$, greater than or equal to about $10^7 M^{-1}$, greater than or equal to about $10^8 M^{-1}$, or greater than or equal to about $10^9 M^{-1}$, $10^{10} M^{-1}$, $10^{11} M^{-1}$ or $10^{12} M^{-1}$. The antibody may have substantially greater affinity for the target antigen compared to other unrelated molecules. The antibody may also have substantially greater affinity for the target antigen compared to orthologs or homologs, e.g. at least 1.5-fold, 2-fold, 5-fold 10-fold, 100-fold, $10^3$-fold, $10^4$-fold, $10^5$-fold, $10^6$-fold or greater relative affinity for the target antigen. Alternatively, it might be useful for the antibody to cross react with a known homolog or ortholog.

Antibodies of the invention may also be characterized by an equilibrium dissociation constant ($K_D$) $10^{-4}$ M, $10^{-6}$ M to $10^{-7}$ M, or $10^{-8}$M, $10^{-10}$ M, $10^{-11}$ M or $10^{-12}$ M or lower. Such affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. Sci., 51:660 (1949).

By "neutralizing antibody" is meant an antibody molecule that is able to eliminate or significantly reduce an effecter function of a target antigen to which is binds. Accordingly, a "neutralizing" anti-target antibody is capable of eliminating or significantly reducing an effecter function, such as enzyme activity, ligand binding, or intracellular signaling.

The term "antibody" is used in the broadest sense and includes fully assembled antibodies, monoclonal antibodies, polyclonal antibodies, multispecific antibodies (e.g., bispecific antibodies), antibody fragments that can bind antigen (e.g., Fab', F'(ab)2, Fv, single chain antibodies, diabodies), camel bodies and recombinant peptides comprising the forgoing as long as they exhibit the desired biological activity. Antibody fragments may be produced by recombinant DNA techniques or by enzymatic or chemical cleavage of intact antibodies and are described further below. Nonlimiting examples of monoclonal antibodies include murine, chimeric, humanized, human, and HUMAN ENGINEERED™ immunoglobulins, antibodies, chimeric fusion proteins having sequences derived from immunoglobulins, or muteins or derivatives thereof, each described further below. Multimers or aggregates of intact molecules and/or fragments, including chemically derivatized antibodies, are contemplated. Antibodies of any isotype class or subclass are contemplated according to the present invention.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that are typically include different antibodies directed against different determinants (epitopes), each monoclonal antibody is directed against a single determinant on the antigen. In addition to their specificity, the monoclonal antibodies are advantageous in that they are synthesized by the homogeneous culture, uncontaminated by other immunoglobulins with different specificities and characteristics.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 [1975], or may be made by recombinant DNA methods (see, e.g., U.S. Pat. No. 4,816,567). The "monoclonal antibodies" may also be recombinant, chimeric, humanized, human, HUMAN ENGINEERED™, or antibody fragments, for example.

An "isolated" antibody is one that has been identified and separated and recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "immunoglobulin" or "native antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a "variable" region of about 100 to 110 or more amino acids primarily responsible for antigen recognition. The carboxy-terminal portion of each chain defines a constant region primarily responsible for effector function. Immunoglobulins can be assigned to different classes depending on the amino acid sequence of the constant domain of their heavy chains. Heavy chains are classified as mu (μ), delta (Δ), gamma (γ), alpha (α), and epsilon (ε), and define the antibody's isotype as IgM, IgD, IgG, IgA, and IgE, respectively. Several of these may be further divided into subclasses or isotypes, e.g. IgG1, IgG2, IgG3, IgG4, IgA1 and IgA2. Different isotypes have different effector functions; for example, IgG1 and IgG3 isotypes have ADCC activity. Human light chains are classified as kappa (κ) and lambda (λ) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)).

For a detailed description of the structure and generation of antibodies, see Roth, D. B., and Craig, N. L., *Cell*, 94:411-414 (1998), herein incorporated by reference in its entirety. Briefly, the process for generating DNA encoding the heavy and light chain immunoglobulin genes occurs primarily in developing B-cells. Prior to the rearranging and joining of various immunoglobulin gene segments, the V, D, J and constant (C) gene segments are found generally in relatively close proximity on a single chromosome. During B-cell-differentiation, one of each of the appropriate family members of the V, D, J (or only V and J in the case of light chain genes) gene segments are recombined to form functionally rearranged heavy and light immunoglobulin genes. This gene segment rearrangement process appears to be sequential. First, heavy chain D-to-J joints are made, followed by heavy chain V-to-DJ joints and light chain V-to-J joints. In addition to the rearrangement of V, D and J segments, further diversity is generated in the primary repertoire of immunoglobulin heavy and light chain by way of variable recombination at the locations where the V and J segments in the light chain are joined and where the D and J segments of the heavy chain are joined. Such variation in the light chain typically occurs within the last codon of the V gene segment and the first codon of the J segment. Similar imprecision in joining occurs on the heavy chain chromosome between the D and $J_H$ segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity. The net effect of such rearrangements in the variable region gene segments and the variable recombination which may occur during such joining is the production of a primary antibody repertoire.

"Antibody fragments" comprise a portion of an intact full length antibody (including, e.g., human antibodies), preferably the antigen binding or variable region of the intact antibody, and include multispecific antibodies formed from antibody fragments. Nonlimiting examples of antibody fragments include Fab, Fab', F(ab')2, Fv, domain antibody (dAb), complementarity determining region (CDR) fragments, single-chain antibodies (scFv), single chain antibody fragments, diabodies, triabodies, tetrabodies, minibodies, linear antibodies (Zapata et al., Protein Eng., 8(10):1057-1062 (1995)); chelating recombinant antibodies, tribodies or bibodies, intrabodies, nanobodies, small modular immunopharmaceuticals (SMIPs), an antigen-binding-domain immunoglobulin fusion protein, a camelized antibody, a VHH containing antibody, or muteins or derivatives thereof, and polypeptides that contain at least a portion of an immunoglobulin that is sufficient to confer specific antigen binding to the polypeptide, such as a CDR sequence, as long as the antibody retains the desired biological activity.

Papain digestion of antibodies produces two identical antigen-binding fragments, called "Fab" fragments, each with a single antigen-binding site, and a residual "Fc" fragment, whose name reflects its ability to crystallize 35 readily. Pepsin treatment yields an F(ab')2 fragment that has two "Fv" fragments. An "Fv" fragment is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH VL dimer. Collectively, the six CDRs confer antigen-binding specificity to the antibody. However, even a single variable domain (or half of an Fv comprising only three CDRs specific for an antigen) has the ability to recognize and bind antigen.

"Single-chain Fv" or "sFv" or "scFv" antibody fragments comprise the VH and VL domains of antibody, wherein these domains are present in a single polypeptide chain. Preferably, the Fv polypeptide further comprises a polypeptide linker between the VH and VL domains that enables the Fv to form the desired structure for antigen binding. For a review of sFv see Pluckthun in The Pharmacology of Monoclonal Antibodies, vol. 1 13, Rosenburg and Moore eds., Springer-Verlag, New York, pp. 269-315 (1994).

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them.

The term "hypervariable" region refers to the amino acid residues of an antibody which are responsible for antigen-binding. The hypervariable region comprises amino acid residues from a "complementarity determining region" or CDR [i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, $5^{th}$ Ed. Public Health Service, National Institutes of Health, Bethesda, Md. (1991)] and/or those residues from a hypervariable loop (i.e., residues 26-32 (L1), 50-52 (L2) and 91-96 (L3) in the light chain variable domain and 26-32 (H1), 53-55 (H2) and 96-101 (H3) in the heavy chain variable domain as described by [Chothia et al., *J. Mol. Biol.* 196: 901-917 (1987)].

"Framework" or FR residues are those variable domain residues other than the hypervariable region residues.

The phrase "constant region" refers to the portion of the antibody molecule that confers effector functions.

The phrase "chimeric antibody," as used herein, refers to an antibody containing sequence derived from two different antibodies (see, e.g., U.S. Pat. No. 4,816,567) which typically originate from different species. Most typically, chimeric antibodies comprise human and murine antibody fragments, generally human constant and mouse variable regions.

The term "mutein" or "variant" can be used interchangeably and refers to the polypeptide sequence of an antibody that contains at least one amino acid substitution, deletion, or insertion in the variable region or the portion equivalent to the variable region, provided that the mutein or variant retains the desired binding affinity or biological activity. Muteins may be substantially homologous or substantially identical to the parent antibody.

The term "derivative" when used in connection with antibodies of the invention refers to antibodies covalently modified by such techniques as ubiquitination, conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. Derivatives of the invention will retain the binding properties of underivatized molecules of the invention.

When used herein, the term "antibody" specifically includes any one of the following that retain the ability to bind the extracellular portion of PRLR:

1) an amino acid mutein of a parent antibody having the amino acid sequence set out in FIG. 7A-7C or FIG. 8, including muteins comprising a variable heavy chain amino acid sequence which is at least 60, 65, 70, 75, 80, 85, 90, 91, 92, 93, 94, 95, 96, 97, 98, or 99% homologous to the parent amino acid sequence, and/or comprising a variable light chain amino acid sequence which is at least 60, 65, 70, 75, 80, 85, 90, 91, 92, 93, 94, 95, 96, 97, 98, or 99% homologous to the parent amino acid sequence, taking into account similar amino acids for the homology determination;

2) PRLR-binding polypeptides comprising one or more complementary determining regions (CDRs) of a parent antibody having the amino acid sequence set out in FIG. 7A-7C or FIG. 8, preferably comprising at least CDR3 of the heavy chain, and preferably comprising two or more, or three or more, or four or more, or five or more, or all six CDRs;

3) HUMAN ENGINEERED™ antibodies generated by altering the parent sequence according to the methods set forth in Studnicka et al., U.S. Pat. No. 5,766,886 and Example 5 herein, using Kabat numbering to identify low, moderate and high risk residues; such antibodies comprising at least one of the following heavy chains and at least one of the following light chains: (a) a heavy chain in which all of the low risk rodent residues that differ from corresponding residues in a human reference immunoglobulin sequence have been modified to be the same as the human residue in the human reference immunoglobulin sequence or (b) a heavy chain in which all of the low and moderate risk rodent residues have been modified, if necessary, to be the same residues as in the human reference immunoglobulin sequence, (c) a light chain in which all of the low risk residues have been modified, if necessary, to be the same residues as a human reference immunoglobulin sequence or (b) a light chain in which all of the low and moderate risk residues have been modified, if necessary, to be the same residues as a human reference immunoglobulin sequence 4) muteins of the aforementioned antibodies in preceding paragraph (3) comprising a heavy or light chain or heavy or light chain variable regions having at least 60% amino acid sequence identity with the original rodent light chain, more preferably at least 80%, more preferably at least 85%, more preferably at least 90%, and most preferably at least 95%, including for example, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, and 100% identical;

5) PRLR-binding polypeptides comprising the high risk residues of one or more CDRs of the rodent antibody, and preferably comprising high risk residues of two or more, or three or more, or four or more, or five or more, or all six CDRs, and optionally comprising one or more changes at the low or moderate risk residues;

for example, comprising one or more changes at a low risk residue and conservative substitutions at a moderate risk residue, or for example, retaining the moderate and high risk amino acid residues and comprising one or more changes at a low risk residue, where changes include insertions, deletions or substitutions and may be conservative substitutions or may cause the engineered antibody to be closer in sequence to a human light chain or heavy chain sequence, a human germline light chain or heavy chain sequence, a consensus human light chain or heavy chain sequence, or a consensus human germline light chain or heavy chain sequence. Such contemplated changes may also be displayed in sequence format as follows. In a hypothetical sequence of AKKLVHTPYSFKEDF (SEQ ID NO: 99), where the respective risk allotted to each residue according to Studnicka et al., U.S. Pat. No. 5,766,886, is HMLHMLHMLHMLHML (H=high, M=medium, L=low), exemplary changes to the low risk residues of the hypothetical sequence may be displayed as: AKXLVXTPXSFXEDX (SEQ ID NO: 100) where X is any amino acid, or alternatively where X is a conservative substitution of the original residue at that position, and exemplary changes to the low and moderate risk residues can be displayed similarly, e.g. AYXLYX-TYXSYXEYX (SEQ ID NO: 101), where X is any amino acid and Y is a conservative substitution of the original residue at that position.

The term "competing antibody" includes 1) a non-murine or non-rodent monoclonal antibody that binds to the same epitope of PRLR as antibody chXHA.06.642, chXHA.06.275, he.06.642-1, he.06.642-2, he.06.275-1, he.06.275-2, he.06.275-3, he.06.275-4, XPA.06.128, XPA.06.129, XPA.06.130, XPA.06.131, XPA.06.141, XPA.06.147, XPA.06.148, XPA.06.158, XPA.06.159, XPA.06.163, XPA.06.167, XPA.06.171, XPA.06.178, XPA.06.181, XPA.06.192, XPA.06.202, XPA.06.203, XPA.06.206, XPA.06.207, XPA.06.210, XPA.06.212, XPA.06.217, XPA.06.219, XPA.06.229, XPA.06.233, XPA.06.235, XPA.06.239, XPA.06.145, XHA.06.567, XHA.06.642, XHA.06.983, XHA.06.275, XHA.06.189, or XHA.06.907, e.g. as determined through X-ray crystallography; and 2) a non-murine or non-rodent monoclonal antibody that competes with murine antibody chXHA.06.642, chXHA.06.275, he.06.642-1, he.06.642-2, he.06.275-1, he.06.275-2, he.06.275-3, he.06.275-4, XPA.06.128, XPA.06.129, XPA.06.130, XPA.06.131, XPA.06.141, XPA.06.147, XPA.06.148, XPA.06.158, XPA.06.159, XPA.06.163, XPA.06.167, XPA.06.171, XPA.06.178, XPA.06.181, XPA.06.192, XPA.06.202, XPA.06.203, XPA.06.206, XPA.06.207, XPA.06.210, XPA.06.212, XPA.06.217, XPA.06.219, XPA.06.229, XPA.06.233, XPA.06.235, XPA.06.239, XPA.06.145, XHA.06.567, XHA.06.642, XHA.06.983, XHA.06.275, XHA.06.189, or XHA.06.907, by more than 75%, more than 80%, or more than 81%, 82%, 83%, 84%, 85%, 86%, 87%, 88%, 89%, 90%, 91%, 92%, 93%, 94% or 95%; alternatively, a first non-murine or non-rodent monoclonal antibody that reduces the binding affinity of chXHA.06.642, chXHA.06.275, he.06.642-1, he.06.642-2, he.06.275-1, he.06.275-2, he.06.275-3, he.06.275-4, XPA.06.128, XPA.06.129, XPA.06.130, XPA.06.131, XPA.06.141, XPA.06.147, XPA.06.148, XPA.06.158, XPA.06.159, XPA.06.163, XPA.06.167, XPA.06.171, XPA.06.178, XPA.06.181, XPA.06.192, XPA.06.202, XPA.06.203, XPA.06.206, XPA.06.207, XPA.06.210, XPA.06.212, XPA.06.217, XPA.06.219, XPA.06.229, XPA.06.233, XPA.06.235, XPA.06.239, XPA.06.145, XHA.06.567, XHA.06.642, XHA.06.983, XHA.06.275, XHA.06.189, or XHA.06.907 by at least 2, 3, 4, 5, 6, 10, 20, 50, 100 fold or greater.

Antibodies of the invention preferably bind to the ECD of PRLR with an equilibrium dissociation constant of $10^{-6}$, $10^{-7}$, $10^{-8}$, $10^{-9}$ M, $10^{-10}$ M, $10^{-11}$ M, $10^{-12}$ M or lower and preferably inhibit PRLR intracellular phosphorylation and activation of downstream PRLR signaling, e.g. through activation of STAT5, MAPK, or AKT.

Optionally, any chimeric, human or humanized antibody publicly disclosed before the filing date hereof, or disclosed in an application filed before the filing date hereof, is excluded from the scope of the invention.

"Non-rodent" monoclonal antibody is any antibody, as broadly defined herein, that is not a complete intact rodent monoclonal antibody generated by a rodent hybridoma. Thus, non-rodent antibodies specifically include, but are not limited to, muteins of rodent antibodies, rodent antibody fragments, linear antibodies, chimeric antibodies, humanized antibodies, HUMAN ENGINEERED™ antibodies and human antibodies, including human antibodies produced from transgenic animals or via phage display technology. Similarly, non-murine antibodies include but are not limited to muteins of murine antibodies, murine antibody fragments, linear antibodies, chimeric, humanized, HUMAN ENGINEERED™ and human antibodies.

Target Antigen

The target antigen to be used for production of antibodies may be, e.g., the extracellular portion of PRLR, or a fragment that retains the desired epitope, optionally fused to another polypeptide that allows the epitope to be displayed in its native conformation. Alternatively, intact PRLR expressed at the surface of cells can be used to generate antibodies. Such cells can be transformed to express PRLR or may be other naturally occurring cells that express PRLR. Other forms of PRLR polypeptides useful for generating antibodies will be apparent to those skilled in the art.

Polyclonal Antibodies

Polyclonal antibodies are preferably raised in animals by multiple subcutaneous (sc) or intraperitoneal (ip) injections of the relevant antigen and an adjuvant. An improved antibody response may be obtained by conjugating the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride or other agents known in the art.

Animals are immunized against the antigen, immunogenic conjugates, or derivatives by combining, e.g., 100 μg or 5 μs of the protein or conjugate (for rabbits or mice, respectively) with 3 volumes of Freund's complete adjuvant and injecting the solution intradermally at multiple sites. One month later, the animals are boosted with ⅕ to {fraction (1/10)} the original amount of peptide or conjugate in Freund's complete adjuvant by subcutaneous injection at multiple sites. At 7-14 days post-booster injection, the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Monoclonal antibodies may be made using the hybridoma method first described by Kohler et al., Nature, 256:495 (1975), or may be made by recombinant DNA methods.

In the hybridoma method, a mouse or other appropriate host animal, such as a hamster or macaque monkey, is immunized as herein described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)), or can be fused using electrocell fusion.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium. Human myeloma and mouse-human heteromyeloma cell lines also have been described for the production of human monoclonal antibodies (Kozbor, J. Immunol., 133: 3001 (1984); Brodeur et al., Monoclonal Antibody Production Techniques and Applications, pp. 51-63 (Marcel Dekker, Inc., New York, 1987)). Exemplary murine myeloma lines include those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by Scatchard analysis (Munson et al., Anal. Biochem., 107:220 (1980)).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies may be isolated and sequenced from the hybridoma cells using conventional procedures (e.g., by using oligonucleotide probes that are capable of binding specifically to genes encoding the heavy and light chains of the monoclonal antibodies). Sequence determination will generally require isolation of at least a portion of the gene or cDNA of interest. Usually this requires cloning the DNA or, preferably, mRNA (i.e., cDNA) encoding the monoclonal antibodies. Cloning is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+ mRNA, preferably membrane-associated mRNA, and the library screened using probes specific for human immunoglobulin polypeptide gene sequences. In a preferred embodiment, however, the polymerase chain reaction (PCR) is used to amplify cDNAs (or portions of full-length cDNAs) encoding an immunoglobulin gene segment of interest (e.g., a light chain variable segment). The amplified sequences can be readily cloned into any suitable vector, e.g., expression vectors, minigene vectors, or phage display vectors. It will be appreciated that the particular method of cloning used not critical, so long as it is possible to determine the sequence of some portion of the immunoglobulin polypeptide of interest. As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined, is considered isolated. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

One source for RNA used for cloning and sequencing is a hybridoma produced by obtaining a B cell from the transgenic mouse and fusing the B cell to an immortal cell. An advantage of using hybridomas is that they can be easily screened, and a hybridoma that produces a human monoclonal antibody of interest selected. Alternatively, RNA can be isolated from B cells (or whole spleen) of the immunized animal. When sources other than hybridomas are used, it may be desirable to screen for sequences encoding immunoglobulins or immunoglobulin polypeptides with specific binding characteristics. One method for such screening is the use of phage display technology. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference. In one embodiment using phage display technology, cDNA from an immunized transgenic mouse (e.g., total spleen cDNA) is isolated, the polymerase chain reaction is used to amplify a cDNA sequences that encode a portion of an immunoglobulin polypeptide, e.g., CDR regions, and the amplified sequences are inserted into a phage vector. cDNAs encoding peptides of interest, e.g., variable region peptides with desired binding characteristics, are identified by standard techniques such as panning.

The sequence of the amplified or cloned nucleic acid is then determined. Typically the sequence encoding an entire variable region of the immunoglobulin polypeptide is determined, however, it will sometimes by adequate to sequence only a portion of a variable region, for example, the CDR-encoding portion. Typically the portion sequenced will be at least 30 bases in length, more often based coding for at least about one-third or at least about one-half of the length of the variable region will be sequenced.

Sequencing can be carried out on clones isolated from a cDNA library, or, when PCR is used, after subcloning the amplified sequence or by direct PCR sequencing of the amplified segment. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Antibody Fragments

As noted above, antibody fragments comprise a portion of an intact full length antibody, preferably an antigen binding or variable region of the intact antibody, and include linear antibodies and multispecific antibodies formed from antibody fragments. Nonlimiting examples of antibody fragments include Fab, Fab', F(ab')2, Fv, Fd, domain antibody (dAb), complementarity determining region (CDR) fragments, single-chain antibodies (scFv), single chain antibody fragments, diabodies, triabodies, tetrabodies, minibodies, linear antibodies, chelating recombinant antibodies, tribodies or bibodies, intrabodies, nanobodies, small modular immunopharmaceuticals (SMIPs), an antigen-binding-domain immunoglobulin fusion protein, a camelized antibody, a VHH containing antibody, or muteins or derivatives thereof, and polypeptides that contain at least a portion of an immunoglobulin that is sufficient to confer specific antigen binding to the polypeptide, such as a CDR sequence, as long as the antibody retains the desired biological activity. Such antigen fragments may be produced by the modification of whole antibodies or synthesized de novo using recombinant DNA technologies or peptide synthesis.

The term "diabodies" refers to small antibody fragments with two antigen-binding sites, which fragments comprise a heavy-chain variable domain (VH) connected to a light-chain variable domain (VL) in the same polypeptide chain (VH VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and 30 Hollinger et al., Proc. Natl. Acad. Sci. USA, 90:6444-6448 (1993).

"Single-chain Fv" or "scFv" antibody fragments comprise the $V_H$ and $V_L$ domains of antibody, wherein these domains are present in a single polypeptide chain, and optionally comprising a polypeptide linker between the $V_H$ and $V_L$ domains that enables the Fv to form the desired structure for antigen binding (Bird et al., Science 242:423-426, 1988, and Huston et al., Proc. Natl. Acad. Sci. USA 85:5879-5883, 1988). An Fd fragment consists of the $V_H$ and $C_H1$ domains.

Additional antibody fragment include a domain antibody (dAb) fragment (Ward et al., Nature 341:544-546, 1989) which consists of a $V_H$ domain.

"Linear antibodies" comprise a pair of tandem Fd segments ($V_H$-$C_H1$-$V_H$-$C_H1$) which form a pair of antigen binding regions. Linear antibodies can be bispecific or monospecific (Zapata et al. Protein Eng. 8:1057-62 (1995)).

A "minibody" consisting of scFv fused to CH3 via a peptide linker (hingeless) or via an IgG hinge has been described in Olafsen, et al., Protein Eng Des Sel. 2004 April; 17(4):315-23.

Functional heavy-chain antibodies devoid of light chains are naturally occurring in nurse sharks (Greenberg et al., Nature 374:168-73, 1995), wobbegong sharks (Nuttall et al., Mol Immunol. 38:313-26, 2001) and Camelidae (Hamers-Casterman et al., Nature 363: 446-8, 1993; Nguyen et al., J. Mol. Biol. 275: 413, 1998), such as camels, dromedaries, alpacas and llamas. The antigen-binding site is reduced to a single domain, the $VH_H$ domain, in these animals. These antibodies form antigen-binding regions using only heavy chain variable region, i.e., these functional antibodies are homodimers of heavy chains only having the structure $H_2L_2$ (referred to as "heavy-chain antibodies" or "HCAbs"). Camelized $V_{HH}$ reportedly recombines with IgG2 and IgG3 constant regions that contain hinge, CH2, and CH3 domains and lack a CH1 domain (Hamers-Casterman et al., supra). For example, llama IgG1 is a conventional ($H_2L_2$) antibody isotype in which $V_H$ recombines with a constant region that contains hinge, CH1, CH2 and CH3 domains, whereas the llama IgG2 and IgG3 are heavy chain-only isotypes that lack CH1 domains and that contain no light chains. Classical $V_H$-only fragments are difficult to produce in soluble form, but improvements in solubility and specific binding can be obtained when framework residues are altered to be more $VH_H$-like. (See, e.g., Reichman, et al., J Immunol Methods 1999, 231:25-38.) Camelized $V_{HH}$ domains have been found to bind to antigen with high affinity (Desmyter et al., *J. Biol. Chem.* 276:26285-90, 2001) and possess high stability in solution (Ewert et al., *Biochemistry* 41:3628-36, 2002). Methods for generating antibodies having camelized heavy chains are described in, for example, in U.S. Patent Publication Nos. 20050136049 and 20050037421.

Because the variable domain of the heavy-chain antibodies is the smallest fully functional antigen-binding fragment with a molecular mass of only 15 kDa, this entity is referred to as a nanobody (Cortez-Retamozo et al., *Cancer Research* 64:2853-57, 2004). A nanobody library may be generated from an immunized dromedary as described in Conrath et al., (*Antimicrob Agents Chemother* 45: 2807-12, 2001) or using recombinant methods as described in Intrabodies are single chain antibodies which demonstrate intracellular expression and can manipulate intracellular protein function (Biocca, et al., *EMBO J.* 9:101-108, 1990; Colby et al., *Proc Natl Acad Sci USA*. 101:17616-21, 2004). Intrabodies, which comprise cell signal sequences which retain the antibody construct in intracellular regions, may be produced as described in Mhashilkar et al (EMBO J 14:1542-51, 1995) and Wheeler et al. (*FASEB J.* 17:1733-5. 2003). Transbodies are cell-permeable antibodies in which a protein transduction domains (PTD) is fused with single chain variable fragment (scFv) antibodies Heng et al., (*Med Hypotheses.* 64:1105-8, 2005).

Further contemplated are antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

Multivalent Antibodies

In some embodiments, it may be desirable to generate multivalent or even a multispecific (e.g. bispecific, trispecific, etc.) monoclonal antibody. Such antibody may have binding specificities for at least two different epitopes of the target antigen, or alternatively it may bind to two different molecules, e.g. to the target antigen and to a cell surface protein or receptor. For example, a bispecific antibody may include an arm that binds to the target and another arm that binds to a triggering molecule on a leukocyte such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the target-expressing cell. As another example, bispecific antibodies may be used to localize cytotoxic agents to cells which express target antigen. These antibodies possess a target-binding arm and an arm which binds the cytotoxic agent (e.g., saporin, anti-interferon-60, vinca alkaloid, ricin A chain, methotrexate or radioactive isotope hapten). Multispecific antibodies can be prepared as full length antibodies or antibody fragments.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques.

According to another approach for making bispecific antibodies, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO96/27011 published Sep. 6, 1996.

Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. Better et al., Science 240: 1041-1043 (1988) disclose secretion of functional antibody fragments from bacteria (see, e.g., Better et al., Skerra et al. Science 240: 1038-1041 (1988)). For example, Fab'-SH fragments can be directly recovered from *E. coli* and chemically coupled to form bispecific antibodies (Carter et al., Bio/Technology 10:163-167 (1992); Shalaby et al., J. Exp. Med. 175:217-225 (1992)).

Shalaby et al., J. Exp. Med. 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers, e.g. GCN4. (See generally Kostelny et al., J. Immunol. 148(5):1547-1553 (1992).) The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

The term "diabodies" refers to small antibody fragments with two antigen-binding sites, which fragments comprise a heavy-chain variable domain (VH) connected to a light-chain variable domain (VL) in the same polypeptide chain (VH VL). By using a linker that is too short to allow pairing between the two domains on the same chain, the domains are forced to pair with the complementary domains of another chain and create two antigen-binding sites. See, for example, Hollinger et al., Proc. Natl. Acad. Sci. USA, 90:6444-6448 (1993).

Another strategy for making bispecific antibody fragments by the use of single-chain Fv (sFv) dimers has also been reported. See Gruber et al., J. Immunol. 152: 5368 (1994).

Alternatively, the bispecific antibody may be a "linear antibody" produced as described in Zapata et al. Protein Eng. 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

Antibodies with more than two valencies are also contemplated. For example, trispecific antibodies can be prepared. (Tutt et al., J. Immunol. 147:60 (1991)).

A "chelating recombinant antibody" is a bispecific antibody that recognizes adjacent and non-overlapping epitopes of the target antigen, and is flexible enough to bind to both epitopes simultaneously (Neri et al., *J Mol Biol*. 246:367-73, 1995).

Production of bispecific Fab-scFv ("bibody") and trispecific Fab-(scFv)(2) ("tribody") are described in Schoonjans et al. (*J Immunol*. 165:7050-57, 2000) and Willems et al. (*J Chromatogr B Analyt Technol Biomed Life Sci*. 786:161-76, 2003). For bibodies or tribodies, a scFv molecule is fused to one or both of the VL-CL (L) and VH-$CH_1$ (Fd) chains, e.g., to produce a tribody two scFvs are fused to C-term of Fab while in a bibody one scFv is fused to C-term of Fab.

Recombinant Production of Antibodies

Antibodies may be produced by recombinant DNA methodology using one of the antibody expression systems well known in the art (See, e.g., Harlow and Lane, Antibodies: A Laboratory Manual, Cold Spring Harbor Laboratory (1988)).

DNA encoding antibodies of the invention may be placed into expression vectors, which are then transfected into host cells such as *E. coli* cells, simian COS cells, human embryonic kidney 293 cells (e.g., 293E cells), Chinese hamster ovary (CHO) cells, or myeloma cells that do not otherwise produce immunoglobulin protein, to obtain the synthesis of monoclonal antibodies in the recombinant host cells. Recombinant production of antibodies is well known in the art. Antibody fragments have been derived via proteolytic digestion of intact antibodies (see, e.g., Morimoto et al., Journal of Biochemical and Biophysical Methods 24:107-117 (1992) and Brennan et al., Science 229:81 (1985)). However, these fragments can now be produced directly by recombinant host cells. Other techniques for the production of antibody fragments, including peptide synthesis and covalent linkage, will be apparent to the skilled practitioner.

Expression control sequences refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Cell, cell line, and cell culture are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

In an alternative embodiment, the amino acid sequence of an immunoglobulin of interest may be determined by direct protein sequencing. Suitable encoding nucleotide sequences can be designed according to a universal codon table.

Amino acid sequence muteins of the desired antibody may be prepared by introducing appropriate nucleotide changes into the encoding DNA, or by peptide synthesis. Such muteins include, for example, deletions from, and/or insertions into and/or substitutions of, residues within the amino acid sequences of the antibodies. Any combination of deletion, insertion, and substitution is made to arrive at the final construct, provided that the final construct possesses the desired characteristics. The amino acid changes also may alter post-translational processes of the monoclonal, human, humanized, HUMAN ENGINEERED™ or mutein antibody, such as changing the number or position of glycosylation sites.

Nucleic acid molecules encoding amino acid sequence muteins of the antibody are prepared by a variety of methods known in the art. These methods include, but are not limited to, isolation from a natural source (in the case of naturally occurring amino acid sequence muteins) or preparation by oligonucleotide-mediated (or site-directed) mutagenesis, PCR mutagenesis, and cassette mutagenesis of an earlier prepared mutein or a non-mutein version of the antibody.

The invention also provides isolated nucleic acid encoding antibodies of the invention, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium.

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more selective marker genes, an enhancer element, a promoter, and a transcription termination sequence.

(1) Signal Sequence Component

The antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The signal sequence selected preferably is one that is recognized and processed (i.e., cleaved by a signal peptidase) by the host cell. If prokaryotic host cells do not recognize and process the native antibody signal sequence, the signal sequence may be substituted by a signal sequence selected, for example, from the group of the pectate lyase (e.g., pelB) alkaline phosphatase, penicillinase, lpp, or heat-stable enterotoxin II leaders. For yeast secretion the native signal sequence may be substituted by, e.g., the yeast invertase leader, a factor leader (including Saccharomyces and Kluyveromyces α-factor leaders), or acid phosphatase leader, the C. albicans glucoamylase leader, or the signal described in WO90/13646. In mammalian cell expression, mammalian signal sequences as well as viral secretory leaders, for example, the herpes simplex gD signal, are available.

The DNA for such precursor region is ligated in reading frame to DNA encoding the antibody.

(2) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins are useful for cloning vectors in mammalian cells. Generally, the origin of replication component is not needed for mammalian expression vectors (the SV40 origin may typically be used only because it contains the early promoter).

(3) Selective Marker Component

Expression and cloning vectors may contain a selective gene, also termed a selectable marker. Typical selection genes encode proteins that (a) confer resistance to antibiotics or other toxins, e.g., ampicillin, neomycin, methotrexate, tetracycline, G418, geneticin, histidinol, or mycophenolic acid (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs methotrexate, neomycin, histidinol, puromycin, mycophenolic acid and hygromycin.

Another example of suitable selectable markers for mammalian cells are those that enable the identification of cells competent to take up the antibody-encoding nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding antibody of the invention, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282: 39 (1979)). The trp1 gene provides a selection marker for a mutant strain of yeast lacking the ability to grow in tryptophan, for example, ATCC No. 44076 or PEP4-1. Jones, Genetics, 85: 12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene. Ura3-deficient yeast strains are complemented by plasmids bearing the ura3 gene.

In addition, vectors derived from the 1.6 μm circular plasmid pKD1 can be used for transformation of Kluyveromyces yeasts. Alternatively, an expression system for large-scale production of recombinant calf chymosin was reported for K. lactis. Van den Berg, Bio/Technology, 8: 135 (1990). Stable multi-copy expression vectors for secretion of mature recombinant human serum albumin by industrial strains of Kluyveromyces have also been disclosed. Fleer et al, Bio/Technology, 9: 968-975 (1991).

(4) Promoter Component

Expression and cloning vectors usually contain a promoter that is recognized by the host organism and is operably linked to the antibody-encoding nucleic acid. Promoters suitable for use with prokaryotic hosts include the arabinose (e.g., araB) promoter phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibody of the invention.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as Abelson leukemia virus, polyoma virus, fowlpox virus, adenovirus (such as Adenovirus 2), bovine papilloma virus, avian sarcoma virus, most preferably cytomegalovirus, a retrovirus, hepatitis-B virus, Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297: 598-601 (1982) on expression of human β-interferon cDNA in mouse cells under the control of a thymidine kinase promoter from herpes simplex virus. Alternatively, the rous sarcoma virus long terminal repeat can be used as the promoter.

(5) Enhancer Element Component

Transcription of a DNA encoding the antibody of this invention by higher eukaryotes is often increased by inserting an enhancer sequence into the vector. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297: 17-18 (1982) on enhancing elements for activation of eukaryotic promoters. The enhancer may be spliced into the vector at a position 5' or 3' to the antibody-encoding sequence, but is preferably located at a site 5' from the promoter.

(6) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein. Another is the mouse immunoglobulin light chain transcription terminator.

(7) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastors* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, tobacco, lemna, and other plant cells can also be utilized as hosts.

However, interest has been greatest in vertebrate cells, and propagation of vertebrate cells in culture (tissue culture) has become routine procedure. Examples of useful mammalian host cell lines are Chinese hamster ovary cells, including CHOK1 cells (ATCC CCL61), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, [Graham et al., *J. Gen Virol.* 36: 59 (1977)]; baby hamster kidney cells (BHK, ATCC CCL 10); mouse sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y Acad. Sci. 383: 44-68 (1982)); MRC 5 cells; FS4 cells; and a human hepatoma line (Hep G2).

Host cells are transformed or transfected with the above-described expression or cloning vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of antibodies.

(8) Culturing the Host Cells

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(9) Purification of Antibody

When using recombinant techniques, the antibody can be produced intracellularly, in the periplasmic space, or directly secreted into the medium, including from microbial cultures. If the antibody is produced intracellularly, as a first step, the particulate debris, either host cells or lysed fragments, is removed, for example, by centrifugation or ultrafiltration. Better et al. Science 240: 1041-1043 (1988); ICSU Short Reports 10: 105 (1990); and Proc. Natl. Acad. Sci. USA 90: 457-461 (1993) describe a procedure for isolating antibodies which are secreted to the periplasmic space of *E. coli*. (See also, [Carter et al., *Bio/Technology* 10: 163-167 (1992)].

The antibody composition prepared from microbial or mammalian cells can be purified using, for example, hydroxylapatite chromatography cation or avian exchange chromatography, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma 1$, $\gamma 2$, or $\gamma 4$ heavy chains (Lindmark et al., *J. Immunol. Meth.* 62: 1-13 (1983)). Protein G is recommended for all mouse isotypes and for human $\gamma 3$ (Guss et al., EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H 3$ domain, the Bakerbond ABX®resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Chimeric Antibodies

A rodent antibody on repeated in vivo administration in man either alone or as a conjugate will bring about an immune response in the recipient against the rodent antibody; the so-called HAMA response (Human Anti Mouse Antibody). The HAMA response may limit the effectiveness of the pharmaceutical if repeated dosing is required. The immunogenicity of the antibody may be reduced by chemical modification of the antibody with a hydrophilic polymer such as polyethylene glycol or by using genetic engineering methods to make the antibody structure more human like, e.g. chimeric, humanized, human or HUMAN ENGINEERED™ antibodies. Because such engineered antibodies are less immunogenic in humans than the parental mouse monoclonal antibodies, they can be used for the treatment of humans with far less risk of anaphylaxis. Thus, these antibodies may be preferred in therapeutic applications that involve in vivo administration to a human.

Chimeric monoclonal antibodies, in which the variable Ig domains of a mouse monoclonal antibody are fused to human constant Ig domains, can be generated using standard procedures known in the art (See Morrison, S. L., et al. (1984) Chimeric Human Antibody Molecules; Mouse Antigen Binding Domains with Human Constant Region Domains, Proc. Natl. Acad. Sci. USA 81, 6841-6855; and, Boulianne, G. L., et al, Nature 312, 643-646. (1984)). For example, the gene sequences for the variable domains of the rodent antibody which bind CEA can be substituted for the variable domains of a human myeloma protein, thus producing a recombinant chimeric antibody. These procedures are detailed in EP 194276, EP 0120694, EP 0125023, EP 0171496, EP 0173494 and WO 86/01533. Although some chimeric monoclonal antibodies have proved less immunogenic in humans, the mouse variable Ig domains can still lead to a significant human anti-mouse response.

Humanized Antibodies

Humanized antibodies may be achieved by a variety of methods including, for example: (1) grafting the non-human complementarity determining regions (CDRs) onto a human framework and constant region (a process referred to in the art as humanizing through "CDR grafting"), or, alternatively, (2) transplanting the entire non-human variable domains, but "cloaking" them with a human-like surface by replacement of surface residues (a process referred to in the art as "veneering"). In the present invention, humanized antibodies will include both "humanized" and "veneered" antibodies. These methods are disclosed in, e.g., Jones et al., Nature 321:522 525 (1986); Morrison et al., Proc. Natl. Acad. Sci., U.S.A., 81:6851 6855 (1984); Morrison and Oi, Adv. Immunol., 44:65 92 (1988); Verhoeyer et al., Science 239:1534 1536 (1988); Padlan, Molec. Immun. 28:489 498 (1991); Padlan, Molec. Immunol. 31(3):169 217 (1994); and Kettleborough, C. A. et al., Protein Eng. 4(7):773 83 (1991) each of which is incorporated herein by reference.

For example, the gene sequences of the CDRs of the rodent antibody may be isolated or synthesized and substituted for the corresponding sequence regions of a homologous human antibody gene, producing a human antibody with the specificity of the original rodent antibody. These procedures are described in EP 023940, WO 90/07861 and WO91/09967.

CDR grafting involves introducing one or more of the six CDRs from the mouse heavy and light chain variable Ig domains into the appropriate four framework regions of human variable Ig domains is also called CDR grafting. This technique (Riechmann, L., et al., Nature 332, 323 (1988)), utilizes the conserved framework regions (FR1-FR4) as a scaffold to support the CDR loops which are the primary contacts with antigen. A disadvantage of CDR grafting, however, is that it can result in a humanized antibody that has a substantially lower binding affinity than the original mouse antibody, because amino acids of the framework regions can contribute to antigen binding, and because amino acids of the CDR loops can influence the association of the two variable Ig domains. To maintain the affinity of the humanized monoclonal antibody, the CDR grafting technique can be improved by choosing human framework regions that most closely resemble the framework regions of the original mouse antibody, and by site-directed mutagenesis of single amino acids within the framework or CDRs aided by computer modeling of the antigen binding site (e.g., Co, M. S., et al. (1994), J. Immunol. 152, 2968-2976).

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors (See, e.g., U.S. Pat. Nos. 5,530,101 and 5,585,089 which patents are incorporated herein by reference).

A number of humanizations of mouse monoclonal antibodies by rational design have been reported (See, for example, 20020091240 published Jul. 11, 2002, WO 92/11018 and U.S. Pat. No. 5,693,762, U.S. Pat. No. 5,766,866.

HUMAN ENGINEERED™ Antibodies

The phrase "HUMAN ENGINEERED™ antibody" refers to an antibody derived from a non-human antibody, typically a mouse monoclonal antibody. Alternatively, a HUMAN ENGINEERED™ antibody may be derived from a chimeric antibody that retains or substantially retains the antigen binding properties of the parental, non-human, antibody but which exhibits diminished immunogenicity as compared to the parental antibody when administered to humans.

HUMAN ENGINEERED™ of antibody variable domains has been described by Studnicka [See, e.g., Studnicka et al. U.S. Pat. No. 5,766,886; Studnicka et al. Protein Engineering 7: 805-814 (1994)] as a method for reducing immunogenicity while maintaining binding activity of antibody molecules. According to the method, each variable region amino acid has been assigned a risk of substitution. Amino acid substitutions are distinguished by one of three risk categories: (1) low risk changes are those that have the greatest potential for reducing immunogenicity with the least chance of disrupting antigen binding; (2) moderate risk changes are those that would further reduce immunogenicity, but have a greater chance of affecting antigen binding or protein folding; (3) high risk residues are those that are important for binding or for maintaining antibody structure and carry the highest risk that antigen binding or protein folding will be affected. Due to the three-dimensional structural role of prolines, modifications at prolines are generally considered to be at least moderate risk changes, even if the position is typically a low risk position.

Variable regions of the light and heavy chains of a rodent antibody are HUMAN ENGINEERED™ as follows to substitute human amino acids at positions determined to be unlikely to adversely effect either antigen binding or protein folding, but likely to reduce immunogenicity in a human environment. Amino acid residues that are at "low risk" positions and that are candidates for modification according to the method are identified by aligning the amino acid sequences of the rodent variable regions with a human variable region sequence. Any human variable region can be used, including an individual VH or VL sequence or a human consensus VH or VL sequence or an individual or consensus human germline sequence. The amino acid residues at any number of the low risk positions, or at all of the low risk positions, can be changed. For example, at each low risk position where the aligned murine and human amino acid residues differ, an amino acid modification is introduced that replaces the rodent residue with the human residue. Alternatively, the amino acid residues at all of the low risk positions and at any number of the moderate risk positions can be changed. Ideally, to achieve the least immunogenicity all of the low and moderate risk positions are changed from rodent to human sequence.

Synthetic genes containing modified heavy and/or light chain variable regions are constructed and linked to human γ heavy chain and/or kappa light chain constant regions. Any human heavy chain and light chain constant regions may be used in combination with the HUMAN ENGINEERED™ antibody variable regions, including IgA (of any subclass, such as IgA1 or IgA2), IgD, IgE, IgG (of any subclass, such as IgG1, IgG2, IgG3, or IgG4), or IgM. The human heavy and light chain genes are introduced into host cells, such as mammalian cells, and the resultant recombinant immunoglobulin products are obtained and characterized.

Human Antibodies from Transgenic Animals

Human antibodies to target antigen can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions.

Using a transgenic animal described above, an immune response can be produced to a selected antigenic molecule, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL 6, IL 8, TNFa, human CD4, L selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096 and U.S. patent application no. 20030194404; and U.S. patent application no. 20030031667). See also Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. No. 5,591,669, U.S. Pat. No. 5,589,369, U.S. Pat. No. 5,545,807; and U.S. Patent Application No. 20020199213, WO 96/34096 and U.S. patent application no. 20030194404; and U.S. patent application no. 20030031667.

Additional transgenic animals useful to make monoclonal antibodies include the Medarex HuMAb-MOUSE®, described in U.S. Pat. No. 5,770,429 and Fishwild, et al. (Nat. Biotechnol. 14:845-851, 1996), which contains gene sequences from unrearranged human antibody genes that code for the heavy and light chains of human antibodies. Immunization of a HuMAb-MOUSE® enables the production of monoclonal antibodies to the target protein.

Also, Ishida et al. (Cloning Stem Cells. 4:91-102, 2002) describes the TransChromo Mouse (TCMOUSE™) which comprises megabase-sized segments of human DNA and which incorporates the entire human immunoglobulin (hIg) loci. The TCMOUSE has a fully diverse repertoire of hIgs, including all the subclasses of IgGs (IgG1-G4). Immunization of the TC Mouse with various human antigens produces antibody responses comprising human antibodies.

U.S. Patent Application No. 20030092125 describes methods for biasing the immune response of an animal to the desired epitope. Human antibodies may also be generated by in vitro activated B cells (see U.S. Pat. Nos. 5,567,610 and 5,229,275).

Antibodies from Phage Display Technology

The development of technologies for making repertoires of recombinant human antibody genes, and the display of the encoded antibody fragments on the surface of filamentous bacteriophage, has provided a recombinant means for directly making and selecting human antibodies, which also can be applied to humanized, chimeric, murine or mutein antibodies. The antibodies produced by phage technology are produced as antigen binding fragments-usually Fv or Fab fragments-in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

Typically, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. By several rounds of antigen binding and re-amplification, a procedure termed panning, Fab specific for the antigen are enriched and finally isolated.

In 1994, an approach for the humanization of antibodies, called "guided selection", was described. Guided selection utilizes the power of the phage display technique for the humanization of mouse monoclonal antibody (See Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., J. Mol. Biol., 227:381 (1991); Marks et al., J. Mol. Biol, 222:581-597 (1991); U.S. Pat. Nos. 5,565,332 and 5,573,905; Clackson, T., and Wells, J. A., TIBTECH 12, 173-184 (1994)). In particular, in vitro selection and evolution of antibodies derived from phage display libraries has become a powerful tool (See Burton, D. R., and Barbas III, C. F., Adv. Immunol. 57, 191-280 (1994); and, Winter, G., et al., Annu. Rev. Immunol. 12, 433-455 (1994); U.S. patent application no. 20020004215 and WO92/01047; U.S. patent application no. 20030190317 published Oct. 9, 2003 and U.S. Pat. No. 6,054,287; U.S. Pat. No. 5,877,293.

Watkins, "Screening of Phage-Expressed Antibody Libraries by Capture Lift," Methods in Molecular Biology, Antibody Phage Display: Methods and Protocols 178: 187-193, and U.S. patent application no. 200120030044772 published Mar. 6, 2003 describe methods for screening phage-expressed antibody libraries or other binding molecules by capture lift, a method involving immobilization of the candidate binding molecules on a solid support.

The antibody products may be screened for activity and for suitability in the treatment methods of the invention using assays as described in the section entitled "Screening Methods" herein or using any suitable assays known in the art.

Amino Acid Sequence Muteins

Antibodies of the invention include mutein or variants of a parent antibody wherein the polypeptide sequence of the parent antibody has been altered by at least one amino acid substitution, deletion, or insertion in the variable region or the portion equivalent to the variable region, including within the CDRs, provided that the mutein or variant retains the desired binding affinity or biological activity. Muteins may be substantially homologous or substantially identical to the parent antibody, e.g. at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical or homologous. Identity or homology with respect to this sequence is defined herein as the percentage of amino acid residues in the candidate sequence that are identical with the parent sequence, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology. Thus, sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences, or along a pre-determined portion of one or both sequences). The programs provide a default opening penalty and a default gap penalty, and a scoring matrix such as PAM 250 [a standard scoring matrix; see Dayhoff et al., in Atlas of Protein Sequence and Structure, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences.

Antibodies of the invention may also include alterations in the polypeptide sequence of the constant region, which will not affect binding affinity but may alter effector function, such as antibody-dependent cellular toxicity (ADCC), complement dependent cytotoxicity (CDC) or clearance and uptake (and resultant effect on half-life).

Insertions

Amino acid sequence insertions include amino- and/or carboxyl-terminal fusions ranging in length from one residue to polypeptides containing a hundred or more residues, as well as intra-sequence insertions of single or multiple amino acid residues, e.g. 2, 3 or more. Examples of terminal insertions include an antibody with an N-terminal methionyl residue or the antibody (including antibody fragment) fused to an epitope tag or a salvage receptor epitope. Other insertional muteins of the antibody molecule include the addition of glycosylation sites, addition of cysteines for intramolecular or intermolecular bonding, or fusion to a polypeptide which increases the serum half-life of the antibody, e.g. at the N-terminus or C-terminus. For example, cysteine bond(s) may be added to the antibody to improve its stability (particularly where the antibody is an antibody fragment such as an Fv fragment).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to an antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to an antibody by inserting or substituting one or more serine or threonine residues to the sequence of the original antibody.

The term "epitope tagged" refers to the antibody fused to an epitope tag. The epitope tag polypeptide has enough residues to provide an epitope against which an antibody there against can be made, yet is short enough such that it does not interfere with activity of the antibody. The epitope tag preferably is sufficiently unique so that the antibody there against does not substantially cross-react with other epitopes. Suitable tag polypeptides generally have at least 6 amino acid residues and usually between about 8-50 amino acid residues (preferably between about 9-30 residues). Examples include the flu HA tag polypeptide and its antibody 12CA5 [Field et al., *Mol. Cell. Biol.* 8: 2159-2165 (1988)]; the c-myc tag and the 8F9, 3C7, 6E10, G4, B7 and 9E10 antibodies thereto [Evan et al., *Mol. Cell. Biol.* 5(12): 3610-3616 (1985)]; and the Herpes Simplex virus glycoprotein D (gD) tag and its antibody [Paborsky et al., *Protein Engineering* 3(6): 547-553 (1990)]. Other exemplary tags are a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the invention.

As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Deletions

Amino acid sequence deletions include amino- and/or carboxyl-terminal deletions ranging in length from one to a hundred or more residues, resulting in fragments that retain binding affinity for target antigen, as well as intra-sequence deletions of single or multiple amino acid residues, e.g. 2, 3 or more. For example, glycosylation sites may be deleted or moved to a different position by deleting part or all of the tripeptide or other recognition sequences for glycosylation.

Substitutions

Another type of mutein is an amino acid substitution mutein. These muteins have at least one amino acid residue in the antibody molecule removed and a different residue inserted in its place. Substitutional mutagenesis within any of the hypervariable or CDR regions or framework regions is contemplated. Conservative substitutions are shown in Table 1. The most conservative substitution is found under the heading of "preferred substitutions". If such substitutions result in no change in biological activity, then more substantial changes, denominated "exemplary substitutions" in Table 1, or as further described below in reference to amino acid classes, may be introduced and the products screened.

TABLE 1

| Original | Exemplary | Preferred Residue Substitutions |
|---|---|---|
| Ala (A) | val; leu; ile | val |
| Arg (R) | lys; gln; asn | lys |
| Asn (N) | gln; his; asp, lys; gln | arg |
| Asp (D) | glu; asn | glu |
| Cys (C) | ser; ala | ser |
| Gln (Q) | asn; glu | asn |
| Glu (E) | asp; gln | asp |
| Gly (G) | ala | |
| His (H) | asn; gln; lys; arg | |
| Ile (I) | leu; val; met; ala; phe; | leu norleucine |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | |
| Pro (P) | ala | |
| Ser (S) | thr | |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Conservative substitutions involve replacing an amino acid with another member of its class. Non-conservative substitutions involve replacing a member of one of these classes with a member of another class.

Any cysteine residue not involved in maintaining the proper conformation of the antibody also may be substituted, generally with serine, to improve the oxidative stability of the molecule and prevent aberrant crosslinking.

Affinity maturation generally involves preparing and screening antibody variants that have substitutions within the CDRs of a parent antibody and selecting variants that have improved biological properties such as binding affinity relative to the parent antibody. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity). See e.g., WO 92/01047, WO 93/112366, WO 95/15388 and WO 93/19172.

Current antibody affinity maturation methods belong to two mutagenesis categories: stochastic and nonstochastic. Error prone PCR, mutator bacterial strains (Low et al., *J. Mol. Biol.* 260, 359-68, 1996), and saturation mutagenesis (Nishimiya et al.,. *J. Biol. Chem.* 275:12813-20, 2000; Chowdhury, P. S. *Methods Mol. Biol.* 178, 269-85, 2002) are typical examples of stochastic mutagenesis methods (Rajpal et al., *Proc Natl Acad Sci USA.* 102:8466-71, 2005). Nonstochastic techniques often use alanine-scanning or site-directed mutagenesis to generate limited collections of specific variants. Some methods are described in further detail below.

Affinity Maturation Via Panning Methods—

Affinity maturation of recombinant antibodies is commonly performed through several rounds of panning of candidate antibodies in the presence of decreasing amounts of antigen. Decreasing the amount of antigen per round selects the antibodies with the highest affinity to the antigen thereby yielding antibodies of high affinity from a large pool of starting material. Affinity maturation via panning is well known in the art and is described, for example, in Huls et al. (*Cancer Immunol Immunother.* 50:163-71, 2001). Methods of affinity maturation using phage display technologies are described elsewhere herein and known in the art (see e.g., Daugherty et al., *Proc Natl Acad Sci USA.* 97:2029-34, 2000).

Look-Through Mutagenesis—

Look-through mutagenesis (LTM) (Rajpal et al., *Proc Natl Acad Sci USA.* 102:8466-71, 2005) provides a method for rapidly mapping the antibody-binding site. For LTM, nine amino acids, representative of the major side-chain chemistries provided by the 20 natural amino acids, are selected to dissect the functional side-chain contributions to binding at every position in all six CDRs of an antibody. LTM generates a positional series of single mutations within a CDR where each "wild type" residue is systematically substituted by one of nine selected amino acids. Mutated CDRs are combined to generate combinatorial single-chain variable fragment (scFv) libraries of increasing complexity and size without becoming prohibitive to the quantitative display of all variants. After positive selection, clones with improved binding are sequenced, and beneficial mutations are mapped.

Error-Prone PCR—

Error-prone PCR involves the randomization of nucleic acids between different selection rounds. The randomization occurs at a low rate by the intrinsic error rate of the polymerase used but can be enhanced by error-prone PCR (Zaccolo et al.,. J. Mol. Biol. 285:775-783, 1999) using a polymerase having a high intrinsic error rate during transcription (Hawkins et al., J Mol Biol. 226:889-96, 1992). After the mutation cycles, clones with improved affinity for the antigen are selected using routine methods in the art.

DNA Shuffling—

Nucleic acid shuffling is a method for in vitro or in vivo homologous recombination of pools of shorter or smaller polynucleotides to produce variant polynucleotides. DNA shuffling has been described in U.S. Pat. No. 6,605,449, U.S. Pat. No. 6,489,145, WO 02/092780 and Stemmer, *Proc. Natl. Acad. Sci. USA,* 91:10747-51 (1994). Generally, DNA shuffling is comprised of 3 steps: fragmentation of the genes to be shuffled with DNase I, random hybridization of fragments and reassembly or filling in of the fragmented gene by PCR in the presence of DNA polymerase (sexual PCR), and amplification of reassembled product by conventional PCR.

DNA shuffling differs from error-prone PCR in that it is an inverse chain reaction. In error-prone PCR, the number of polymerase start sites and the number of molecules grows exponentially. In contrast, in nucleic acid reassembly or shuffling of random polynucleotides the number of start sites and the number (but not size) of the random polynucleotides decreases over time.

In the case of an antibody, DNA shuffling allows the free combinatorial association of all of the CDR1s with all of the CDR2s with all of the CDR3s, for example. It is contemplated that multiple families of sequences can be shuffled in the same reaction. Further, shuffling generally conserves the relative order, such that, for example, CDR1 will not be found in the position of CDR2. Rare shufflants will contain a large number of the best (e.g. highest affinity) CDRs and these rare shufflants may be selected based on their superior affinity.

The template polynucleotide which may be used in DNA shuffling may be DNA or RNA. It may be of various lengths depending on the size of the gene or shorter or smaller polynucleotide to be recombined or reassembled. Preferably, the template polynucleotide is from 50 bp to 50 kb. The template polynucleotide often should be double-stranded.

It is contemplated that single-stranded or double-stranded nucleic acid polynucleotides having regions of identity to the template polynucleotide and regions of heterology to the template polynucleotide may be added to the template polynucleotide, during the initial step of gene selection. It is also contemplated that two different but related polynucleotide templates can be mixed during the initial step.

Alanine Scanning—

Alanine scanning mutagenesis can be performed to identify hypervariable region residues that contribute significantly to antigen binding. Cunningham and Wells, (*Science* 244:1081-1085, 1989). A residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody muteins are screened for the desired activity.

Computer-Aided Design—

Alternatively, or in addition, it may be beneficial to analyze a crystal structure of the antigen-antibody complex to identify contact points between the antibody and antigen, or to use computer software to model such contact points. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Affinity maturation involves preparing and screening antibody muteins that have substitutions within the CDRs of a parent antibody and selecting muteins that have improved biological properties such as binding affinity relative to the parent antibody. A convenient way for generating such substitutional muteins is affinity maturation using phage display. Briefly, several hypervariable region sites (e.g. 6-7 sites) are mutated to generate all possible amino substitutions at each site. The antibody muteins thus generated are displayed in a monovalent fashion from filamentous phage particles as fusions to the gene III product of M13 packaged within each particle. The phage-displayed muteins are then screened for their biological activity (e.g. binding affinity).

Alanine scanning mutagenesis can be performed to identify hypervariable region residues that contribute significantly to antigen binding. Alternatively, or in addition, it may be beneficial to analyze a crystal structure of the antigen-antibody complex to identify contact points between the antibody and antigen. Such contact residues and neighboring residues are candidates for substitution according to the techniques elaborated herein. Once such muteins are generated, the panel of muteins is subjected to screening as described herein and antibodies with superior properties in one or more relevant assays may be selected for further development.

Altered Effector Function

Other modifications of the antibody are contemplated. For example, it may be desirable to modify the antibody of the invention with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148: 2918-2922 (1992). Homodimeric antibodies with enhanced activity may also be prepared using heterobifunctional cross-linkers as described in Wolff et al., Cancer Research 53: 2560-2565 (1993). Alternatively, an antibody can be engineered which has dual Fc regions and may thereby have enhanced complement lysis and ADCC capabilities. See Stevenson et al., *Anti-Cancer Drug Design* 3: 219-230 (1989). In addition, it has been shown that sequences within the CDR can cause an antibody to bind to MHC Class II and trigger an unwanted helper T-cell response. A conservative substitution can allow the antibody to retain binding activity yet lose its ability to trigger an unwanted T-cell response. Also see Steplewski et al., Proc Natl Acad Sci USA. 1988; 85(13): 4852-6, incorporated herein by reference in its entirety, which described chimeric antibodies wherein a murine variable region was joined with human gamma 1, gamma 2, gamma 3, and gamma 4 constant regions.

In certain embodiments of the invention, it may be desirable to use an antibody fragment, rather than an intact antibody, to increase tumor penetration, for example. In this case, it may be desirable to modify the antibody fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, e.g., WO96/32478).

The salvage receptor binding epitope preferably constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fc region and transferred to the C.sub.L region or V.sub.L region, or both, of the antibody fragment. See also International applications WO 97/34631 and WO 96/32478 which describe Fc variants and their interaction with the salvage receptor.

Thus, antibodies of the invention may comprise a human Fc portion, a human consensus Fc portion, or a mutein thereof that retains the ability to interact with the Fc salvage receptor, including muteins in which cysteines involved in disulfide bonding are modified or removed, and/or in which the a met is added at the N-terminus and/or one or more of the N-terminal 20 amino acids are removed, and/or regions that interact with complement, such as the C1q binding site, are removed, and/or the ADCC site is removed [see, e.g., Molec. Immunol. 29 (5): 633-9 (1992)]. Antibodies of the IgG class may also include a different constant region, e.g. an IgG2 antibody may be modified to display an IgG1 or IgG4 constant region.

In the case of IgG1, modifications to the constant region, particularly the hinge or CH2 region, may increase or decrease effector function, including ADCC and/or CDC activity. In other embodiments, an IgG2 constant region is modified to decrease antibody-antigen aggregate formation. In the case of IgG4, modifications to the constant region, particularly the hinge region, may reduce the formation of half-antibodies. In specific exemplary embodiments, mutating the IgG4 hinge sequence Cys-Pro-Ser-Cys to the IgG1 hinge sequence Cys-Pro-Pro-Cys is provided.

Previous studies mapped the binding site on human and murine IgG for FcR primarily to the lower hinge region composed of IgG residues 233-239. Other studies proposed additional broad segments, e.g. Gly316-Lys338 for human Fc receptor I, Lys274-Arg301 and Tyr407-Arg416 for human Fc receptor III, or found a few specific residues outside the lower hinge, e.g. Asn297 and Glu318 for murine IgG2b interacting with murine Fc receptor II. The report of the 3.2-Å crystal structure of the human IgG1 Fc fragment with human Fc receptor IIIA delineated IgG1 residues Leu234-Ser239, Asp265-Glu269, Asn297-Thr299, and Ala327-Ile332 as involved in binding to Fc receptor IIIA. It has been suggested based on crystal structure that in addition to the lower hinge (Leu234-Gly237), residues in IgG CH2 domain loops FG (residues 326-330) and BC (residues 265-271) might play a role in binding to Fc receptor IIA. See Shields et al., J. Biol. Chem., 276(9):6591-6604 (2001), incorporated by reference herein in its entirety. Mutation of residues within Fc receptor binding sites can result in altered effector function, such as altered ADCC or CDC activity, or altered half-life. As described above, potential mutations include insertion, deletion or substitution of one or more residues, including substitution with alanine, a conservative substitution, a non-conservative substitution, or replacement with a corresponding amino acid residue at the same position from a different IgG subclass (e.g. replacing an IgG1 residue with a corresponding IgG2 residue at that position).

Shields et al. reported that IgG1 residues involved in binding to all human Fc receptors are located in the CH2 domain proximal to the hinge and fall into two categories as follows: 1) positions that may interact directly with all FcR include Leu234-Pro238, Ala327, and Pro329 (and possibly Asp265); 2) positions that influence carbohydrate nature or position include Asp265 and Asn297. The additional IgG1 residues that affected binding to Fc receptor II are as follows: (largest effect) Arg255, Thr256, Glu258, Ser267, Asp270, Glu272, Asp280, Arg292, Ser298, and (less effect) His268, Asn276, His285, Asn286, Lys290, Gln295, Arg301, Thr307, Leu309, Asn315, Lys322, Lys326, Pro331, Ser337, Ala339, Ala378, and Lys414. A327Q, A327S, P329A, D265A and D270A reduced binding. In addition to the residues identified above for all FcR, additional IgG1 residues that reduced binding to Fc receptor IIIA by 40% or more are as follows: Ser239, Ser267 (Gly only), His268, Glu293, Gln295, Tyr296, Arg301, Val303, Lys338, and Asp376. Muteins that improved binding to FcRIIIA include T256A, K290A, S298A, E333A, K334A, and A339T. Lys414 showed a 40% reduction in binding for FcRIIA and FcRIIB, Arg416 a 30% reduction for FcRIIA and FcRIIIA, Gln419 a 30% reduction to FcRIIA and a 40% reduction to FcRIIB, and Lys360 a 23% improvement to FcRIIIA. See also Presta et al., Biochem. Soc. Trans. (2001) 30, 487-490.

For example, U.S. Pat. No. 6,194,551, incorporated herein by reference in its entirety, describes muteins with altered effector function containing mutations in the human IgG Fc region, at amino acid position 329, 331 or 322 (using Kabat numbering), some of which display reduced C1q binding or CDC activity. As another example, U.S. Pat. No. 6,737,056, incorporated herein by reference in its entirety, describes muteins with altered effector or Fc-gamma-receptor binding containing mutations in the human IgG Fc region, at amino acid position 238, 239, 248, 249, 252, 254, 255, 256, 258, 265, 267, 268, 269, 270, 272, 276, 278, 280, 283, 285, 286, 289, 290, 292, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439 (using Kabat numbering), some of which display receptor binding profiles associated with reduced ADCC or CDC activity. Of these, a mutation at amino acid position 238, 265, 269, 270, 327 or 329 are stated to reduce binding to FcRI, a mutation at amino acid position 238, 265, 269, 270, 292, 294, 295, 298, 303, 324, 327, 329, 333, 335, 338, 373, 376, 414, 416, 419, 435, 438 or 439 are stated to reduce binding to FcRII, and a mutation at amino acid position 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 is stated to reduce binding to FcRIII.

U.S. Pat. No. 5,624,821, incorporated by reference herein in its entirety, reports that C1q binding activity of an murine antibody can be altered by mutating amino acid residue 318, 320 or 322 of the heavy chain and that replacing residue 297 (Asn) results in removal of lytic activity.

United States Application Publication No. 20040132101, incorporated herein by reference in its entirety, describes muteins with mutations at amino acid positions 240, 244, 245, 247, 262, 263, 266, 299, 313, 325, 328, or 332 (using Kabat numbering) or positions 234, 235, 239, 240, 241, 243, 244, 245, 247, 262, 263, 264, 265, 266, 267, 269, 296, 297, 298, 299, 313, 325, 327, 328, 329, 330, or 332 (using Kabat numbering), of which mutations at positions 234, 235, 239, 240, 241, 243, 244, 245, 247, 262, 263, 264, 265, 266, 267, 269, 296, 297, 298, 299, 313, 325, 327, 328, 329, 330, or 332 may reduce ADCC activity or reduce binding to an Fc gamma receptor.

Chappel et al., Proc Natl Acad Sci USA. 1991; 88(20): 9036-40, incorporated herein by reference in its entirety, report that cytophilic activity of IgG1 is an intrinsic property of its heavy chain CH2 domain. Single point mutations at any of amino acid residues 234-237 of IgG1 significantly lowered or abolished its activity. Substitution of all of IgG1 residues 234-237 (LLGG) into IgG2 and IgG4 were required to restore full binding activity. An IgG2 antibody containing the entire ELLGGP (SEQ ID NO: 103) sequence (residues 233-238) was observed to be more active than wild-type IgG1.

Isaacs et al., J Immunol. 1998; 161(8):3862-9, incorporated herein by reference in its entirety, report that mutations within a motif critical for Fc gammaR binding (glutamate 233 to proline, leucine/phenylalanine 234 to valine, and leucine 235 to alanine) completely prevented depletion of target cells. The mutation glutamate 318 to alanine eliminated effector function of mouse IgG2b and also reduced the potency of human IgG4.

Armour et al., Mol Immunol. 2003; 40(9):585-93, incorporated by reference herein in its entirety, identified IgG1 muteins which react with the activating receptor, FcgammaRIIa, at least 10-fold less efficiently than wildtype IgG1 but whose binding to the inhibitory receptor, FcgammaRIIb, is only four-fold reduced. Mutations were made in the region of amino acids 233-236 and/or at amino acid positions 327, 330 and 331. See also WO 99/58572, incorporated by reference herein in its entirety.

Xu et al., J Biol Chem. 1994; 269(5):3469-74, incorporated by reference herein in its entirety, report that mutating IgG1 Pro331 to Ser markedly decreased C1q binding and virtually eliminated lytic activity. In contrast, the substitution of Pro for Ser331 in IgG4 bestowed partial lytic activity (40%) to the IgG4 Pro331 mutein.

Schuurman et al., Mol Immunol. 2001; 38(1):1-8, incorporated by reference herein in its entirety, report that mutating one of the hinge cysteines involved in the inter-heavy chain bond formation, Cys226, to serine resulted in a more stable inter-heavy chain linkage. Mutating the IgG4 hinge sequence Cys-Pro-Ser-Cys to the IgG1 hinge sequence Cys-Pro-Pro-Cys also markedly stabilizes the covalent interaction between the heavy chains.

Angal et al., Mol Immunol. 1993; 30(1):105-8, incorporated by reference herein in its entirety, report that mutating the serine at amino acid position 241 in IgG4 to proline (found at that position in IgG1 and IgG2) led to the production of a homogeneous antibody, as well as extending serum half-life and improving tissue distribution compared to the original chimeric IgG4.

The invention also contemplates production of antibody molecules with altered carbohydrate structure resulting in altered effector activity, including antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity [Yamane-Ohnuki et al., Biotechnol Bioeng. 2004 Sep. 5; 87(5):614-22]. Similar effects can be accomplished through decreasing the activity of this or other enzymes in the fucosylation pathway, e.g., through siRNA or antisense RNA treatment, engineering cell lines to knockout the enzyme(s), or culturing with selective glycosylation inhibitors [Rothman et al., Mol Immunol. 1989 December; 26(12):1113-23]. Some host cell strains, e.g. Lec13 or rat hybridoma YB2/0 cell line naturally produce antibodies with lower fucosylation levels. Shields et al., J Biol Chem. 2002 Jul. 26; 277(30):26733-40; Shinkawa et al., J Biol Chem. 2003 Jan. 31; 278(5):3466-73. An increase in the level of bisected carbohydrate, e.g. through recombinantly producing antibody in cells that overexpress GnTIII enzyme, has also been determined to increase ADCC activity. Umana et al., Nat Biotechnol. 1999 February; 17(2):176-80. It has been predicted that the absence of only one of the two fucose residues may be sufficient to increase ADCC activity. Ferrara et al., J Biol Chem. 2005 Dec. 5; [Epub ahead of print]

Other Covalent Modifications

Covalent modifications of the antibody are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, .alpha.-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R-N.dbd.C.dbd.N-R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the .alpha.-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Hakimuddin, et al. Arch. Biochem. Biophys. 259: 52 (1987) and by Edge et al. Anal. Biochem., 118: 131 (1981). Enzymatic cleavage of carbohydrate moieties on antibodies can be achieved by the use of a variety of endo- and exo-glycosidases as described by Thotakura et al. Meth. Enzymol. 138: 350 (1987).

Another type of covalent modification of the antibody comprises linking the antibody to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640,835; 4,496,689; 4,301,144; 4,670,417; 4,791,192, 4,179,337, 4,766,106, 4,179,337, 4,495,285, 4,609,546 or EP 315 456.

Each antibody molecule may be attached to one or more (i.e. 1, 2, 3, 4, 5 or more) polymer molecules. Polymer molecules are preferably attached to antibodies by linker molecules. The polymer may, in general, be a synthetic or naturally occurring polymer, for example an optionally substituted straight or branched chain polyalkene, polyalkenylene or polyoxyalkylene polymer or a branched or unbranched polysaccharide, e.g. homo- or hetero-polysaccharide. Preferred polymers are polyoxyethylene polyols and polyethylene glycol (PEG). PEG is soluble in water at room temperature and has the general formula: R(O—CH2-CH2)n O—R where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/antibody of the present invention. Preferred polymers, and methods to attach them to peptides, are shown in U.S. Pat. Nos. 4,766,106; 4,179,337; 4,495,285; and 4,609, 546 which are all hereby incorporated by reference in their entireties.

Gene Therapy

Delivery of a therapeutic antibody to appropriate cells can be effected via gene therapy ex vivo, in situ, or in vivo by use of any suitable approach known in the art, including by use of physical DNA transfer methods (e.g., liposomes or chemical treatments) or by use of viral vectors (e.g., adenovirus, adeno-associated virus, or a retrovirus). For example, for in vivo therapy, a nucleic acid encoding the desired antibody, either alone or in conjunction with a vector, liposome, or precipitate may be injected directly into the subject, and in some embodiments, may be injected at the site where the expression of the antibody compound is desired. For ex vivo treatment, the subject's cells are removed, the nucleic acid is introduced into these cells, and the modified cells are returned to the subject either directly or, for example, encapsulated within porous membranes which are implanted into the patient. See, e.g. U.S. Pat. Nos. 4,892,538 and 5,283,187. There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, and calcium phosphate precipitation. A commonly used vector for ex vivo delivery of a nucleic acid is a retrovirus.

Other in vivo nucleic acid transfer techniques include transfection with viral vectors (such as adenovirus, Herpes simplex I virus, or adeno-associated virus) and lipid-based systems. The nucleic acid and transfection agent are optionally associated with a microparticle. Exemplary transfection agents include calcium phosphate or calcium chloride co-precipitation, DEAE-dextran-mediated transfection, quaternary ammonium amphiphile DOTMA ((dioleoyloxypropyl) trimethylammonium bromide, commercialized as Lipofectin by GIBCO-BRL))(Felgner et al, (1987) Proc. Natl. Acad. Sci. USA 84, 7413-7417; Malone et al. (1989) Proc. Natl Acad. Sci. USA 86 6077-6081); lipophilic glutamate diesters with pendent trimethylammonium heads (Ito et al. (1990) Biochem. Biophys. Acta 1023, 124-132); the metabolizable parent lipids such as the cationic lipid dioctadecylamido glycyl-spermine (DOGS, Transfectam, Promega) and dipalmitoylphosphatidyl ethanolamylspermine (DPPES)(J. P. Behr (1986) Tetrahedron Lett. 27, 5861-5864; J. P. Behr et al. (1989) Proc. Natl. Acad. Sci. USA 86, 6982-6986); metabolizable quaternary ammonium salts (DOTB, N-(1-[2, 3-dioleoyloxy]propyl)-N,N,N-trimethylammonium methyl-sulfate (DOTAP)(Boehringer Mannheim), polyethylene-imine (PEI), dioleoyl esters, ChoTB, ChoSC, DOSC) (Leventis et al. (1990) Biochim. Inter. 22, 235-241); 3beta [N—(N',N'-dimethylaminoethane)-carbamoyl]cholesterol (DC-Chol), dioleoylphosphatidyl ethanolamine (DOPE)/ 3beta[N—(N',N'-dimethylaminoethane)-carbamoyl]choles-terolDC-Chol in one to one mixtures (Gap et al., (1991) Biochim. Biophys. Acta 1065, 8-14), spermine, spermidine, lipopolyamines (Behr et al., Bioconjugate Chem, 1994, 5: 382-389), lipophilic polylysines (LPLL) (Zhou et al., (1991) Biochim. Biophys. Acta 939, 8-18), [[(1,1,3,3-tetramethylbu-tyl)cre-soxy]ethoxy]ethyl]dimethylbenzylammonium hydroxide (DEBDA hydroxide) with excess phosphatidyl-choline/cholesterol (Ballas et al., (1988) Biochim. Biophys. Acta 939, 8-18), cetyltrimethylammonium bromide (CTAB)/ DOPE mixtures (Pinnaduwage et al, (1989) Biochim. Biophys. Acta 985, 33-37), lipophilic diester of glutamic acid (TMAG) with DOPE, CTAB, DEBDA, didodecylammonium bromide (DDAB), and stearylamine in admixture with phos-phatidylethanolamine (Rose et al., (1991) Biotechnique 10, 520-525), DDAB/DOPE (TransfectACE, BRL), and oligoga-lactose bearing lipids. Exemplary transfection enhancer agents that increase the efficiency of transfer include, for example, DEAE-dextran, polybrene, lysosome-disruptive peptide (Ohmori N I et al, Biochem Biophys Res Commun Jun. 27, 1997; 235(3):726-9), chondroitan-based proteogly-cans, sulfated proteoglycans, polyethylenimine, polylysine (Pollard H et al. J Biol Chem, 1998 273 (13):7507-11), inte-grin-binding peptide CYGGRGDTP, linear dextran nonasac-charide, glycerol, cholesteryl groups tethered at the 3'-termi-nal internucleoside link of an oligonucleotide (Letsinger, R. L. 1989 Proc Natl Acad Sci USA 86: (17):6553-6), lysophos-phatide, lysophosphatidylcholine, lysophosphatidylethano-lamine, and 1-oleoyl lysophosphatidylcholine.

In some situations it may be desirable to deliver the nucleic acid with an agent that directs the nucleic acid-containing vector to target cells. Such "targeting" molecules include antibodies specific for a cell-surface membrane protein on the target cell, or a ligand for a receptor on the target cell. Where liposomes are employed, proteins which bind to a cell-surface membrane protein associated with endocytosis may be used for targeting and/or to facilitate uptake. Examples of such proteins include capsid proteins and fragments thereof tropic for a particular cell type, antibodies for proteins which undergo internalization in cycling, and proteins that target intracellular localization and enhance intracellular half-life. In other embodiments, receptor-mediated endocytosis can be used. Such methods are described, for example, in Wu et al., 1987 or Wagner et al., 1990. For review of the currently known gene marking and gene therapy protocols, see Anderson 1992. See also WO 93/25673 and the references cited therein. For additional reviews of gene therapy technology, see Friedmann, Science, 244: 1275-1281 (1989); Anderson, Nature, supplement to vol. 392, no 6679, pp. 25-30 (1998); Verma, Scientific American: 68-84 (1990); and Miller, Nature, 357: 455460 (1992).

Screening Methods

Another aspect of the present invention is directed to methods of identifying antibodies which modulate (i.e., decrease) activity of a PRLR comprising contacting a PRLR with an antibody, and determining whether the antibody modifies activity of the PRLR. The activity in the presence of the test antibody is compared to the activity in the absence of the test antibody. Where the activity of the sample containing the test antibody is lower than the activity in the sample lacking the test antibody, the antibody will have inhibited activity. Effective therapeutics depend on identifying efficacious agents devoid of significant toxicity. Antibodies may be screened for binding affinity by methods known in the art. For example, gel-shift assays, Western blots, radiolabeled competition assay, co-fractionation by chromatography, co-precipitation, cross linking, ELISA, surface plasmon resonance (e.g., BIA-CORE®), time-resolved fluorometry (e.g., DELFIA) and the like may be used, which are described in, for example, Current Protocols in Molecular Biology (1999), Current Protocols in Immunology (2007) John Wiley & Sons, NY, which are incorporated herein by reference in their entirety. In addition, surface plasmon resonance (e.g., BIACORE®) may be employed to assess competition between two antibodies (See, e.g., Example 7 below). Time-resolved fluorometry (e.g., DELFIA) also may be employed to assess the level of competition between two antibodies. For example, a microplate based competitive screening DELFIA® assay (Perkin Elmer) may be performed according to protocols provided by the manufacturer.

To initially screen for antibodies which bind to the desired epitope on the target antigen, a routine cross-blocking assay such as that described in Antibodies, A Laboratory Manual, Cold Spring Harbor Laboratory, Ed Harlow and David Lane (1988), can be performed. Routine competitive binding assays may also be used, in which the unknown antibody is characterized by its ability to inhibit binding of target to a target-specific antibody of the invention. Intact antigen, fragments thereof such as the extracellular domain, or linear epitopes can be used. Epitope mapping is described in Champe et al., J. Biol. Chem. 270: 1388-1394 (1995).

In one variation of an in vitro binding assay, the invention provides a method comprising the steps of (a) contacting an immobilized PRLR with a candidate antibody and (b) detecting binding of the candidate antibody to the PRLR. In an alternative embodiment, the candidate antibody is immobilized and binding of PRLR is detected. Immobilization is accomplished using any of the methods well known in the art, including covalent bonding to a support, a bead, or a chromatographic resin, as well as non-covalent, high affinity interaction such as antibody binding, or use of streptavidin/biotin binding wherein the immobilized compound includes a biotin moiety. Detection of binding can be accomplished (i) using a radioactive label on the compound that is not immobilized, (ii) using a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

Antibodies that modulate (i.e., increase, decrease, or block) the activity of the target antigen may be identified by incubating a candidate antibody with target antigen (or a cell expressing target antigen) and determining the effect of the candidate antibody on the activity or expression of the target antigen. The activity in the presence of the test antibody is compared to the activity in the absence of the test antibody. Where the activity of the sample containing the test antibody is lower than the activity in the sample lacking the test antibody, the antibody will have inhibited activity. The selectivity of an antibody that modulates the activity of a target antigen polypeptide or polynucleotide can be evaluated by comparing its effects on the target antigen to its effect on other related compounds.

In particular exemplary embodiments, it is contemplated that the antibodies are tested for their effect in a cultured cell system to determine their ability to prevent PRLR dimerization and/or neutralize PRLR in inducing STAT5 and/or MAPK and/or AKT phosphorylation or other indicators of PRLR signaling. Additionally, cellular assays including proliferation assays, soft agar assays, and/or cytotoxicity assays as described herein may be used to evaluate a particular PRLR antibody.

The biological activity of a particular antibody, or combination of antibodies, may be evaluated in vivo using a suitable animal model. For example, xenogenic cancer models wherein human cancer cells are introduced into immune compromised animals, such as nude or SCID mice, may be used. Efficacy may be predicted using assays which measure inhibition of tumor formation, tumor regression or metastasis, and the like.

The invention also comprehends high throughput screening (HTS) assays to identify antibodies that interact with or inhibit biological activity (i.e., inhibit enzymatic activity, binding activity, intracellular signaling, etc.) of target antigen. HTS assays permit screening of large numbers of compounds in an efficient manner. Cell-based HTS systems are contemplated to investigate the interaction between target antigen and its binding partners. HTS assays are designed to identify "hits" or "lead compounds" having the desired property, from which modifications can be designed to improve the desired property.

In another embodiment of the invention, high throughput screening for antibody fragments or CDRs with 1, 2, 3 or more modifications to amino acids within the CDRs having suitable binding affinity to a target antigen polypeptide is employed.

Combination Therapy

Having identified more than one antibody that is effective in an animal model, it may be further advantageous to mix two or more such antibodies together (which bind to the same or different target antigens) to provide still improved efficacy. Compositions comprising one or more antibody may be administered to persons or mammals suffering from, or predisposed to suffer from, cancer. Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

Although antibody therapy may be useful for all stages of cancers, antibody therapy may be particularly appropriate in advanced and metastatic cancers. Combining the antibody therapy method with a chemotherapeutic or radiation regimen may be preferred in patients that have not received chemotherapeutic treatment, whereas treatment with the antibody therapy may be indicated for patients who have received one or more chemotherapies. Additionally, antibody therapy can also enable the use of reduced dosages of concomitant chemotherapy, particularly in patients that do not tolerate the toxicity of the chemotherapeutic agent very well.

The methods of the invention contemplate the administration of single antibodies, as well as combinations, or "cocktails", of different antibodies. Such antibody cocktails may have certain advantages inasmuch as they contain antibodies which exploit different effector mechanisms or combine directly cytotoxic antibodies with antibodies that rely on immune effector functionality. Such antibodies in combination may exhibit synergistic therapeutic effects. By way of example, the methods of the invention contemplate administering antibodies to M-CSF, RANKL, TAXOTERE™ (docetaxel) HERCEPTIN™ (trastuzumab) AVASTIN™ (bevacizumab) ERBITUX™ (cetuximab) or anti-EGFR antibodies, and Tamoxifen.

A cytotoxic agent refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic. A non-cytotoxic agent may include a bead, liposome, matrix or particle (see, e.g., U.S. Patent Publications 2003/0028071 and 2003/0032995 which are incorporated by reference herein). Such agents may be conjugated, coupled, linked or associated with an antibody according to the invention.

Cancer chemotherapeutic agents include, without limitation, alkylating agents, such as carboplatin and cisplatin; nitrogen mustard alkylating agents; nitrosourea alkylating agents, such as carmustine (BCNU); antimetabolites, such as methotrexate; folinic acid; purine analog antimetabolites, mercaptopurine; pyrimidine analog antimetabolites, such as fluorouracil (5-FU) and gemcitabine (GEMZAR® (gemcitabine)); hormonal antineoplastics, such as goserelin, leuprolide, and tamoxifen; natural antineoplastics, such as aldesleukin, interleukin-2, docetaxel, etoposide (VP-16), interferon alfa, paclitaxel (TAXOL® (paclitaxel)), and tretinoin (ATRA); antibiotic natural antineoplastics, such as bleomycin, dactinomycin, daunorubicin, doxorubicin, daunomycin and mitomycins including mitomycin C; and vinca alkaloid natural antineoplastics, such as vinblastine, vincristine, vindesine; hydroxyurea; aceglatone, adriamycin, ifosfamide, enocitabine, epitiostanol, aclarubicin, ancitabine, nimustine, procarbazine hydrochloride, carboquone, carboplatin, carmofur, chromomycin A3, antitumor polysaccharides, antitumor platelet factors, cyclophosphamide (CYTOXIN® (Cyclophosphamide)), Schizophyllan, cytarabine (cytosine arabinoside), dacarbazine, thioinosine, thiotepa, tegafur, dolastatins, dolastatin analogs such as auristatin, CPT-11 (irinotecan), mitozantrone, vinorelbine, teniposide, aminopterin, carminomycin, esperamicins (See, e.g., U.S. Pat. No. 4,675,187), neocarzinostatin, OK-432, bleomycin, furtulon, broxuridine, busulfan, honvan, peplomycin, bestatin (UBENIMEX® (Bestatin)), interferon-β, mepitiostane, mitobronitol, melphalan, laminin peptides, lentinan, Coriolus versicol or extract, tegafur/uracil, estramustine (estrogen/mechlorethamine).

Further, additional agents used as therapy for cancer patients include EPO, G-CSF, ganciclovir; antibiotics, leuprolide; meperidine; zidovudine (AZT); interleukins 1 through 18, including mutants and analogues; interferons or cytokines, such as interferons α, β, and γ hormones, such as luteinizing hormone releasing hormone (LHRH) and analogues and, gonadotropin releasing hormone (GnRH); growth factors, such as transforming growth factor-β (TGF-β), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-α & β (TNF-α & β); invasion inhibiting factor-2 (IIF-2); bone morphogenetic proteins 1-7 (BMP 1-7); somatostatin; thymosin-α-1; γ-globulin; superoxide dismutase (SOD); EGFR (epidermal growth factor receptor) antagonists, such as for example Cetuximab and Gefitinib; PR (progesterone receptor) antagonists and modulators such as mifepristone and onapristone; aromataose inhibitors such as for example Anastrozole, Exemestane and Letrozole; anti-estrogen agents, estrogen receptor anatagonists and modulators, such as for example Tamoxifen, Toremifene and Fulvestrant; complement factors; anti-angiogenesis factors; antigenic materials; and prodrugs.

Prodrug refers to a precursor or derivative form of a pharmaceutically active substance that is less cytotoxic or non-cytotoxic to tumor cells compared to the parent drug and is capable of being enzymatically activated or converted into an active or the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use herein include, but are not limited to, those chemotherapeutic agents described above.

Administration and Preparation

The antibodies of the invention may be formulated into pharmaceutical compositions comprising a carrier suitable for the desired delivery method. Suitable carriers include any material which, when combined with antibodies, retains the desired activity of the antibody and is nonreactive with the subject's immune systems. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Therapeutic formulations of the antibody are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

The antibody is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. In addition, the antibody is suitably administered by pulse infusion, particularly with declining doses of the antibody. Preferably the dosing is given by injections, most preferably intravenous or subcutaneous injections. Other administration methods are contemplated, including topical, particularly transdermal, transmucosal, rectal, oral or local administration e.g. through a catheter placed close to the desired site.

For nasal administration, the pharmaceutical formulations and medicaments may be a spray or aerosol containing an appropriate solvent(s) and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (leuprolide acetate for depot suspension) (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions. Other strategies known in the art may be used.

The formulations of the invention may be designed to be short-acting, fast-releasing, long-acting, or sustained-releasing as described herein. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Besides those representative dosage forms described above, pharmaceutically acceptable excipients and carries are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

Specific dosages may be adjusted depending on conditions of disease, the age, body weight, general health conditions, genotype, sex, and diet of the subject, dose intervals, administration routes, excretion rate, and combinations of drugs. Any of the above dosage forms containing effective amounts are well within the bounds of routine experimentation and therefore, well within the scope of the instant invention.

Antibodies of the invention will often be prepared substantially free of other naturally occurring immunoglobulins or other biological molecules. Preferred antibodies will also exhibit minimal toxicity when administered to a mammal afflicted with, or predisposed to suffer from cancer.

The compositions of the invention may be sterilized by conventional, well known sterilization techniques. The resulting solutions may be packaged for use or filtered under aseptic conditions and lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride and stabilizers (e.g., 1 20% maltose, etc.).

The antibodies of the present invention may also be administered via liposomes, which are small vesicles composed of various types of lipids and/or phospholipids and/or surfactant which are useful for delivery of a drug (such as the antibodies disclosed herein and, optionally, a chemotherapeutic agent). Liposomes include emulsions, foams, micelles, insoluble monolayers, phospholipid dispersions, lamellar layers and the like, and can serve as vehicles to target the antibodies to a particular tissue as well as to increase the half life of the composition. A variety of methods are available for preparing liposomes, as described in, e.g., U.S. Pat. Nos. 4,837,028 and 5,019,369, which patents are incorporated herein by reference.

Liposomes containing the antibody are prepared by methods known in the art, such as described in Epstein et al., Proc. Natl. Acad. Sci. USA 82: 3688 (1985); Hwang et al., Proc. Natl Acad. Sci. USA 77: 4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257: 286-288 (1982) via a disulfide interchange reaction. A chemotherapeutic agent (such as Doxorubicin) is optionally contained within the liposome [see, e.g., Gabizon et al., J. National Cancer Inst. 81(19): 1484 (1989)].

The concentration of antibody in these compositions can vary widely, i.e., from less than about 10%, usually at least about 25% to as much as 75% or 90% by weight and will be selected primarily by fluid volumes, viscosities, etc., in accordance with the particular mode of administration selected. Actual methods for preparing orally, topically and parenterally administrable compositions will be known or apparent to those skilled in the art and are described in detail in, for example, Remington's Pharmaceutical Science, 19th ed., Mack Publishing Co., Easton, Pa. (1995), which is incorporated herein by reference.

Determination of an effective amount of a composition of the invention to treat disease in a patient can be accomplished through standard empirical methods which are well known in the art.

Compositions of the invention are administered to a mammal already suffering from, or predisposed to or at risk of, for example, breast, prostate, or lung cancer, in an amount sufficient to prevent or at least partially arrest the development of disease. An amount adequate to accomplish this is defined as a "therapeutically effective dose." Effective amounts of an antibody will vary and depend on the severity of the disease and the weight and general state of the patient being treated, but generally range from about 1.0 μg/kg to about 100 mg/kg body weight. Exemplary doses may range from about 10 μg/kg to about 30 mg/kg, or from about 0.1 mg/kg to about 20 mg/kg or from about 1 mg/kg to about 10 mg/kg per application. Antibody may also be dosed by body surface area (e.g. up to 4.5 g/square meter). Other exemplary doses of antibody include up to 8 g total in a single administration (assuming a body weight of 80 kg or body surface area of 1.8 square meters).

Administration may be by any means known in the art. For example, antibody may be administered by one or more separate bolus administrations, or by short or long term infusion over a period of, e.g., 5, 10, 15, 30, 60, 90, 120 minutes or more. Following an initial treatment period, and depending on the patient's response and tolerance of the therapy, maintenance doses may be administered, e.g., weekly, biweekly, every 3 weeks, every 4 weeks, monthly, bimonthly, every 3 months, or every 6 months, as needed to maintain patient response. More frequent dosages may be needed until a desired suppression of disease symptoms occurs, and dosages may be adjusted as necessary. The progress of this therapy is easily monitored by conventional techniques and assays. The therapy may be for a defined period or may be chronic and continue over a period of years until disease progression or death.

Single or multiple administrations of the compositions can be carried out with the dose levels and pattern being selected by the treating physician. For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

In any event, the formulations should provide a quantity of therapeutic antibody over time that is sufficient to exert the desired biological activity, e.g. prevent or minimize the severity of cancer. The compositions of the present invention may be administered alone or as an adjunct therapy in conjunction with other therapeutics known in the art for the treatment of such diseases.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The therapeutically effective amount of the antibody to be administered will be governed by such considerations, and is the minimum amount necessary to prevent, ameliorate, or treat the target-mediated disease, condition or disorder. Such amount is preferably below the amount that is toxic to the host or renders the host significantly more susceptible to infections.

The antibody need not be, but is optionally formulated with one or more agents currently used to prevent or treat the disorder in question. The effective amount of such other agents depends on the amount of antibody present in the formulation, the type of disease, condition or disorder or treatment, and other factors discussed above. These are generally used in the same dosages and with administration routes as used hereinbefore or about from 1 to 99% of the heretofore employed dosages.

In another embodiment of the invention, there is provided an article of manufacture containing materials useful for the treatment of the desired condition. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody of the invention. The label on, or associated with, the container indicates that the composition is used for treating the condition of choice. The article of manufacture may further comprise a second container containing a second therapeutic agent (including any of the second therapeutic agents for diseases discussed herein or known in the art). The article of manufacture may further comprise another container containing a pharmaceutically-acceptable buffer, such as phosphate-buffered saline, Ringer's solution or dextrose solution for reconstituting a lyophilized antibody formulation. It may further include other materials desirable from a commercial and user standpoint, including other buffers, diluents, filters, needles, syringes, and package inserts with instructions for use.

Immunotherapy

Antibodies useful in treating patients having cancers include those which are capable of initiating a potent immune response against the tumor and those which are capable of direct cytotoxicity. Antibodies conjugated to cytotoxic agents may be used to target the cytotoxic agents to tumor tissues expressing PRLR. Alternatively, antibodies may elicit tumor cell lysis by either complement-mediated or antibody-dependent cell cytotoxicity (ADCC) mechanisms, both of which require an intact Fc portion of the immunoglobulin molecule for interaction with effector cell Fc receptor sites or complement proteins. In addition, antibodies that exert a direct biological effect on tumor growth are useful in the practice of the invention. Potential mechanisms by which such directly cytotoxic antibodies may act include inhibition of cell growth, modulation of cellular differentiation, modulation of tumor angiogenesis factor profiles, and the induction of apoptosis. The mechanism by which a particular antibody exerts an anti-tumor effect may be evaluated using any number of in vitro assays designed to determine ADCC, ADMMC, complement-mediated cell lysis, and so forth, as is generally known in the art.

In one embodiment, immunotherapy is carried out using antibodies that bind to PRLR and inhibit activation of PRLR.

Anti-PRLR antibodies may be administered in their "naked" or unconjugated form, or may be conjugated directly to other therapeutic or diagnostic agents, or may be conjugated indirectly to carrier polymers comprising such other therapeutic or diagnostic agents.

Antibodies can be detectably labeled through the use of radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are well known in the art; for example, see (Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

Conjugation of antibody moieties is described in U.S. Pat. No. 6,306,393. General techniques are also described in Shih et al., Int. J. Cancer 41:832-839 (1988); Shih et al., Int. J. Cancer 46:1101-1106 (1990); and Shih et al., U.S. Pat. No. 5,057,313. This general method involves reacting an antibody component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer may be, for example, an aminodextran or polypeptide of at least 50 amino acid residues. Various techniques for conjugating a drug or other agent to the carrier polymer are known in the art. A polypeptide carrier can be used instead of aminodextran, but the polypeptide carrier should have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and conjugate.

Alternatively, conjugated antibodies can be prepared by directly conjugating an antibody component with a therapeutic agent. The general procedure is analogous to the indirect method of conjugation except that a therapeutic agent is directly attached to an oxidized antibody component. For example, a carbohydrate moiety of an antibody can be attached to polyethyleneglycol to extend half-life.

Alternatively, a therapeutic agent can be attached at the hinge region of a reduced antibody component via disulfide bond formation, or using a heterobifunctional cross-linker, such as N-succinyl 3-(2-pyridyldithio)proprionate (SPDP). Yu et al., Int. J. Cancer 56:244 (1994). General techniques for such conjugation are well-known in the art. See, for example, Wong, Chemistry Of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering and Clinical Application, Ritter et al. (eds.), pages 60-84 (Cambridge University Press 1995). A variety of bifunctional protein coupling agents are known in the art, such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Finally, fusion proteins can be constructed that comprise one or more anti-PRLR antibody moieties and another polypeptide. Methods of making antibody fusion proteins are well known in the art. See, e.g., U.S. Pat. No. 6,306,393. Antibody fusion proteins comprising an interleukin-2 moiety are described by Boleti et al., Ann. Oncol. 6:945 (1995), Nicolet et al., Cancer Gene Ther. 2:161 (1995), Becker et al., Proc. Nat'l Acad. Sci. USA 93:7826 (1996), Hank et al., Clin. Cancer Res. 2:1951 (1996), and Hu et al., Cancer Res. 56:4998 (1996).

In one embodiment, the antibodies of the invention are used as a radiosensitizer. In such embodiments, the antibodies are conjugated to a radiosensitizing agent. The term "radiosensitizer," as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Diseases that are treatable with electromagnetic radiation include neoplastic diseases, benign and malignant tumors, and cancerous cells.

The terms "electromagnetic radiation" and "radiation" as used herein include, but are not limited to, radiation having the wavelength of $10^{-20}$ to 100 meters. Preferred embodiments of the present invention employ the electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1.0 mm), and microwave radiation (1 mm to 30 cm).

Radiosensitizers are known to increase the sensitivity of cancerous cells to the toxic effects of electromagnetic radiation. Many cancer treatment protocols currently employ radiosensitizers activated by the electromagnetic radiation of X-rays. Examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin(r), benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

In another embodiment, the antibody may be conjugated to a receptor (such streptavidin) for utilization in tumor pretargeting wherein the antibody-receptor conjugate is administered to the patient, followed by removal of unbound conjugate from the circulation using a clearing agent and then administration of a ligand (e.g., avidin) which is conjugated to a cytotoxic agent (e.g., a radionuclide).

"Label" refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable. Alternatively, the label may not be detectable on its own but may be an element that is bound by another agent that is detectable (e.g. an epitope tag or one of a binding partner pair such as biotin-avidin, etc.) Thus, the antibody may comprise a label or tag that facilitates its isolation, and methods of the invention to identify antibodies include a step of isolating the antibody through interaction with the label or tag.

Exemplary therapeutic immunoconjugates comprise the antibody described herein conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate). Fusion proteins are described in further detail below.

Chelators for radiometals or magnetic resonance enhancers are well-known in the art. Typical are derivatives of ethylenediaminetetraacetic acid (EDTA) and diethylenetriaminepentaacetic acid (DTPA). These chelators typically have groups on the side chain by which the chelator can be attached to a carrier. Such groups include, e.g., benzylisothiocyanate, by which the DTPA or EDTA can be coupled to the amine group of a carrier. Alternatively, carboxyl groups or amine groups on a chelator can be coupled to a carrier by activation or prior derivatization and then coupling, all by well-known means.

Boron addends, such as carboranes, can be attached to antibody components by conventional methods. For example, carboranes can be prepared with carboxyl functions on pendant side chains, as is well known in the art. Attachment of such carboranes to a carrier, e.g., aminodextran, can be achieved by activation of the carboxyl groups of the carboranes and condensation with amines on the carrier to produce an intermediate conjugate. Such intermediate conjugates are then attached to antibody components to produce therapeutically useful immunoconjugates, as described below.

A polypeptide carrier can be used instead of aminodextran, but the polypeptide carrier should have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, copolymers thereof, and mixed polymers of these amino acids and others, e.g., serines, to confer desirable solubility properties on the resultant loaded carrier and immunoconjugate.

Conjugation of the intermediate conjugate with the antibody component is effected by oxidizing the carbohydrate portion of the antibody component and reacting the resulting aldehyde (and ketone) carbonyls with amine groups remaining on the carrier after loading with a drug, toxin, chelator, immunomodulator, boron addend, or other therapeutic agent. Alternatively, an intermediate conjugate can be attached to an oxidized antibody component via amine groups that have been introduced in the intermediate conjugate after loading with the therapeutic agent. Oxidation is conveniently effected either chemically, e.g., with $NaIO_4$ or other glycolytic reagent, or enzymatically, e.g., with neuraminidase and galactose oxidase. In the case of an aminodextran carrier, not all of the amines of the aminodextran are typically used for loading a therapeutic agent. The remaining amines of aminodextran condense with the oxidized antibody component to form Schiff base adducts, which are then reductively stabilized, normally with a borohydride reducing agent.

Analogous procedures are used to produce other immunoconjugates according to the invention. Loaded polypeptide carriers preferably have free lysine residues remaining for condensation with the oxidized carbohydrate portion of an antibody component. Carboxyls on the polypeptide carrier can, if necessary, be converted to amines by, e.g., activation with DCC and reaction with an excess of a diamine.

The final immunoconjugate is purified using conventional techniques, such as sizing chromatography on Sephacryl S-300 or affinity chromatography using one or more CD84Hy epitopes.

Alternatively, immunoconjugates can be prepared by directly conjugating an antibody component with a therapeutic agent. The general procedure is analogous to the indirect method of conjugation except that a therapeutic agent is directly attached to an oxidized antibody component.

It will be appreciated that other therapeutic agents can be substituted for the chelators described herein. Those of skill in the art will be able to devise conjugation schemes without undue experimentation.

As a further illustration, a therapeutic agent can be attached at the hinge region of a reduced antibody component via disulfide bond formation. For example, the tetanus toxoid peptides can be constructed with a single cysteine residue that is used to attach the peptide to an antibody component. As an alternative, such peptides can be attached to the antibody component using a heterobifunctional cross-linker, such as N-succinyl 3-(2-pyridyldithio)proprionate (SPDP). Yu et al., Int. J. Cancer 56:244 (1994). General techniques for such conjugation are well-known in the art. See, for example, Wong, Chemistry Of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230

(Wiley-Liss, Inc. 1995); Price, "Production and Characterization of Synthetic Peptide-Derived Antibodies," in Monoclonal Antibodies: Production, Engineering and Clinical Application, Ritter et al. (eds.), pages 60-84 (Cambridge University Press 1995).

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionuclide to the antibody (see, e.g., WO94/11026).

As described above, carbohydrate moieties in the Fc region of an antibody can be used to conjugate a therapeutic agent. However, the Fc region may be absent if an antibody fragment is used as the antibody component of the immunoconjugate. Nevertheless, it is possible to introduce a carbohydrate moiety into the light chain variable region of an antibody or antibody fragment. See, for example, Leung et al., J. Immunol. 154:5919 (1995); Hansen et al., U.S. Pat. No. 5,443,953. The engineered carbohydrate moiety is then used to attach a therapeutic agent.

In addition, those of skill in the art will recognize numerous possible variations of the conjugation methods. For example, the carbohydrate moiety can be used to attach polyethyleneglycol in order to extend the half-life of an intact antibody, or antigen-binding fragment thereof, in blood, lymph, or other extracellular fluids. Moreover, it is possible to construct a "divalent immunoconjugate" by attaching therapeutic agents to a carbohydrate moiety and to a free sulfhydryl group. Such a free sulfhydryl group may be located in the hinge region of the antibody component.

Antibody Fusion Proteins

The present invention contemplates the use of fusion proteins comprising one or more antibody moieties and another polypeptide, such as an immunomodulator or toxin moiety. Methods of making antibody fusion proteins are well known in the art. See, e.g., U.S. Pat. No. 6,306,393. Antibody fusion proteins comprising an interleukin-2 moiety are described by Boleti et al., Ann. Oncol. 6:945 (1995), Nicolet et al., Cancer Gene Ther. 2:161 (1995), Becker et al., Proc. Nat'l Acad. Sci. USA 93:7826 (1996), Hank et al., Clin. Cancer Res. 2:1951 (1996), and Hu et al., Cancer Res. 56:4998 (1996). In addition, Yang et al., Hum. Antibodies Hybridomas 6:129 (1995), describe a fusion protein that includes an F(ab')$_2$ fragment and a tumor necrosis factor alpha moiety.

Methods of making antibody-toxin fusion proteins in which a recombinant molecule comprises one or more antibody components and a toxin or chemotherapeutic agent also are known to those of skill in the art. For example, antibody-*Pseudomonas* exotoxin A fusion proteins have been described by Chaudhary et al., Nature 339:394 (1989), Brinkmann et al., Proc. Nat'l Acad. Sci. USA 88:8616 (1991), Batra et al., Proc. Nat'l Acad. Sci. USA 89:5867 (1992), Friedman et al., J. Immunol. 150:3054 (1993), Wels et al., Int. J. Can. 60:137 (1995), Fominaya et al., J. Biol. Chem. 271:10560 (1996), Kuan et al., Biochemistry 35:2872 (1996), and Schmidt et al., Int. J. Can. 65:538 (1996). Antibody-toxin fusion proteins containing a diphtheria toxin moiety have been described by Kreitman et al., Leukemia 7:553 (1993), Nicholls et al., J. Biol. Chem. 268:5302 (1993), Thompson et al., J. Biol. Chem. 270:28037 (1995), and Vallera et al., Blood 88:2342 (1996). Deonarain et al., Tumor Targeting 1:177 (1995), have described an antibody-toxin fusion protein having an RNase moiety, while Linardou et al., Cell Biophys. 24-25:243 (1994), produced an antibody-toxin fusion protein comprising a DNase I component. Gelonin was used as the toxin moiety in the antibody-toxin fusion protein of Wang et al., Abstracts of the 209th ACS National Meeting, Anaheim, Calif., Apr. 2-6, 1995, Part 1, BIOT005. As a further example, Dohlsten et al., Proc. Nat'l Acad. Sci. USA 91:8945 (1994), reported an antibody-toxin fusion protein comprising Staphylococcal enterotoxin-A.

Illustrative of toxins which are suitably employed in the preparation of such conjugates are ricin, abrin, ribonuclease, DNase I, Staphylococcal enterotoxin-A, pokeweed antiviral protein, gelonin, diphtherin toxin, Pseudomonas exotoxin, and Pseudomonas endotoxin. See, for example, Pastan et al., Cell 47:641 (1986), and Goldenberg, Calif.—A Cancer Journal for Clinicians 44:43 (1994). Other suitable toxins are known to those of skill in the art.

Antibodies of the present invention may also be used in ADEPT by conjugating the antibody to a prodrug-activating enzyme which converts a prodrug (e.g., a peptidyl chemotherapeutic agent, See WO81/01145) to an active anti-cancer drug. See, for example, WO88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as abzymes, can be used to convert the prodrugs of the invention into free active drugs (See, e.g., Massey, Nature 328: 457-458 (1987)). Antibody-abzyme conjugates can be prepared as described herein for delivery of the abzyme to a tumor cell population.

The enzymes of this invention can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (See, e.g., Neuberger et al., Nature 312: 604-608 (1984))

Non-Therapeutic Uses

The antibodies of the invention may be used as affinity purification agents for target antigen or in diagnostic assays for target antigen, e.g., detecting its expression in specific cells, tissues, or serum. The antibodies may also be used for in vivo diagnostic assays. Generally, for these purposes the antibody is labeled with a radionuclide (such as $^{111}$In, $^{99}$Tc, $^{14}$C, $^{131}$I, $^{125}$I, $^{3}$H, $^{32}$P or $^{35}$S) so that the tumor can be localized using immuno scintiography.

The antibodies of the present invention may be employed in any known assay method, such as competitive binding assays, direct and indirect sandwich assays, such as ELISAs, and immunoprecipitation assays. Zola, Monoclonal Antibodies: A Manual of Techniques, pp. 147-158 (CRC Press, Inc. 1987). The antibodies may also be used for immunohistochemistry, to label tumor samples using methods known in the art.

As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

The invention is illustrated by the following examples, which are not intended to be limiting in any way.

EXAMPLES

Example 1

Preparation of ECD, S1 and S2 Domain Fragments of PRLR

Recombinant expression and purification of fragments of PRLR corresponding to the extracellular domain (ECD, amino acids 25-234 of SEQ ID NO: 2), the S1 domain (amino acids 25-125 of SEQ ID NO: 2), and the S2 domain (amino acids 126-234 of SEQ ID NO: 2) of PRLR was carried out as follows. Expression constructs for insect expression of ECD, S1 and S2 were designed as shown in Table 2, and primers were designed for cloning the fragments based on their respective amino acid sequences (as shown in Table 3).

TABLE 2

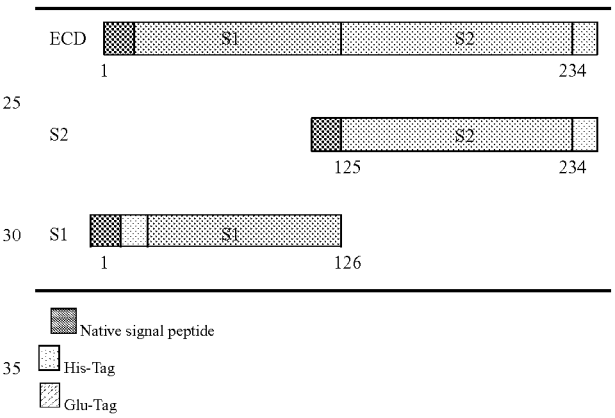

TABLE 3

| Domain | PCR primers used (F = forward; R = Reverse) | | PCR primer sequences |
|---|---|---|---|
| ECD | F1 | SEQ ID NO: 3 | GGGACAAGTTTGTACAAAAAAGCAGGCTACGAAGGAGA TATACATATGAAGGAAAATGTGGCATCTGCAA |
|  | R1 | SEQ ID NO: 4 | GGGACCACTTTGTACAAGAAAGCTGGGTTTAAGCTCCGTG ATGGTGATGGTGATGTGCTCCATCATTCATGGTGAAGTC |
| S1 | F2 | SEQ ID NO: 5 | GGGACAAGTTTGTACAAAAAAGCAGGCTTCGAAGGAGATAGA ACCATG |
|  | F3 | SEQ ID NO: 6 | CAGGCTTCGAAGGAGATAGAACCATGAAGGAAAATGTGGCAT CTGCAACC |
|  | F4 | SEQ ID NO: 7 | GAAGGAAAATGTGGCATCTGCAACCGTTTTCACTCTGCTACTT TTTCTC |
|  | F5 | SEQ ID NO: 8 | CGTTTTCACTCTGCTACTTTTTCTCAACACCTGCCTTCTGAATG GAGGAG |
|  | F6 | SEQ ID NO: 9 | CAACACCTGCCTTCTGAATGGAGGAGCACATCACCATCACCAT CACGGAG |
|  | F7 | SEQ ID NO: 10 | CACATCACCATCACCATCACGGAGCTCAGTTACCTCCTGGAAA ACCTGAG |
|  | R2 | SEQ ID NO: 11 | GGGACCACTTTGTACAAGAAAGCTGGGTTCACTGAACTATGTAAGTC ACGTCCAC |
| S2 | F8 | SEQ ID NO: 12 | GGGACAAGTTTGTACAAAAAAGCAGGCTTCGAAGGAGATAGA ACCATG |

TABLE 3-continued

| Domain | PCR primers used (F = forward; R = Reverse) | PCR primer sequences |
| --- | --- | --- |
| F9 | SEQ ID NO: 13 | CAGGCTTCGAAGGAGATAGAACCATGAAGGAAAATGTGGCATCTGCAACC |
| F10 | SEQ ID NO: 14 | GAAGGAAAATGTGGCATCTGCAACCGTTTTCACTCTGCTACTTTTTCTC |
| F11 | SEQ ID NO: 15 | CGTTTTCACTCTGCTACTTTTTCTCAACACCTGCCTTCTGAATGTTCA |
| F12 | SEQ ID NO: 16 | TCTCAACACCTGCCTTCTGAATGTTCAGCCAGACCCTCCTTTGGAGCTG |
| R3 | SEQ ID NO: 17 | CGTGATGGTGATGGTGATGTGCTCCATCATTCATGGTGAAGTCACTAGG |
| R4 | SEQ ID NO: 18 | CAAGAAAGCTGGGTTTAAGCTCCGTGATGGTGATGGTGATGTGCTCC |
| R5 | SEQ ID NO: 19 | GGGACCACTTTGTACAAGAAAGCTGGGTTTAAGCTCC |

For cloning of S1 and S2 domains, a nested PCR approach was adopted to incorporate tags and to engineer the 3'/5' region. For S1, there are 6 forward nested primers and 1 reverse primer for cloning. For S2, there are 5 forward nested primers and 3 reverse primers for cloning.

PCR amplification was carried out using PFUULTRA™ Hotstart PCR Master Mix (Stratagene) according to manufacturer's recommendation. Template used for amplification is PRLR ECD fragment cloned in pDEST3218 (data not shown). The ECD PCR product is cloned into BlueBac4.5/V5-His TOPO-TA (Invitrogen) using the topoisomerase cloning strategy. The S1 and S2 PCR products are cloned using Gateway Technology (Invitrogen) into in-house adapted pAcMP3. The final selected clones were confirmed by double-strand sequencing. 10-20 ug of DNAs was prepared for insect transfection.

The recombinant constructs were used to express the respective PRLR fragments in insect cells as follows. Baculovirus was isolated by plaque purification of a co-transfection of plasmid DNA encoding the extracellular domain of PRLR with SAPPHIRE™ genomic *Autographa californica* DNA. Recombinant virus was amplified and used to infect Tn5 insect cells at densities ranging from $1 \times 10^6$-$1.5 \times 10^6$ cells per ml, moi range of 2-10 in a 10 L (working volume) wave-bioreactor. Following 48 hour infection, cells and supernatant were collected, centrifuged and the supernatant prepared for concentration. Supernatant was clarified on a 0.45 um hollow fiber cartridge before 5× concentration with tangential flow 10 kDa MW cut-off membrane. Prior to protein purification, supernatant was filter sterilized w/1 L, 0.2 um pore vacuum flasks.

Similar methods were used to express the S1 and S2 domains in insect cells, except that S1 fragment was not concentrated before purification and S2 fragment was concentrated on a 5 kDa MW cartridge.

PRLR fragments were purified as follows. Insect cell-culture supernatants containing expressed PRLR ECD or subdomains was received from the expression group neat or concentrated up to 10× using a stacked membrane cassette apparatus (Pall Filtron) with a 1 or 5 kD nominal molecular weight cut-off. When practical, supernatants were filtered through a 0.2 micron filter. Supernatants were loaded directly onto PBS-equilibrated columns.

His-tagged proteins were purified on 1- or 5-mL HisTrap columns (GE Healthcare) at the manufacturer's recommended flow rates. Glu-tagged protein was purified on an immobilized anti-glu monoclonal antibody column prepared as follows: purified anti-glu monoclonal antibody in PBS, at concentrations from 3-10 mg/mL, was conjugated to Affi-gel 10 (Bio-Rad), an n-hydroxysuccinimide activated agarose gel, per manufacturer's instructions. Anti-glu agarose was packed into an XK 16 column (GE Healthcare) and run at a linear flow rate of 15-30 cm/hr.

Elution of protein of the HisTrap columns was by a 20 column volume gradient elution from buffer A (PBS) to buffer B (PBS+0.25 M imidazole (IX-0005, EM Merck) pH 7.4). Elution of protein from the anti-glu column was by PBS containing 0.1 mg/mL of the peptide EYMPTD, which competes with the Glu-Glu epitope. Fractions are examined by SDS-PAGE and Western blot or mass spectrometry and pooled appropriately.

Pooled PRLR ECD or subdomains were further purified by size exclusion chromatography using a Superdex 75 26/60 column (GE Healthcare) equilibrated in PBS and run at 2.5 mL/min. No more than 10 mL was loaded onto these columns. Fractions were examined by SDS-PAGE and pooled appropriately.

Example 2

Isolation of Target-Specific Antibodies from Human Antibody Phage Display Libraries To isolate a panel of antibodies able to neutralize the activity of human PRLR, three human antibody phage display libraries, expressing scFv fragments, were investigated in parallel. The target used for the library panning was the soluble extracellular domain (ECD) of the prolactin receptor (human prolactin receptor amino acids 25-234) prepared as described above in Example 1. The receptor was biotinylated (NHS-LC biotin, Pierce) and soluble panning was performed on the biotinylated ECD.

Selection of target specific antibody from phage display was carried out according to methods described by Marks et al. (*Methods Mol Biol.* 248:161-76, 2004). Briefly, the phage display library was incubated with 50 pmols of the biotinylated ECD at room temperature for 1 hr and the complex formed was then captured using 100 μl of Streptavidin beads suspension (DYNABEADS® M-280 Streptavidin, Invitrogen). Non specific phages were removed by washing the beads with wash buffer (PBS+5% Milk). Bound phages were eluted with 0.5 ml of 100 nM Triethylamine (TEA) and immediately neutralized by addition of an equal volume of 1M TRIS-Cl pH 7.4. Eluted phage pool was used to infect TG1 *E coli* cells growing in logarithmic phase, and phagemid was rescued as described (*Methods Mol Biol.* 248:161-76, 2004). Selection was repeated for a total of three rounds. Single colonies obtained from TG1 cells infected with eluted phage from the third round of panning were screened for binding activity in an ELISA assay. Briefly, single colonies obtained from the TG1 cell infected with eluted phage were used to inoculate media in 96-well plates. Microcultures were grown to an $OD_{600}$=0.6 at which point expression of soluble antibody fragment was induced by addition of 1 mM IPTG following overnight culture in a shaker incubator at 30° C. Bacteria were spun down and periplasmic extract was prepared and used to detect antibody binding activity to ECD immobilized on 96-well microplates (96-well flat bottom Immunosorb plates, Nunc) following standard ELISA protocol provided by the microplate manufacturer.

The affinities of the anti-Prolactin Receptor (PRLR) antibodies for binding to the recombinant extracellular domain (ECD) were estimated using the BIACORE® 2000 and used for affinity ranking of antibodies. A Protein A/G capture surface was used for the human scFv-Fc fusions and a rabbit anti-mouse IgG-Fc (RAM-Fc) antibody capture surface was used for the antibodies produced by hybridomas. Both the Protein A/G and the RAM-Fc capture chips were CM5 sensor chips with maximal levels of capture molecule (either Protein A/G or RAM-Fc) immobilized on all four flow cells via standard EDC-NHS amine coupling chemistries according to the recommended protocol from BIACORE® Inc. The running buffer was HBS-EP (BIACORE®, Inc.), the temperature was set at 25° C., and the flow rate was initially 10 μL/min. Purified antibodies were diluted into HBS-EP to approximate concentrations between 1-3 μg/mL, and injected over the capture chips for 1 to 2 minutes. The flow rate was increased to 25 to 30 μL/min. The recombinant ECD of PRLR was diluted to 1 μg/mL and injected for 5 to 6 minutes with a 10 minute dissociation.

Fits were performed using BIAEvaluation software and used to calculate kinetic association and dissociation rate constants ($k_{on}$ and $k_{off}$, respectively). The 1:1 Langmuir interaction model with mass transport correction was used to perform the simultaneous ka/kd fit on each sample. Several samples were fit at the same time with the Rmax, $k_{on}$, and $k_{off}$ parameters set to fit local. When baseline drift occurred, the drifting baseline model was used with the drift value set to constant and entered manually. Drift values varied from −0.03 to +0.05 RU/second.

Antibody binding was also assessed by measuring binding to prolactin receptor expressing cells using Fluorescent Activated Cell Sorting (FACS) analysis and Fluorometric Microvolume Assay Technology (FMAT) (Swartzman et al., *Anal Biochem.* 271:143-51, 1999). Clones that showed binding by either FACS or FMAT assays were sequence analyzed, and clones encoding unique heavy chain CDR3 and light chain CDR3 protein sequences were reformatted to scFv-Fc as described in Example 3 below. These scFv-Fc were tested for ability to inhibit PRLR-induced ERK1/2 phosphorylation and PRLR-induced proliferation of a BaF3/PRLR cell line, as described in Examples 5 and 6 below. Selected antibodies were further characterized for binding to the ECD, S1 and S2, as well as for relative competition between pairs of antibodies for binding to PRLR ECD, as described in Example 7. Data for selected antibodies is displayed below in Table 4

TABLE 4

| Antibody | pERK1/2 inhibition IC50 | Proliferation inhibition IC50 for BaF3/PRLR | Affinity or Equilibrium Dissociation Constant $K_D$ (nM) | Domain specificity | Epitope bin (antibodies in same bin compete for binding to PRLR) |
|---|---|---|---|---|---|
| XPA.06.158 | 0.01 | 0.06 | 0.7 | S1 | 4.5 |
| XPA.06.167 | 0.04 | 0.14 | 4 | S1 | 3.8 |
| XPA.06.178 | 0.09 | 0.23 | 20 | S1 | 3.8 |
| XPA.06.145 | 0.30 | 0.77 | 10 | S1 | 4 |
| XPA.06.217 | 0.35 | 1.18 | 7 | S1 | 7 |
| XHA.06.983 | 0.11 | 0.1 | 0.1 | S? | 6 |
| XHA.06.189 | 0.2 | 0.15 | <0.1 | S1 | 3.8 |
| XHA.06.275 | 0.5 | 1.31 | 0.4 | S2 | 5 |
| XHA.06.567 | 0.65 | 7.06 | 0.8 | S2 | 6.5 |

Example 3

Reformatting of Clones to scFv-Fc Format

For each unique scFv clone identified in Example 2, the cDNA encoding the scFv fragment is amplified by PCR from the phage display vector and ligated into a mammalian expression vector, which is a modification of XOMA's proprietary expression vector (described in WO 2004/033693, encoding either the kappa (κ), lambda (λ) or gamma-2 (γ2) constant region genes), allowing expression of each antibody in an scFv-Fc protein, where the Fc portion of the protein represents the CH2 and CH3 domain of the IgG1 molecule. Construction of scFv-Fc fusion proteins is well known in the art, for example see Fredericks et al, *Protein Eng Des Sel.* 2004 January; 17(1):95-106, Powers et al, *J Immunol Methods.* 2001 May 1; 251(1-2):123-35, or Shu et al, *Proc. Nat. Acad. Sci. USA* 1993, 90, 7995-7998. U.S. Pat. No. 5,892,019 also describes the construction of the Fc fusion protein vector and the expression of scFv-Fc fusion proteins.

Expression of the fusion protein is performed by transfection of 293E suspension cells with Lipofectamine 2000 (Invitrogen), using the manufacturer's instructions. After five days, the cells are removed by centrifugation and the scFv-Fc fusion is purified from the supernatant using protein A sepharose (GE Healthcare) using the manufacturer's suggested protocol.

Example 4

Identification of Target-Specific Antibodies Secreted by Murine Hybridomas

Mouse antibodies against the extra-cellular domain (ECD) of the human Prolactin receptor (PRLR) were generated as follows. Six Balb/C mice were immunized via subcutaneous injection with recombinant PRLR extra-cellular domain (described above). The mice received 10 injections over a 28 day period. Four days after the final injection the mice were sacrificed and the draining lymph nodes were harvested. After suspending cells from the lymph nodes they were fused with the mouse myeloma cell line P3xAg8.653 by electrocell fusion using a BTX ECM2001 Electro-Cell Manipulator (Harvard Apparatus).

Following the fusion the cells were plated out into approximately 40 96-well plates. After 12 days the plates were screened by ELISA against the recombinant ECD and in an FMAT. The FMAT assay used a CHO cell line stably transfected to express a high level of PRLR receptor.

Selected hybridomas were tested for ability to inhibit PRLR-induced ERK1/2 phosphorylation and PRLR-induced proliferation of a BaF3/PRLR cell line, as described in Examples 5 and 6 below. Selected antibodies were further characterized for binding to recombinant ECD, S1 and S2, as well as for relative competition between pairs of antibodies for binding to PRLR ECD as described in Example 7. Data for selected antibodies is displayed above in Table 4.

Example 5

Determination of Antibody Effect on ERK1/2 Phosphorylation

Following a 5 hour serum starvation, T47D cells were seeded in microtiter plates in complete growth medium for 24 hours at 37° C. Cells were washed twice with phosphate buffered saline (PBS) and incubated with antibodies diluted in serum-free media containing 0.1% BSA for 30 minutes at 37° C. The final starting concentration of the antibodies was 40 ug/ml. Media was removed and prolactin diluted in serum-free media containing 0.1% BSA was added to a final concentration of 30 ng/ml. Cells were incubated with prolactin for 30 minutes at 37° C. followed by two washes with ice cold PBS. Standard lysis buffer containing detergents, chelators, and various protease and phosphatase inhibitors was added to generate cell lysates. The levels of phosphorylated ERK1/2 (pERK1/2) were measured using standard ELISA according to instructions of DUOSET® IC Phospho-ERK1/ERK2, R&D Systems, Inc. Results of a representative assay are displayed in FIGS. 2, 3 and 4 and results of assay for selected antibodies are shown above in Table 4.

FIG. 7A-7C shows the VH and VL amino acid sequences of antibodies that had greater than 80% inhibition in the pERK assay.

Example 6

Determination of Antibody Effect on Proliferation of PRL-Responsive Cell Lines BaF3/PRLR cells were generated by electroporating the murine pro-B cell line BaF3 with an expression vector containing the full-length human PRLR and a neomycin resistance cassette. Cells were selected for 7 days in media supplemented with G418 (1 mg/ml) and rmIL-3 (10 ng/ml), followed by a 7 day selection period in rhPRL (1 ug/ml) without G418 or IL-3. Over a 14 day period, the media PRL concentration was reduced stepwise until a maintenance level of 50 ng/ml was reached. On the day of the experiment, $1\times10^4$ cells were seeded into each well of a flat bottom 96 well plate. Antibodies (in scFv-Fc fusion format) were added to wells at a concentration of 10 ug/ml, with and without 50 ng/ml rhPRL. Plates were incubated for 48 hr and analyzed using CellTiter Glo reagent. Samples were run in triplicate, agonism was assessed by cell proliferation induced by antibodies in the absence of PRL while antagonism was determined by cell proliferation in the presence of PRL. Results of this proliferation assay for selected antibodies are shown above in Table 4.

In order to analyze PRL-induced proliferation and inhibition of proliferation by anti-PRLR antibodies, T47D or MCF7-NCI cells were split at a density of $1\times10^6$ cells per ml of regular growth media (phenol red-free RPMI/10% FCS) into a T75 flask (12 ml total volume). 72 hrs after split, cells were trypsinized, counted, and seeded at a density of 5K per well (T47D) or 20K per well (MCF7) of a flat bottom 96 well plate (100 ul per well). MCF7 cells were seeded in serum-free and phenol red-free RPMI, T47D cells were seeded in either serum-free RPMI or RPMI containing 10% charcoal-stripped serum. 24 hrs after seeding, PRL and anti-PRLR antibodies were added to wells (50 ul, 3× concentrated). After 72 hrs of incubation, $^3$[H] thymidine (1 μci per well) was added to the plate for a minimum of 6 hrs in a 37° incubator. Cells were harvested using trypsin and a Tomtec 96 well plate cell harvester. Filters were then transferred to a Trilux luminometer and analyzed (1 min counts). Results of the proliferation study in FIG. 5 show that scFv inhibits the prolactin-mediated increase in proliferation.

Example 7

Measurement of Binding Affinity and Competition Via BIACORE

BIACORE analysis as described above in Example 2 was repeated to determine relative binding of selected antibodies to ECD, S1 and S2 domains of PRLR as described above, except that the S1, S2, or ECD proteins were injected at 10 μg/mL for 2 minutes at 15 μL/minute. Data from this assay were collected as report points (resonance units (RU)) by the BIACORE® control software, and normalized by dividing the amount of antigen bound by the amount of antibody captured. Data are shown in Table 5 below.

TABLE 5

Normalized S1, S2 and ECD binding by anti-PRLR antibodies.

| | PRLR Fragment Bound (RU bound/RU Ab Captured) | | |
|---|---|---|---|
| Sample | S1 | S2 | ECD |
| XPA.06.145 | 3.0% | −0.8% | 4.8% |
| XPA.06.158 | 20.5% | 0.1% | 28.2% |
| XPA.06.167 | 23.7% | 0.1% | 35.0% |
| XPA.06.178 | 16.4% | 0.0% | 20.5% |
| XPA.06.217 | 19.4% | 0.4% | 25.8% |
| XHA.06.567 | 0.9% | 16.7% | 31.1% |
| XHA.06.983 | −2.2% | −2.5% | 27.4% |
| XHA.06.275 | 0.0% | 13.4% | 26.2% |
| XHA.06.189 | 16.9% | 0.2% | 31.6% |

The affinities of the purified antibodies were determined by performing a series of injections on the BIACORE® 2000.

The affinity and rate constants generated are relevant for these antibodies binding the recombinant extra-cellular domain (ECD) of the prolactin receptor (PRLR) at 25° C. in an HBS-EP buffer system. A CM5 sensor chip with approximately 5000-1000 RU of Protein A/G was prepared via standard EDC-NHS amine coupling chemistries according to the recommended protocol from BIACORE® Inc. and used to capture the antibodies. The purified antibodies were diluted to roughly 1 ug/mL in HBS-EP buffer for capture. Injection time required to give between 250 and 400 RU of antibody capture was determined. The capture of the antibodies for the kinetic analysis was performed by injecting the antibodies at 10 uL/minute for 1.5 to 3 minutes, depending on results of the capture level optimization.

For the kinetic analysis, the flow rate was set at 40 uL/minute. Five concentrations of PRLR ECD were prepared in a 1:3 serial dilution from either 148 nM (4 ug/mL) or 37 nM (1 ug/mL). Each concentration plus a buffer control (zero concentration) were injected in duplicate. The data sets were double referenced and fit globally using a 1:1 Langmuir binding interaction model. This same analysis was also performed for the IgG reformatted construct of XPA.06.167 for both IgG1 and IgG2 constructs.

Kinetic constants and affinities for binding of selected antibodies to ECD of PRLR is displayed in Table 6 below.

TABLE 6

Affinity analysis results

| ANTIBODY | $k_{on}$ (1/Ms) | $k_{off}$ (1/s) | $K_D$ (M) |
| --- | --- | --- | --- |
| XPA.06.131 | 3.4E+04 | 7.3E−05 | 2.1E−09 |
| XPA.06.158 | 1.1E+05 | 7.3E−05 | 7.0E−10 |
| XPA.06.141 | 6.3E+04 | 5.3E−04 | 8.4E−09 |
| XPA.06.147 | 5.5E+05 | 5.3E−03 | 9.8E−09 |
| XPA.06.167 IgG1 | 2.3E+05 | 6.0E−04 | 2.6E−09 |
| XPA.06.167 IgG2 | 2.1+05 | 5.72E−04 | 2.7E−09 |

Similar procedures were used to determine kinetic constants and affinities for additional antibodies (Summarized in Table 7, below).

TABLE 7

| | kon | koff | KD |
| --- | --- | --- | --- |
| XHA.06.642 | 9.2E+05 | 8.6E−04 | 934 pM |
| XHA.06.275 | 1.0E+06 | 3.4E−04 | 337 pM |
| XHA.06.983 | 7.3E+05 | 3.2E−04 | 43 pM |
| chXHA.06.642 | 6.5E+04 | 5.2E−04 | 801 pM |
| chXHA.06.275 | 1.1E+06 | 2.2E−04 | 196 pM |
| chXHA.06.983 | 2.4E+05 | 1.0E−05 | 42 pM |

Relative competition or interference between pairs of antibodies (e.g., pairing analysis) for binding to PRLR was determined as follows in a serial competition assay strategy. In this approach, one antibody is immobilized onto a sensor chip, either directly or through a capture agent, and allowed to bind the ECD as it is injected over the immobilized antibody. When necessary, excess captured agent is blocked by injecting a high concentration of irrelevant IgG (e.g., when testing two murine antibodies using a rabbit-anti-mouse IgG capture surface). The antibody to be tested for competition is subsequently injected, and its ability to bind the ECD captured by the first antibody is determined. If the two antibodies bind to spatially separated epitopes on the ECD, then the second antibody should also be able to bind the ECD/first antibody complex. If the two antibodies interfere or compete, then the second antibody will not be able to bind as well, or at all, to the ECD/first antibody complex. Results of this competition analysis are displayed in Table 4 above (if two antibodies have the same epitope bin number, they will compete with each other for binding to ECD and they will exhibit the same pattern of competition against antibodies from other bins). The invention specifically contemplates the identification of other antibodies that bind to the same epitope of PRLR as any of the antibodies in the bins described herein or that compete with such antibodies for binding PRLR ECD.

Example 8

Effect on PRL-Induced PRLR, STAT5 & AKT Phosphorylation by Western Blot

The ability of selected antibodies to inhibit PRL-induced phosphorylation of STAT5 and AKT was determined as follows. Cells were seeded overnight in 6 well plates at a density of $3 \times 10^5$ cells/ml in phenol red-free RPMI/10% FBS. The following day, media was replaced with serum-free RPMI for 30 min. In some experiments, anti-PRLR or non-specific control antibodies were incubated with cells during this serum starvation period. 50 ng/ml PRL was then added to wells for 30 min, after which cells were rinsed once in PBS and lysed in a buffer consisting of 50 mM Tris-HCl, pH7.5, 150 mM NaCl, 1 mM EDTA, 1% NP-40, 1 mM Na3OV4, 50 mM NaF, 0.25% deoxycholate and protease inhibitors. Tubes were spun down at 14,000 rpm in a refrigerated microfuge and lysates were quantitated using BCA reagents. 30 μg of whole cell lysate was separated by 10% SDS-PAGE and proteins were detected using phospho-specific antibodies for STAT5A/B (Y694/Y699, Upstate) or PRLR (Y546/Y611, in-house) and ECL. Equal protein loading was determined by staining with antibodies specific for total STAT5 (BD) or PRLR (Zymed) or AKT (Cell Signalling). Results of a representative assay of effect of a PRLR-specific antibody on PRLR intracellular phosphorylation are shown in FIG. 6.

Example 9

Humanization of Murine Antibodies

This example sets out a procedure for humanization of a murine anti-PRLR antibody.

Design of Genes for Humanized PRLR Antibody Light and Heavy Chains

The VL and VH amino acid sequences for murine antibodies XHA.06.983, XHA.06.275, and XHA.06.642 are set forth in FIG. 10. The sequence of a human antibody identified using the National Biomedical Foundation Protein Identification Resource or similar database is used to provide the framework of the humanized antibody. To select the sequence of the humanized heavy chain, the murine heavy chain sequence is aligned with the sequence of the human antibody heavy chain. At each position, the human antibody amino acid is selected for the humanized sequence, unless that position falls in any one of four categories defined below, in which case the murine amino acid is selected:

(1) The position falls within a complementarity determining region (CDR), as defined by Kabat, J. Immunol., 125, 961-969 (1980);

(2) The human antibody amino acid is rare for human heavy chains at that position, whereas the murine amino acid is common for human heavy chains at that position;

(3) The position is immediately adjacent to a CDR in the amino acid sequence of the murine heavy chain; or (4) 3-dimensional modeling of the murine antibody suggests that the amino acid is physically close to the antigen binding region.

To select the sequence of the humanized light chain, the murine light chain sequence is aligned with the sequence of the human antibody light chain. The human antibody amino acid is selected at each position for the humanized sequence, unless the position again falls into one of the categories described above and repeated below:

(1) CDR's;
(2) murine amino acid more typical than human antibody;
(3) Adjacent to CDR's; or
(4) Possible 3-dimensional proximity to binding region.

The actual nucleotide sequence of the heavy and light chain genes is selected as follows:

(1) The nucleotide sequences code for the amino acid sequences chosen as described above;

(2) 5' of these coding sequences, the nucleotide sequences code for a leader (signal) sequence. These leader sequences were chosen as typical of antibodies;

(3) 3' of the coding sequences, the nucleotide sequences are the sequences that follow the mouse light chain J5 segment and the mouse heavy chain J2 segment, which are part of the murine sequence. These sequences are included because they contain splice donor signals; and (4) At each end of the sequence is an Xba I site to allow cutting at the Xba I sites and cloning into the Xba I site of a vector.

Construction of Humanized Light and Heavy Chain Genes

To synthesize the heavy chain, four oligonucleotides are synthesized using an Applied Biosystems 380B DNA synthesizer. Two of the oligonucleotides are part of each strand of the heavy chain, and each oligonucleotide overlaps the next one by about 20 nucleotides to allow annealing. Together, the oligonucleotides cover the entire humanized heavy chain variable region with a few extra nucleotides at each end to allow cutting at the Xba I sites. The oligonucleotides are purified from polyacrylamide gels.

Each oligonucleotide is phosphorylated using ATP and T4 polynucleotide kinase by standard procedures (Maniatis et al., Molecular Cloning: A Laboratory Manual, 2nd ed., Cold Spring Harbor Laboratory, Cold Spring Harbor, N.Y. (1989)). To anneal the phosphorylated oligonucleotides, they are suspended together in 40 ul of TA (33 mM Tris acetate, pH 7.9, 66 mM potassium acetate, 10 mM magnesium acetate) at a concentration of about 3.75 µM each, heated to 95° C. for 4 min. and cooled slowly to 4° C. To synthesize the complete gene from the oligonucleotides by synthesizing the opposite strand of each oligonucleotide, the following components are added in a final volume of 100 ul:

| | | |
|---|---|---|
| 10 ul | annealed oligonucleotides | |
| 0.16 mM | each deoxyribonucleotide | |
| 0.5 mM | ATP | |
| 0.5 mM | DTT | |
| 100 ug/ml | BSA | |
| 3.5 ug/ml | T4 g43 protein (DNA polymerase) | |
| 25 ug/ml | T4 g44/62 protein (polymerase accessory protein) | |
| 25 ug/ml | 45 protein (polymerase accessory protein) | |

The mixture is incubated at 37° C. for 30 min. Then 10u of T4 DNA ligase is added and incubation at 37° C. is resumed for 30 min. The polymerase and ligase are inactivated by incubation of the reaction at 70° C. for 15 min. To digest the gene with Xba I, 50 ul of 2× TA containing BSA at 200 ug/ml and DTT at 1 mM, 43 ul of water, and 50u of Xba I in 5 ul is added to the reaction. The reaction is incubated for 3 hr at 37° C., and then purified on a gel. The Xba I fragment is purified from a gel and cloned into the Xba I site of the plasmid pUC19 by standard methods. Plasmids are purified using standard techniques and sequenced using the dideoxy method.

Construction of plasmids to express humanized light and heavy chains is accomplished by isolating the light and heavy chain Xba I fragments from the pUC19 plasmid in which it had been inserted and then inserting it into the Xba I site of an appropriate expression vector which will express high levels of a complete heavy chain when transfected into an appropriate host cell.

Synthesis and Affinity of Humanized Antibody

The expression vectors are transfected into mouse Sp2/0 cells, and cells that integrate the plasmids are selected on the basis of the selectable marker(s) conferred by the expression vectors by standard methods. To verify that these cells secreted antibody that binds to PRLR, supernatant from the cells are incubated with cells that are known to express PRLR. After washing, the cells are incubated with fluorescein-conjugated goat anti-human antibody, washed, and analyzed for fluorescence on a FACSCAN cytofluorometer.

The cells producing the humanized antibody are cultured in vitro. Humanized antibody is purified to substantial homogeneity from the cell supernatants by passage through an affinity column of Protein A (Pro-Chem Inc., Littleton, Mass. or equivalent) according to standard techniques. The affinity of the humanized antibody relative to the original murine antibody is determined according to techniques known in the art.

Example 10

HUMAN ENGINEERING™ of Murine Antibodies

This example describes cloning and expression of HUMAN ENGINEERED™ antibodies, as well as purification of such antibodies and testing for binding activity.

Design of HUMAN ENGINEERED™ Sequences

HUMAN ENGINEERING™ of antibody variable domains has been described by Studnicka [See, e.g., Studnicka et al. U.S. Pat. No. 5,766,886; Studnicka et al. Protein Engineering 7: 805-814 (1994)] as a method for reducing immunogenicity while maintaining binding activity of antibody molecules. According to the method, each variable region amino acid has been assigned a risk of substitution. Amino acid substitutions are distinguished by one of three risk categories: (1) low risk changes are those that have the greatest potential for reducing immunogenicity with the least chance of disrupting antigen binding; (2) moderate risk changes are those that would further reduce immunogenicity, but have a greater chance of affecting antigen binding or protein folding; (3) high risk residues are those that are important for binding or for maintaining antibody structure and carry the highest risk that antigen binding or protein folding will be affected. Due to the three-dimensional structural role of prolines, modifications at prolines are generally considered to be at least moderate risk changes, even if the position is typically a low risk position. FIG. 10 shows the light and heavy chain variable region amino acid sequences of murine antibodies XHA.06.983, XHA.06.275, and XHA.06.642.

Variable regions of the light and heavy chains of the murine antibodies are HUMAN ENGINEERED™ using this method. Amino acid residues that are candidates for modification according to the method at low risk positions are identified by aligning the amino acid sequences of the murine variable regions with a human variable region sequence. Any human variable region can be used, including an individual VH or VL sequence or a human consensus VH or VL sequence. The amino acid residues at any number of the low risk positions, or at all of the low risk positions, can be changed.

Similarly, amino acid residues that are candidates for modification according to the method at all of the low and moderate risk positions are identified by aligning the amino acid sequences of the murine variable regions with a human variable region sequence. The amino acid residues at any number of the low or moderate risk positions, or at all of the low and moderate risk positions, can be changed.

Preparation of HUMAN ENGINEERED™ Antibody Sequences

DNA fragments encoding HUMAN ENGINEERED™ heavy and light chain V region sequences along with signal sequences (e.g., antibody-derived signal sequences) are constructed using synthetic nucleotide synthesis. DNA encoding each of the light chain V region amino acid sequences described herein is inserted into a vector containing the human Kappa or Lambda light chain constant region. DNA encoding each of the heavy chain V region amino acid sequences described herein is inserted into a vector containing the human Gamma-1, 2, 3 or 4 heavy chain constant region. All of these vectors contain a promoter (e.g., hCMV promoter) and a 3' untranslated region (e.g., mouse kappa light chain 3' untranslated region) along with additional regulatory sequences, depending on their use for transient expression or stable cell line development (US 2006/0121604).

For expression of HUMAN ENGINEERED™ antibodies using the aforementioned vectors containing variable region sequences, at least four variants may be generated from different combinations of low risk light chain, low+moderate risk light chain, low risk heavy chain, and low+moderate risk heavy chain. In those instances when moderate risk changes are not included in either or both of the light chain or heavy chain, fewer variants are correspondingly produced.

Preparation of Expression Vectors for Transient Expression

Vectors containing either the light or heavy chain genes described above are constructed for transient transfection. In addition to the HUMAN ENGINEERED™ antibody sequences, promoter and light chain 3' untranslated region described above, these vectors preferably contain the Epstein-Barr virus oriP for replication in HEK293 cells that express the Epstein-Barr virus nuclear antigen.

Transient Expression of HUMAN-ENGINEERED™ PRLR Antibody in HEK293E Cells

Separate vectors each containing oriP from the Epstein-Barr virus and the light chain or heavy chain genes described above are transfected transiently into HEK293E cells as described in US 2006/0121604. Transiently transfected cells are allowed to incubate for up to 10 days after which the supernatant is recovered and antibody purified using Protein A chromatography.

Preparation of Expression Vectors for Permanent Cell Line Development

In addition to the HUMAN ENGINEERED™ antibody sequences, promoter and light chain 3' untranslated region described above, vectors for permanent cell line development contain the selectable marker genes such as neo or his for selection of G418—or histidinol—resistant transfectants, respectively. A final vector is constructed that contains one copy of the heavy chain and one copy of the light chain coding regions.

Development of Permanently Transfected CHO-K1 Cells

The vectors described above containing one copy each of the light and heavy genes together are transfected into Ex-Cell 302-adapted CHO-K1 cells. CHO-K1 cells adapted to suspension growth in Ex-Cell 302 medium are typically transfected with linearized vector using linear polyethyleneimine (PEI). The cells are plated in 96 well plates containing Ex-Cell 302 medium supplemented with 1% FBS and G418. Clones are screened in 96 well plates and the top ~10% of clones from each transfection are transferred to deep-well 96 well plates containing Ex-Cell 302 medium supplemented with G418.

A productivity test is performed in deep-well 96 well plates in Ex-Cell 302 medium for cultures grown for 14 days at which time culture supernatants are tested for levels of secreted antibody by an immunoglobulin ELISA assay for IgG.

The top clones are transferred to shake flasks containing Ex-Cell 302 medium. Shake flask tests are performed with these clones in Ex-Cell 302 medium. The cells are grown for 14 days in 125 ml Erlenmeyer flasks containing 25 ml media. The levels of immunoglobulin polypeptide in the culture medium are determined by IgG ELISA or HPLC at the end of the incubation period. Multiple sequential transfections of the same cell line with two or three multi-unit transcription vectors results in clones and cell lines that exhibit further increases in levels of immunoglobulin production, preferably to 300 µg/ml or more.

Purification

A process for the purification of immunoglobulin polypeptides from vectors and all lines according to the invention may be designed (See, for example, US 2006/0121604). For example, according to methods well known in the art, cells are removed by filtration after termination. The filtrate is loaded onto a Protein A column (in multiple passes, if needed). The column is washed and then the expressed and secreted immunoglobulin polypeptides are eluted from the column. For preparation of antibody product, the Protein A pool is held at a low pH (pH 3 for a minimum of 30 minutes and a maximum of one hour) as a viral inactivation step. An adsorptive cation exchange step is next used to further purify the product. The eluate from the adsorptive separation column is passed through a virus retaining filter to provide further clearance of potential viral particles. The filtrate is further purified by passing through an anion exchange column in which the product does not bind. Finally, the purification process is concluded by transferring the product into the formulation buffer through diafiltration. The retentate is adjusted to a protein concentration of at least 1 mg/mL and a stabilizer is added.

Binding Activity

The PRLR binding activity of the recombinant HUMAN ENGINEERED™ antibodies is evaluated. Protein is purified from shake flask culture supernatants by passage over a protein A column followed by concentration determination by $A_{280}$. Binding assays are performed as described in other examples.

Example 11

Human Engineered Antibodies

Three of the aforementioned murine antibodies were HUMAN ENGINEERED™ generally as described in Example 10.

HUMAN ENGINEERING™ of the Prolactin Receptor Antibodies XHA.06.642 and XHA.06.275

For XHA.06.642, the heavy chain was HUMAN ENGINEERED™ at either 11 low risk or 13 low plus moderate risk positions; the light chain was HUMAN ENGINEERED™ only at low risk positions (14 changes) because all of the moderate risk positions already were human amino acids. For XHA.06.275, the heavy chain was HUMAN ENGINEERED™ at either 7 low risk or 11 low plus moderate risk positions; the light chain was HUMAN ENGINEERED™ at either 8 low risk or 10 low plus moderate risk positions.

Amino acid sequences of the HUMAN-ENGINEERED™ variable regions derived from XHA.06.642, XHA.06.275 and XHA.06.983 are shown below (CDRs underlined). These variable regions were assembled in various combinations (e.g., SEQ ID NO: 88 and SEQ ID NO: 89; SEQ ID NO: 88 and SEQ ID NO: 90; SEQ ID NO: 91 and SEQ ID NO: 93; SEQ ID NO: 91 and SEQ ID NO: 94; SEQ ID NO: 92 and SEQ ID NO: 93; or SEQ ID NO: 92 and SEQ ID NO: 94) to generate the HUMAN-ENGINEERED™ antibodies he.06.642-1, he.06.642-2, he.06.275-1, he.06.275-2, he.06.275-3, he.06.275-4.

```
he.06.642 LC Variable Region Low Risk (SEQ ID NO: 88):
DIVLTQSPDSLAVSLGERATINCKASKSVSTSGYTYMHWYQQKPGQPPKLLIYLASN
RESGVPDRFSGSGSGTDFTLTISPVQAEDVATYYCQHSGELPPSFGQGTKLEIK he.06.642 HC Variable Region Low Risk (SEQ ID NO: 89):
EVQLVESGGGLVQPGGSLRLSCAVSGFTFSSYGMSWVRQAPGKRLEWVATVSSGGT
YTYYPDSVKGRFTISRDNSKNTLYLQMNSLRAEDTAMYYCARHRGNYYATYYYAM
DYWGQGTLVTVSS he.06.642 HC Variable Region Low + Moderate Risk (SEQ ID NO: 90):
EVQLVESGGGLVQPGGSLRLSCAVSGFTFSSYGMSWVRQAPGKGLEWVATVSSGGT
YTYYPDSVKGRFTISRDNSKNTLYLQMNSLRAEDTAVYYCARHRGNYYATYYYAM
DYWGQGTLVTVSS he.06.275 LC Variable Region Low Risk (SEQ ID NO: 91):
DVQITQSPSSLSASPGDRITLTCRASKNIYKYLAWYQEKPGKTNNLLIYSGSTLHSGIP
SRFSGSGSGTDFTLTISSLQPEDFAMYYCQQHNDYPYTFGQGTKLEIK he.06.275 LC Variable Region Low + Moderate Risk (SEQ ID NO: 92):
DVQITQSPSSLSASPGDRITLTCRASKNIYKYLAWYQEKPGKANKLLIYSGSTLHSGIP
SRFSGSGSGTDFTLTISSLQPEDFAMYYCQQHNDYPYTFGQGTKLEIK he.06.275 HC Variable Region Low Risk (SEQ ID NO: 93):
DVQLQESGPGLVKPSQTLSLTCTVTGYSITSDYAWNWIRQFPGKKLEWMGYISYSGS
TSYNPSLKSRITISRDTSKNQFSLQLNSVTAADTATYFCARDYGYVFDYWGQGTTLT
VSS he.06.275 HC Variable Region Low + Moderate Risk (SEQ ID NO: 94):
QVQLQESGPGLVKPSQTLSLTCTVSGYSITSDYAWNWIRQFPGKGLEWMGYISYSGS
TSYNPSLKSRITISRDTSKNQFSLQLNSVTAADTAVYFCARDYGYVFDYWGQGTTLT
VSS he.06.983 LC Variable Region Low Risk (SEQ ID NO: 95):
DIVMTQSPDSLAVSAGERVTINCKASQGVSNDVAWFQQKPGQSPKLLIYSASTRYTG
VPDRLSGSGSGTDFTFTISSVQAEDVAVYFCQQDYTSPTFGQGTKLEIK he.06.983 LC Variable Region Low + Moderate Risk (SEQ ID NO: 96):
DIVMTQSPDSLAVSLGERVTINCKASQGVSNDVAWFQQKPGQSPKLLIYSASTRESG
VPDRLSGSGSGTDFTFTISSVQAEDVAVYFCQQDYTSPTFGQGTKLEIK he.06.983 HC Variable Region Low Risk (SEQ ID NO: 97):
DVQLVESGGGLVQPGGSRRLSCAASGFAFSSFGMQWVRQAPGKGLEWVAYISSGSS
TIYYADTVKGRFTISRDNPKNTLYLQMNSLRAEDTAMYYCVRSGRDYWGQGTLVT
VSS he.06.983 HC Variable Region Low + Moderate Risk (SEQ ID NO: 98):
EVQLVESGGGLVQPGGSRRLSCAASGFAFSSFGMQWVRQAPGKGLEWVAYISSGSS
TIYYADSVKGRFTISRDNPKNTLYLQMNSLRAEDTAVYYCVRSGRDYWGQGTLVTV
SS
```

Example 12

Expression and Purification of he.06.642 and he.06.275 Antibodies

The HUMAN ENGINEERED™ he.06.642 and he.06.275 light and heavy chain V regions were fused to human Kappa and Gamma-1 or Gamma-2 constant regions, respectively. The heavy and light chain genes then were fused to a strong promoter and efficient 3' untranslated region and cloned into transient expression vectors containing the Epstein-Bar virus origin of replication Antibodies were transiently expressed in HEK293 cells using separate plasmids encoding antibody heavy chain and light chain sequences in the various Low or Low+Moderate Risk combinations generally as described in Example 10. The ratio of heavy chain:light chain DNA was 1:2. Transfection of cells was performed with PEI at a ratio of DNA:PEI of 1:2 and a DNA concentration of 1 ug/mL. The cell density was 8e5 cells/mL. The DNA was prepared using standard Qiagen kits. The expression cultures were grown in IS293 media (Irvine Scientific) +1% low Ig FBS (Hyclone) in 2 L flasks with 400 mL media per flask. Culture conditions were 37° C., 5% $CO_2$, and agitation at 90-95 RPM. After 5-7 days in culture, the culture medium was harvested and clarified as the purification input.

Purification of chimeric and HUMAN ENGINEERED™ versions of the aforementioned antibodies was achieved in a single step by passing transient expression culture supernatant directly over a recombinant Protein A Fast Flow column (GE Healthcare). Elution of the major peak was by 0.1 mM glycine pH 3.5. Pooled material was dialyzed into PBS and concentrated in centrifugal concentrators with a nominal molecular weight cut-off of 30 kD. Final purities were >95% and overall yields were approximately 60%. The final pools were assayed for endotoxin using an Endosafe PTS LAL unit (Charles River) or the QCL-1000 Chromogenic LAL Endpoint Assay (Lonza), and the results were <0.05 EU/mg (below the limit of detection) for all the antibodies. Aggregation state of the chimeric antibody he.06.642-2 was determined to be monomeric by SEC on a Superdex 200 10/300 GL column (GE Healthcare).

chXHA.06.642 is isolated to a purity of >95% in a single chromatographic step followed by dialysis for buffer exchange. chXHA.06.642 is soluble in PBS at 3 mg/mL and no major impurities or aggregation are detected as measured by size exclusion chromatography.

Testing of Human Engineered Anti-Human PRLR Antibodies by Flow Cytometry

CHO-K1 parental and human prolactin receptor (PRLR) expressing cells were harvested, centrifuged and resuspended at approximately $5 \times 10^6$ cells/ml in 1×PBS containing 2% FBS and 0.1% sodium azide (FACS buffer). Human engineered anti-human PRLR and anti-KLH isotype control antibodies were diluted to 2× final concentration in FACS buffer and added to appropriate sample wells (50 ml/well). For secondary antibody and autofluorescence controls, 50 ml FACS buffer was added to appropriate wells. 50 ml of cell suspension was added to each sample well. Samples were incubated at 4° C. for 1 hour, washed 2× with cold FACS buffer and resuspended in FACS buffer containing PE-conjugated goat anti-human IgG (Jackson Immunoresearch, West Grove, Pa.) at a 1:100 dilution. Following a 30 minute incubation at 4° C., cells were washed 2× with cold FACS buffer, resuspended in FACS buffer containing 1 mg/ml propidium iodide (Invitrogen, San Diego, Calif.) and analyzed by flow cytometry. As shown in Table 8, the anti-PRLR antibodies bind to the PRLR expressing cells but not the parental cells.

TABLE 8

| PLRL Cell Line, clone 1G5 | | CHO-K1 Parental Cell Line | |
|---|---|---|---|
| Sample | MFI: | Sample | MFI: |
| Auto. control, 1G5 | 2.51 | Auto. control, 1G5 | 2.66 |
| GAH-PE, 1G5 | 2.6 | GAH-PE, PAR | 2.54 |
| GAM-PE, 1G5 | 2.61 | GAM-PE, PAR | 2.58 |
| MAB1167, 1G5 | 33.8 | MAB1167, PAR | 2.58 |
| KLH8.G2, 1G5 | 2.75 | KLH8.G2, PAR | 2.66 |
| he.06.642 3 G2, 1G5 | 38.5 | he.06.642-3 G2, PAR | 2.58 |
| KLH8.G1, 1G5 | 2.69 | KLH8.G1, PAR | 2.59 |
| he.06.642 3 G1 (1), 1G5 | 39.1 | he.06.642 3 G1 (1), PAR | 2.57 |
| he.06.642 3 G1 (2), 1G5 | 43 | he.06.642 3 G1 (2), PAR | 2.55 |
| chXHA.06.642(1), 1G5 | 37.3 | chXHA.06.642 (1), PAR | 2.56 |
| chXHA.06.642 (2), 1G5 | 37.3 | chXHA.06.642 (2), PAR | 2.55 |

Example 13

Affinity of HUMAN ENGINEERED™ Antibodies

Affinity of the chimerized and HUMAN ENGINEERED™ antibodies determined by Biacore analysis. Briefly, a CM5 sensor chip (Biacore) immobilized with Protein A/G (Pierce) via NHS/EDC was used to capture approximately 600 RU of antibody on the chip surface. Five concentrations of PRLR ECD beginning at 5 ug/mL (185 nM) and serially diluted at 5× dilution to 0.3 nM were injected from lowest to highest concentration in the kinetic titration injection mode, and 15 minutes of dissociation data was collected. The experiments were double-referenced, i.e. an adjacent flow cell response was subtracted automatically, and the response from a buffer injection experiment was subtracted from the experimental data set. Kinetic and derived parameters ($k_a$, $k_d$ and $K_D$) were determined by fitting to a 1:1 Langmuir model using BiaEval software customized to the kinetic titration injection mode. Affinity measurements of both chimeric and all HUMAN ENGINEERED™ antibodies against human and cynomolgus PRLR ECD are summarized in Table 9 and Table 10.

TABLE 9

| Sample | KD | kd | ka | Chi2 |
|---|---|---|---|---|
| chXHA.06.275 Human | 3.9E-10 | 2.7E-04 | 7.0E+05 | 0.574 |
| he.06.275-1 Human | 5.0E-10 | 3.1E-04 | 6.2E+05 | 0.594 |
| he.06.275-2 Human | 6.1E-10 | 3.7E-04 | 6.0E+05 | 0.532 |
| he.06.275-3 Human | 4.3E-10 | 2.7E-04 | 6.4E+05 | 0.555 |
| he.06.275-4 Human | 5.2E-10 | 3.2E-04 | 6.2E+05 | 0.69 |
| chXHA.06.275 Cyno | 1.2E-09 | 5.0E-04 | 4.3E+05 | 1.48 |
| he.06.275-1 Cyno | 1.6E-09 | 5.7E-04 | 3.6E+05 | 2.78 |
| he.06.275-2 Cyno | 1.9E-09 | 6.9E-04 | 3.7E+05 | 1.49 |
| he.06.275-3 Cyno | 1.3E-09 | 5.0E-04 | 3.9E+05 | 1.19 |
| he.06.275-4 Cyno | 1.7E-09 | 6.0E-04 | 3.6E+05 | 1.2 |
| chXHA.06.642 Human | 1.3E-09 | 4.6E-04 | 3.5E+05 | 5.15 |
| he.06.642-1 Human | 2.0E-09 | 3.5E-04 | 1.7E+05 | 12.9 |
| he.06.642-2 Human | 3.1E-09 | 5.3E-04 | 1.7E+05 | 12.6 |
| chXHA.06.642 Cyno | 26E-08 | 4.3E-03 | 1.7E+05 | 12.6 |
| he.06.642-1 Cyno | 3.1E-08 | 3.8E-03 | 1.2E+05 | 8.29 |
| he.06.642-2 Cyno | 4.7E-08 | 8.3E-03 | 1.8E+05 | 11.1 |

TABLE 10

| Sample | ka | kd | KD | Res SD |
|---|---|---|---|---|
| he.06.642 3 -G1 lot1 | 1.038(1)e5 | 3.828(5)e-4 | 3.688(5) nM | 0.977 |
| he.06.642 3 -G1 lot2 | 1.02E+5 | 3.88E-4 | 3.79977 nM | 1.06 |
| he.06.642 3 -G2 | 9.801(1)e4 | 4.210(7)e-4 | 4.296(6) nM | 1.054 |
| chXHA.06.642 | 1.962(3)e5 | 6.47E-04 | 3.296(5) nM | 1.389 |
| CHO.KLHG2-60 | No binding | No binding | No binding | No binding |

In order to compare rat and mouse cross reactivity using covalently immobilized antibodies, a CM4 chip was coupled with he.06.642-2 and he.06.275-4 antibodies via standard EDC-NHS amine coupling chemistries according to the recommended protocol from BIACORE® Inc. The PRLR ECD injections were performed at five concentrations in a three fold titration series starting at 111 nM and going down to 1.37 nM. Regeneration was performed with Glycine pH3.0. The affinity of all of the HE variants of XHA.06.642 and XHA.06.275 are very similar to the affinity of the parental chimeric antibody. Antibody he.06.642-2 binds to human, mouse and rat PRLR with equivalent affinity. It binds to Cyno PRLR with 15 fold weaker affinity than human PRLR. Antibody he.06.275-4 binds to Cyno PRLR with 5 fold weaker affinity than Human PRLR. Antibody he.06.275-4 does not bind effectively to Mouse or Rat PRLR. A summary of the data is provided in Table 11.

TABLE 11

Cross Species Affinity Analysis of Select HE Variants on Covalently Immobilized Antibodies he.06.642-2 Results

| Sample | kon | koff | KD (nM) |
|---|---|---|---|
| he.06.642-2 Human | 3.5E+05 | 9.1E-04 | 2.6 |
| he.06.642-2 Cyno | 1.5E+05 | 6.0E-03 | 38.9 |
| he.06.642-2 Murin | 1.1E+05 | 3.1E-04 | 2.7 |
| he.06.642-2 Rat | 7.6E+04 | 1.4E-04 | 1.9 |

Cyno KD/Human KD = 15
Murine KD/Human KD = 1
Rat KD/Human KD = 0.75 he.06.275-4 Results

| Sample | kon | koff | KD (nM) |
|---|---|---|---|
| he.06.275-4 Human | 3.4E+05 | 4.5E-04 | 1.3 |
| he.06.275-4 Cyno | 1.3E+05 | 8.2E-04 | 6.4 |
| he.06.275-4 Murin | 2.1E+03 | 3.7E-02 | 17,613 |
| he.06.275-4 Rat | 0.0E+00 | 0.0E-00 | 0 |

Cyno KD/Human KD = 5
Murine KD/Human KD = 13,548
Rat KD/Human KD =

Example 14

Figure 11:
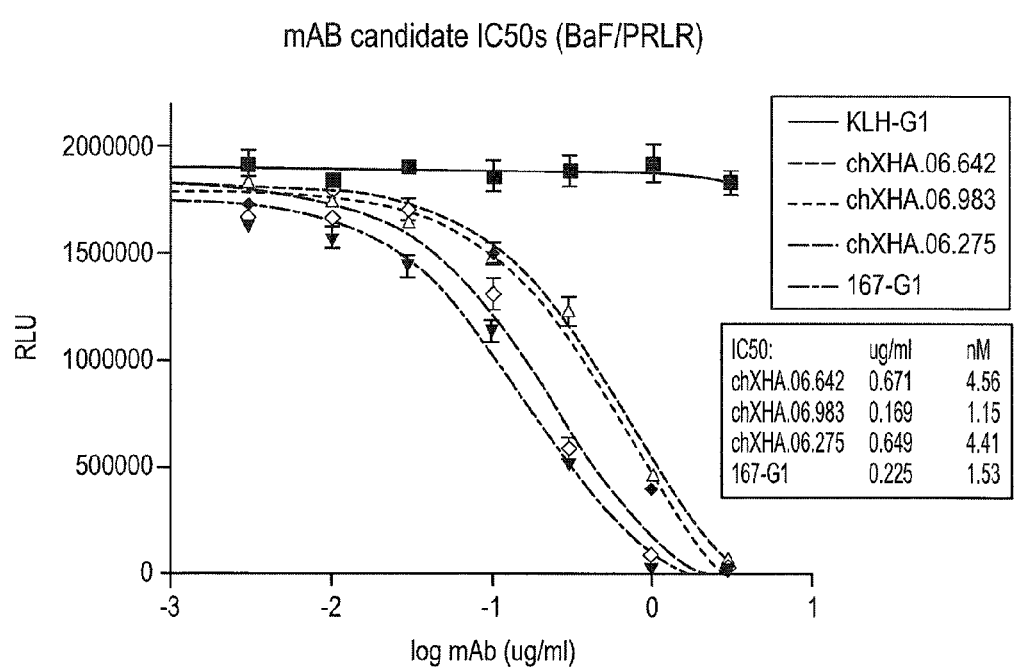
FIG. 11 shows chimeric anti-PRLR mAbs chXHA.06.642, chXHA.06.275, and chXHA.06.983 potently inhibit the proliferation and survival of BaF/PRLR cells. KLH-G1 is a non-specific isotype matched control antibody. Panel at right shows 1050 values of corresponding mouse mAbs.
Figure 12:
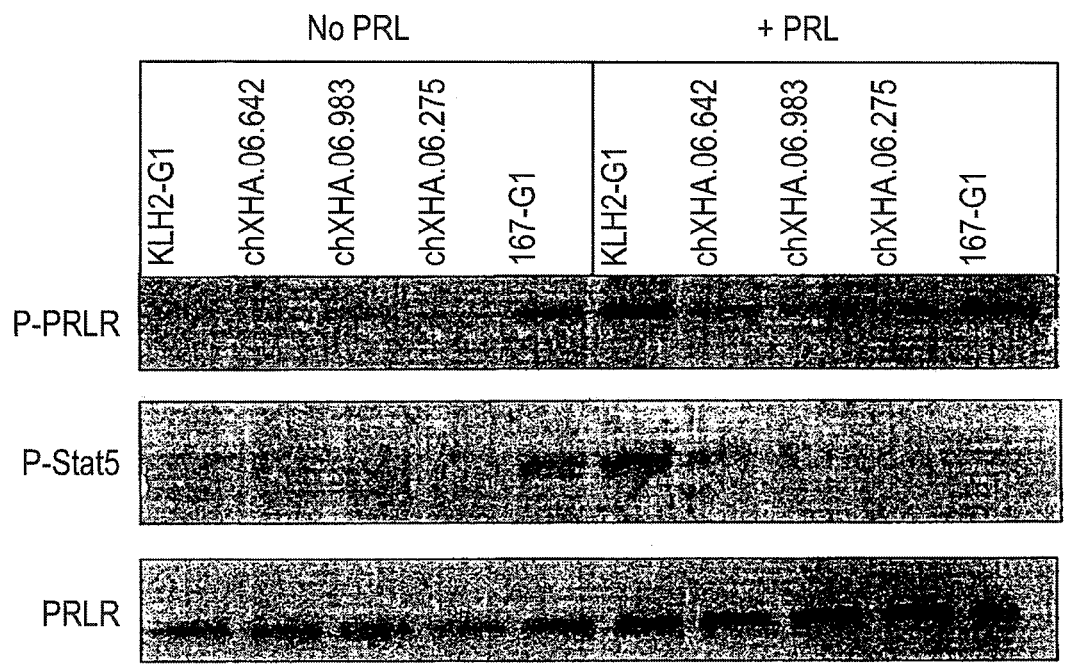
FIG. 12 shows chimeric anti-PRLR mAbs inhibit STAT5 signaling in T47D cells. Cells were pre-treated with 1 ug/ml mAb prior to 30 min stimulation with 50 ng/ml PRL. Lysates were analyzed for the presence of phospho-PRLR using antibodies specific for phosphotyrosine residues 546 and 611 of the PRLR.

Inhibition of BaF/PRLR Cell Proliferation and Survival and Inhibition of PRLR-Induced ERK1/2 Phosphorylation Chimeric mAbs were analyzed for their ability to inhibit the proliferation and survival of BaF/PRLR cells [FIG. 11]. All chimeras tested were found to have retained their potencies relative to their corresponding hybridoma clones. In fact, XHA.06.642 and XHA.06.275 were found to have gained potency in this assay following chimerization. In order to assess the PRLR signal-neutralizing capability of the chimeric antibodies in a human breast cancer model, T47D cells were treated with 1 ug/ml mAb for 30 min prior to PRL stimulation. At the same time, additional cell samples were incubated with antibody alone to examine any potential agonism gained through chimerization of the antibody candidates. As can be seen in FIG. 12, all chimeric antibodies retained their ability to block PRL-induced signaling in T47D while only chXHA.06.983 showed detectable induction of PRLR signaling (a small but reproducible effect) represented by phospho-PRLR and phospho-Stat5.

Determination of Antibody Effect on ERK1/2 Phosphorylation

Selected HUMAN ENGINEERED™ antibodies were tested for their ability to inhibit PRLR-induced ERK1/2 phosphorylation, as described below and in Example 5 above.

Figure 13:
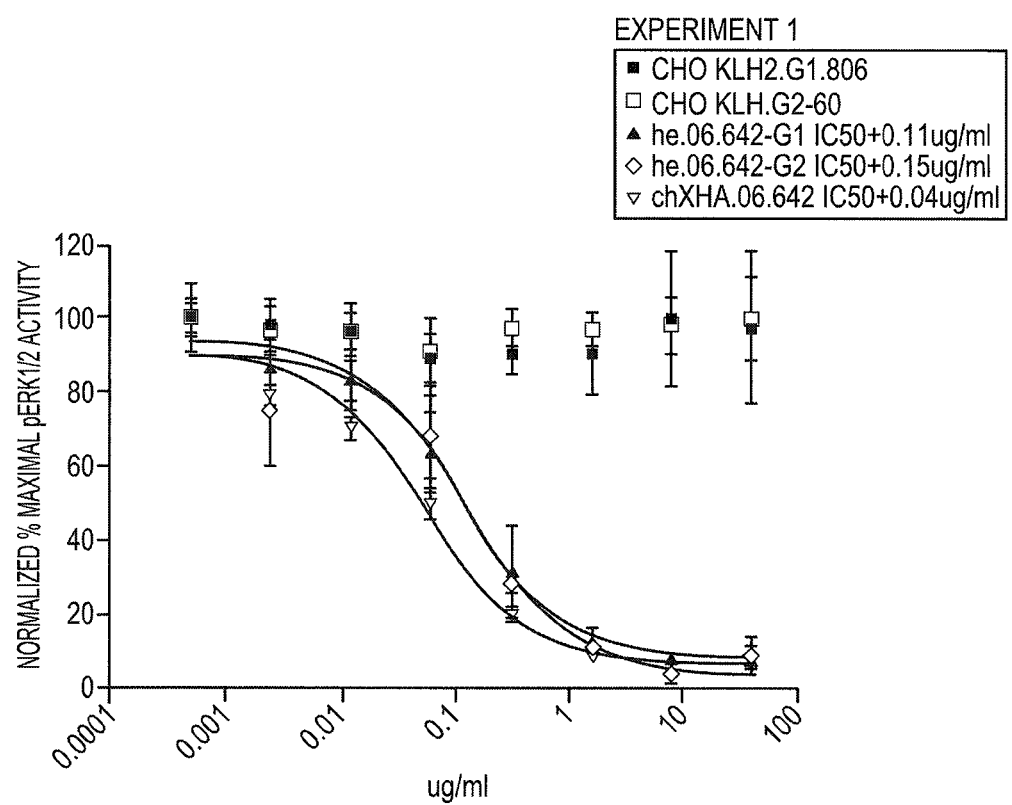
FIG. 13 shows the effect of HUMAN ENGINEERED™ antibodies on pERK1/2 phosphorylation.

Following a 5 hour serum starvation, T47D cells were seeded in microtiter plates in complete growth medium for 24 hours at 37° C. Cells were washed twice with phosphate buffered saline (PBS) and incubated with antibodies diluted in serum-free media containing 0.1% BSA for 30 minutes at 37° C. The final starting concentration of the antibodies was 40 ug/ml. Media was removed and prolactin diluted in serum-free media containing 0.1% BSA was added to a final concentration of 30 ng/ml. Cells were incubated with prolactin for 30 minutes at 37° C. followed by two washes with ice cold PBS. Standard lysis buffer containing detergents, chelators, and various protease and phosphatase inhibitors was added to generate cell lysates. The levels of phosphorylated ERK1/2 (pERK1/2) were measured using standard ELISA according to instructions of DUOSET® IC Phospho-ERK1/ERK2, R&D Systems, Inc. Results of a representative assay are displayed in FIG. 13.

Example 15

Figure 14:
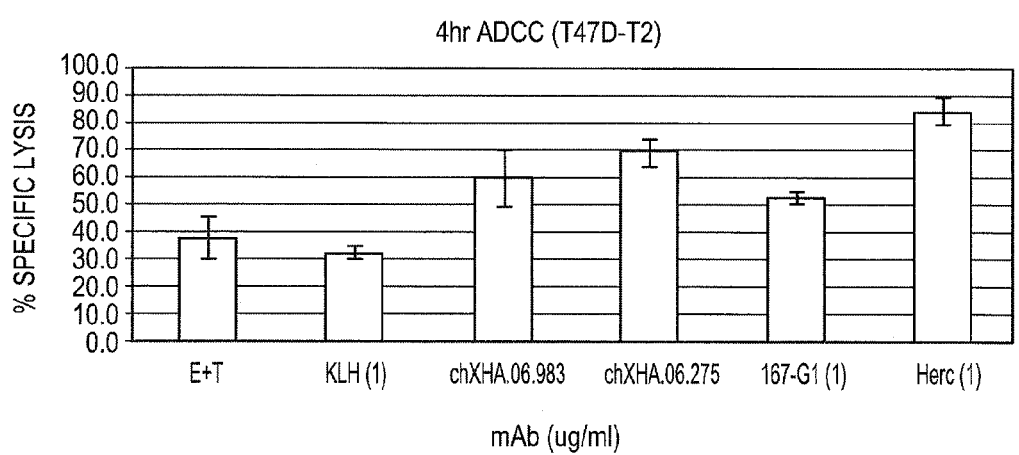
FIG. 14 shows ADCC mediated by chimeric anti-PRLR mAbs. T47D-T2 cells were labeled with Calcein-AM prior to application of mAb (1 ug/ml) and purified human NK cells at an effector-to-target ratio of 10:1. Following a 4 hr incubation, Calcein-AM release into the supernatant was measured. Anti-KLH antibody and Herceptin were used as negative and positive controls, respectively. % specific lysis was calculated as (experimental release−spontaneous release)/(maximal release−spontaneous release)×100.

A. Ability of mAb Candidates to Mediate ADCC Against PRLR-Expressing Target Cells One of the intended mechanisms of action of anti-PRLR mAb is the ability to mediate antibody dependent cellular cytotoxicity (ADCC). In order to assess the capacity for ADCC of candidate antibodies, the T47D cells were employed as PRLR-expressing breast epithelial targets. As shown in FIG. 14, two of the chimeric anti-PRLR mAbs are capable of inducing ADCC mediated by purified human NK cells. chXHA.06.275 was demonstrated to induce approximately 30% specific lysis of target cells within 4 hr. Due to prolonged generation time of chXHA.06.642, this candidate was not included in the original ADCC assays.

B. Anti-PRLR Antibody Effect on Cytokine Levels

Potential cytokine regulation by PRL in breast cancer cells was investigated. In this experiment, MCF7 or T47D cells were exposed to PRL with or without chXHA.06.642 for a period of 48 hrs. A multiplex sandwich immunoassay from MesoScale Diagnostics was employed in order to measure chXHA.06.642 effects on potential PRL-regulated cytokines. It was found that PRL induces VEGF secretion from T47D cells, and that this effect was completely abrogated with the addition of antibody chXHA.06.642. No significant regulation of IL-1β, IL-6, IL-8, IL-10, IL-12 p70, IFN-γ, or TNF-α by PRL or anti-PRLR mAb was detected in these experiments. These results suggest that the PRL/PRLR pathway may contribute to angiogenesis as well as cell growth and survival in breast tumors and that inhibiting this VEGF-regulatory pathway may be another potential in vivo mechanism of action for an anti-PRLR therapeutic antibody.

C. In Vitro Combination Studies Utilizing Anti-PRLR mAbs and Chemotherapeutics Due to the possibility that a potential anti-PRLR therapeutic antibody may be administered in conjunction with cytotoxic drug regimens in the clinic, the effects of such combination therapies on cell survival in culture was investigated. To this end, BaF3/PRLR cells were treated with chXHA.06.642 or chXHA.06.275 at various concentrations in parallel with chemotherapeutics for 5 days, after which cell survival was assessed using CellTiter Glo as a marker of cell number. An array of clinically-relevant and mechanistically diverse cytotoxic agents were utilized in this assay: Doxorubicin (an anthracycline Topo II inhibitor), Taxol (a microtubule stabilizing agent), Fludarabine (an anti-metabolite), and Cisplatin (a platinum-based DNA cross-linking drug). It was found that chXHA.06.275 and, to a greater degree, chXHA.06.642, synergizes with Doxorubicin to enhance cell death in BaF/PRLR cells [See FIG. 15]. The resulting differences in chemotherapeutic IC50 values with and without anti-PRLR mAb chXHA.06.642 and chXHA.06.275 are summarized in Table 12.

TABLE 12

| Cytotoxic Drug | KLH (1 ug/ml) | chXHA.06.642 (1 ug/ml) | chXHA.06.275 (1 ug/ml) |
|---|---|---|---|
| Doxorubicin | 6.44 nM | 2.14 nM | 2.56 nM |
| Taxol | 4.14 nM | 2.07 nM | 2.45 nM |
| Fludarabine | 104.6 uM | 40.0 uM | 93.8 uM |
| Cisplatin | 165.5 nM | 27.6 nM | 46.8 nM |

D. Anti-PRLR Functional Activity of Anti-PRLR mAb

Figure 16:
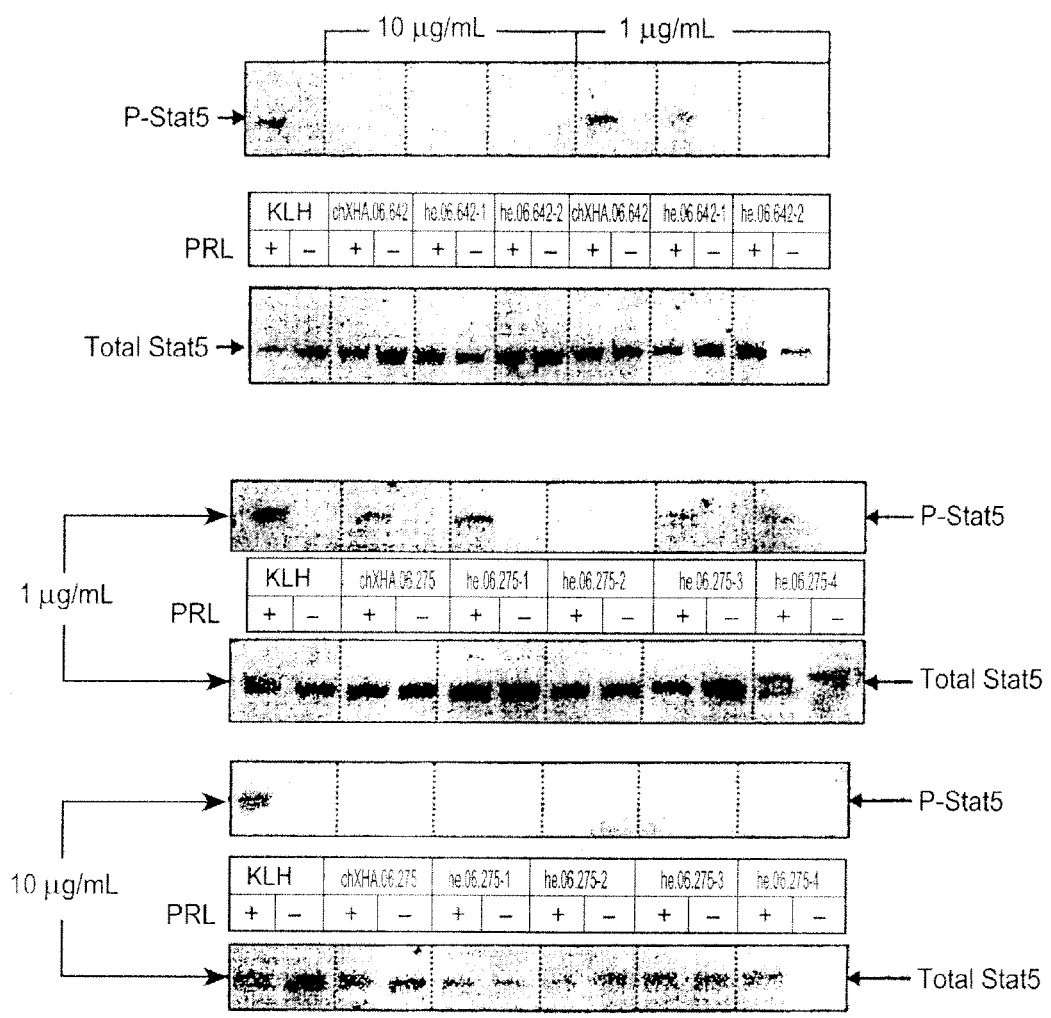
FIG. 16 shows HUMAN ENGINEERED™ mAb retain anti-PRLR functional characteristics in STAT5 phosphorylation assays. T47D cells were incubated with 1 or 10 ug/ml mAb, then treated with or without PRL (50 ng/ml) for an additional 30 min.

Antibodies were assessed in target modulation and cell proliferation assays. FIG. 16 depicts the effect of 2 concentrations of chXHA.06.642 and HUMAN ENGINEERED™ antibodies he.06.642-1 and he.06.642-2, on PRL-induced Stat5 phosphorylation in T47D cells. Both retained potent antagonistic properties as evidenced by complete p-Stat5 signal abrogation. Additionally, neither antibody displayed any agonistic activity or cells treated with mAb alone. Similar results were found for chXHA.06.275 variants. Thus, the HUMAN ENGINEERING™ did not impact the overall antagonistic or agonistic qualities of these antibodies.

Figure 17:
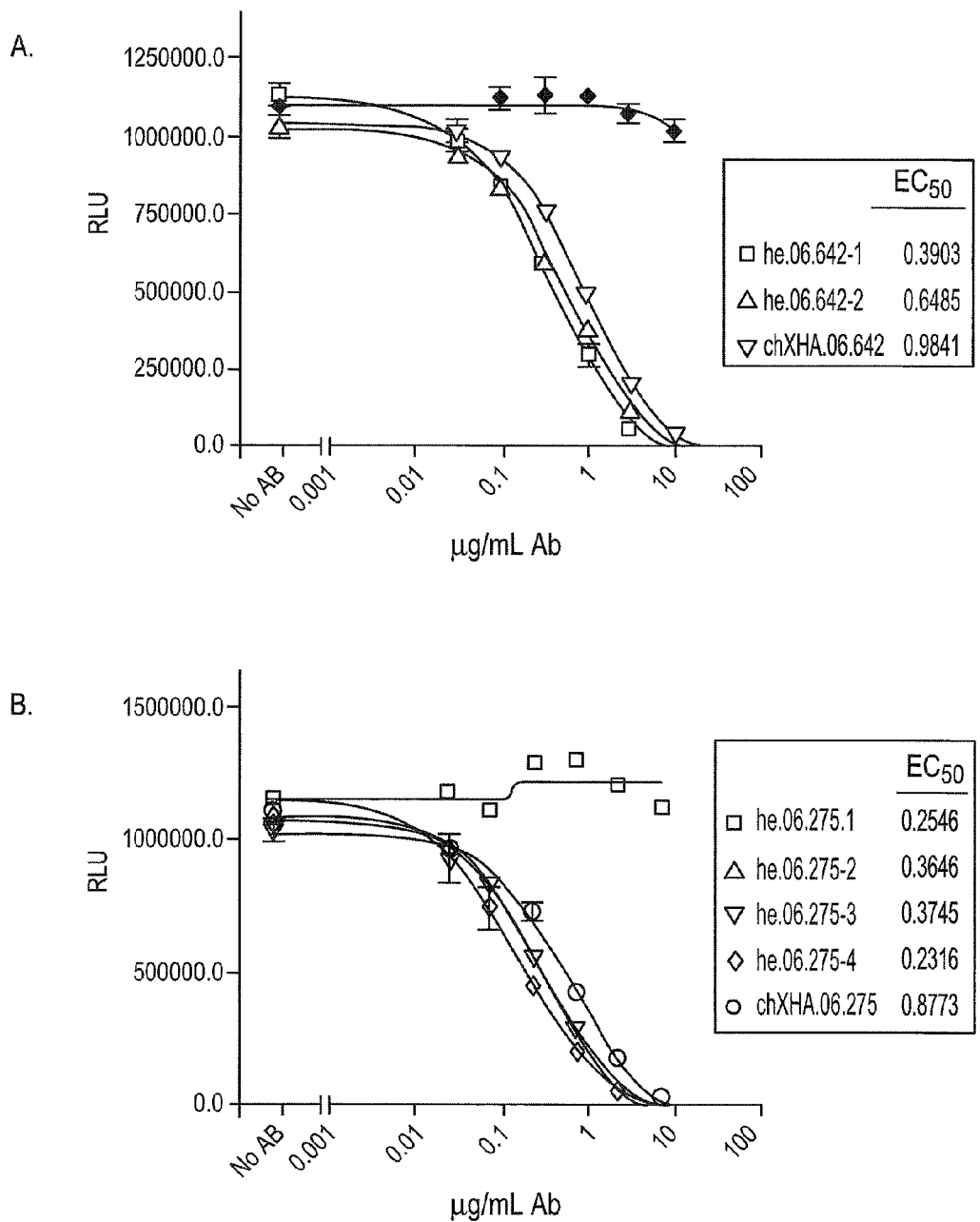
FIGS. 17A and B show humanized anti-PRLR antibody candidates potently inhibit the growth of PRL-dependent BaF3/PRLR cells. BaF3/PRLR cells were grown in the presence of PRL (50 ng/ml) for 48 hr with either anti-KLH control antibody (top line), chimeric antibody, or HUMAN ENGINEERED™ versions. EC50 values were calculated using non-linear regression analysis of the curve fits.

The BaF/PRLR cell proliferation assay was utilized in order to determine relative IC50 values of anti-PRLR chimeric and HUMAN ENGINEERED™ antibodies [See FIG. 17]. As a result of these experiments, all HUMAN ENGINEERED™ antibodies had approximately equivalent potencies to murine counterparts.

Example 16

Evaluation of Anti-Tumor Activity of Anti-PRLR Antibody in a Nb2-C11 Rat Lymphoma Model A single-dose PD study was conducted with chXHA.06.642 in the Nb2-C11 tumor xenograft model to determine whether the anti-PRLR mAb could reach the tumor and block signaling. Antibody chXHA.06.642 was used in this study based on its affinity to rat PRLR (described above). The PD marker monitored was p-STAT5, a downstream mediator of PRLR signaling which can be detected using immunoblot or IHC methods. Since baseline p-STAT5 levels in Nb2-C11 tumor xenografts were too low to adequately detect, mice received exogenous ovine (o)PRL stimulation to increase baseline p-STAT5 levels, and thus provide a more suitable dynamic range.

Induction of p-STAT5 was detected by Western and IHC analyses in Nb2-Cc11 tumor bearing animals injected with ovine PRL as compared with the control injected with saline [See FIGS. 18A and B]. Inhibition of p-STAT5 was observed in mice treated with 10 mg/kg chXHA.06.642 48 hours prior to oPRL injection and not in the KLH IgG1 treated control animals.

Figure 19:
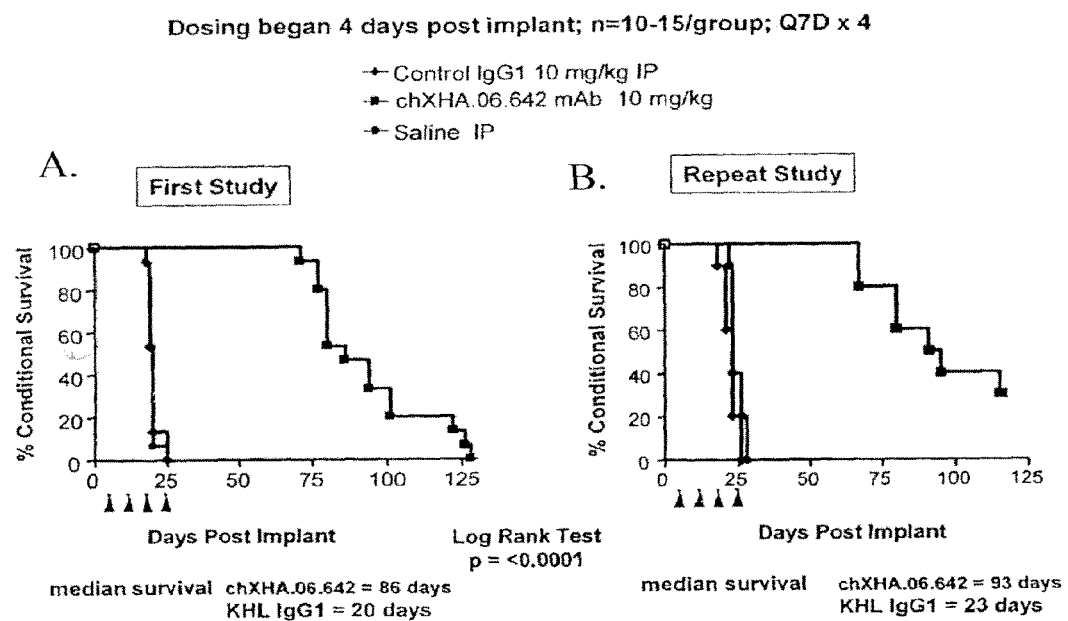
FIGS. 19A and B show that chXHA.06.642 is efficacious in the Nb2-c11 rat lymphoma model in SCID mice in two different studies.

To determine whether inhibition of PRLR signaling correlates with Nb2-C11 tumor growth inhibition, a multi-dose efficacy study was performed with once weekly administration of chXHA.06.642 [See FIGS. 19A and B]. Dosing was initiated 4 days post cell implantation (before tumors were palpable) with chXHA.06.642 or KLH IgG1 at 10 mg/kg, or a saline control. Four weekly intraperitoneal doses of mAb were given. The model employed a conditional survival or time to progression endpoint, as these tumors invade the muscle and are thus difficult to measure accurately with calipers. Tumors in the chXHA.06.642 treated group were not detected until about 11 weeks post implantation (7.5 weeks after the $4^{th}$ mAb dose), when two of the 15 animals in this group succumbed to tumor burden. The median survival in the saline and KLH IgG1 control treated groups was 20 days post cell implantation (p<0.0001), at which point animals were euthanized due to tumor burden. Animals in the chXHA.06.642 treated group gained body weight while the control animals maintained or lost body weight, presumably due to disease burden.

Figure 20:
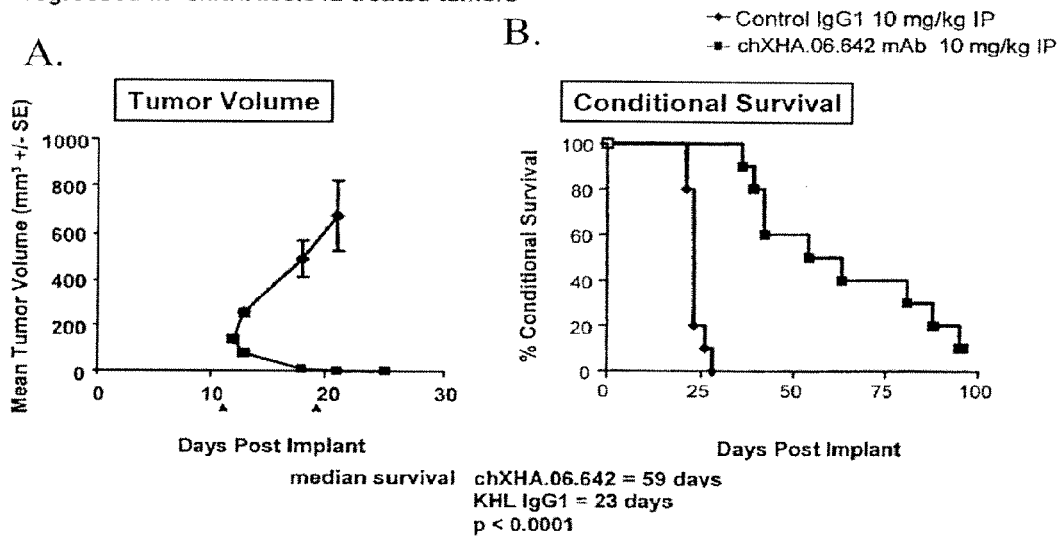
FIGS. 20A and B show chXHA.06.642 regresses established Nb2-C11 rat lymphoma tumors in SCID mice.
FIG. 20B displays conditional survival.

A second efficacy arm was included in this study, in which animals with established tumors were enrolled in the study 12 days post cell implantation [See FIG. 20A and B]. Mean tumor volumes were 135 mm³ at the time of dosing initiation. Animals were dosed intraperitoneally with 10 mg/kg once weekly with either chXHA.06.642 or KLH IgG1 control antibodies for 2 doses. Tumors appeared to fully regress by two days after the $2^{nd}$ dose (3 weeks post-implantation). However, approximately two weeks later tumors started to reappear in the mice. In comparison, the KLH IgG1 control animals had a heavy tumor burden, which had a mean volume of >600 mm³. Since these tumors grow directly into the muscle, mean tumor volume may be larger than that recorded by caliper measurements. The median survival in both the saline and KLH IgG1 groups was 23 days post-cell implantation (p=0<0.0001). As in the initial study, the animals in the chXHA.06.642 treated group gained body weight while the control animals maintained or lost body weight. Thus, the chXHA.06.642 mAb was effective against not only a low number of tumor cells (treatment initiation 4 days after implant), but was also able to completely regress the aggressive established Nb2-C11 tumors for more than 2 weeks.

The Nb2-C11 model has demonstrated that an anti-PRLR mAb has the ability to effectively target antigen-expressing tumors in vivo, inhibit PLR-driven signaling within the tumor, and induce a measurable outcome in tumor burden, even when the animal has an aggressive established tumor.

Example 17

Human Breast Carcinoma T47D Model for PD Assessment

A single dose PD study was performed in vivo with antibody chXHA.06.642 tested in Example 16 using breast carcinoma T47D cells. The ability of oPRL to stimulate PRLR signaling as well as the ability of chXHA.06.642 to inhibit this signaling in vivo was evaluated. Tumor-implanted animals received an intraperitoneal injection of saline, KLH IgG1 control mAb or chXHA.06.642, and 48 hours later received either saline or 20 ug oPRL by bolus injection. Forty minutes later tumor tissues were collected. A significant induction of p-STAT5 was observed in tumors from the oPRL bolus treated animals, but not in the saline control animals, as assessed by Western blotting, although it is slightly more variable by IHC analysis (FIG. 21). Levels of p-AKT and p-ERK were not increased by oPRL stimulation in vivo. Significantly, treatment with chXHA.06.642, but not the KLH IgG1 control, demonstrated strong inhibition of p-STAT5 induction after oPRL bolus injection. IHC analysis generally confirms this result. Significantly, p-STAT5 was inhibited in tumors in 4 out of 4 chXHA.06.642 treated animals by both Western blotting and IHC analyses.

Example 18

PRLR Expression and Correlation of PRLR Expression with ER and Her2-Neu Expression In normal tissues, PRLR expression, as quantified by RT-PCR, is highest in breast and uterus followed by kidney, liver, prostate, and ovary. Levels of PRLR mRNA are lowest in the trachea, brain, and lung (Pierce S K, et al., J Endocr; 171 (1):R1-R4 (2001)).

Immunohistochemical (IHC) analyses may be carried out as follows. Frozen tissue samples from cancer patients are embedded in an optimum cutting temperature (OCT) compound and quick-frozen in isopentane with dry ice. Cryosections are cut with a Leica 3050 CM mictrotome at thickness of 5 µm and thaw-mounted on vectabound-coated slides. The sections are fixed with ethanol at −20° C. and allowed to air dry overnight at room temperature. The fixed sections are stored at −80° C. until use. The tissue sections are retrieved and first incubated in blocking buffer (PBS, 5% normal goat serum, 0.1% Tween 20) for 30 minutes at room temperature, and then incubated with the cancer-associated protein-specific monoclonal antibody and control monoclonal antibodies diluted in blocking buffer (1 µg/ml) for 120 minutes. The sections are then washed three times with the blocking buffer. The bound monoclonal antibodies are detected with a goat anti-mouse IgG+IgM (H+L) F(ab')2-peroxidase conjugates and the peroxidase substrate diaminobenzidine (1 mg/ml, Sigma Catalog No. D 5637) in 0.1 M sodium acetate buffer pH 5.05 and 0.003% hydrogen peroxide (Sigma cat. No. H1009). The stained slides are counter-stained with hematoxylin and examined under Nikon microscope.

Monoclonal antibody against a cancer associated protein (antigen) is used to test reactivity with various cell lines from different types of tissues. Cells from different established cell lines are removed from the growth surface without using proteases, packed and embedded in OCT compound. The cells are frozen and sectioned, then stained using a standard IHC protocol. The CELLARRAY™ technology is described in WO 01/43869. Normal tissue (human) obtained by surgical resection are frozen and mounted. Cryosections are cut with a Leica 3050 CM mictrotome at thickness of 5 µm and thaw-mounted on vectabound-coated slides. The sections are fixed with ethanol at −20° C. and allowed to air dry overnight at room temperature. POLYMICA™ Detection kit is used to determine binding of a cancer-associated antigen-specific monoclonal antibody to normal tissue. Primary monoclonal antibody is used at a final concentration of 1 µg/ml.

In order to investigate the incidence of PRLR expression and its correlation with ER and Her2-neu expression, 122 invasive breast cancer patient samples were evaluated using immunohistochemistry (IHC). Overall, 62/122 (50%) of the samples expressed PRLR, 58/122 (47%) expressed ER, and 32/122 (26%) expressed Her2-neu. Ninety-six (78%) of the samples consisted of invasive ductal carcinoma, of which 48 (50%) expressed PRLR. Among these samples, 24/48 (50%) also expressed ER+ and 13/48 (26%) also Her2-neu.

All of the above U.S. patents, U.S. patent application publications, U.S. patent applications, foreign patents, foreign patent applications and non patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

What is claimed is:

1. An isolated antibody that binds the extracellular domain of PRLR of SEQ ID NO:2 and comprises (a) the Complementarily Determining Regions (CDRs) set forth at positions 23 through 34, positions 50 through 56, and positions 89 through 97 of the amino acid sequence of SEQ ID NO: 91 or SEQ ID NO: 92 and (b) the CDRs set forth at positions 31 through 36, positions 51 through 66, and 99 through 106 of SEQ ID NO: 93 or SEQ ID NO: 94.

2. The antibody of claim 1 wherein the antibody is a chimeric antibody, a humanized antibody, a human engineered antibody, a human antibody, a single chain antibody or an antibody fragment.

3. The antibody of claim 1 that comprises a constant region of a human antibody sequence and one or more heavy and light chain variable framework regions of a human antibody sequence.

4. The antibody of claim 3 wherein the human antibody sequence is an individual human sequence, a human consensus sequence, an individual human germline sequence, or a human consensus germline sequence.

5. The antibody of claim 1 wherein the heavy chain constant region is a modified or unmodified IgG, IgM, IgA, IgD, IgE, a fragment thereof, or combinations thereof.

6. The antibody of claim 5 wherein the heavy chain constant region is a modified or unmodified IgG1, IgG2, IgG3 or IgG4.

7. The antibody of claim 1 that has an equilibrium dissociation constant ($K_D$) of $10^{-6}$, $10^{-7}$, $10^{-8}$ or $10^{-9}$ M or lower to PRLR.

8. The antibody of claim 1 wherein the light chain constant region is a modified or unmodified lambda light chain constant region, a kappa light chain constant region, a fragment thereof, or combinations thereof.

9. The antibody of claim 1 that inhibits PRLR intracellular phosphorylation.

10. The antibody of claim 1 that inhibits the induction of Stat5 phosphorylation.

11. The antibody of claim 1 that inhibits the proliferation of a breast cancer cell.

12. The antibody of claim 1 that is conjugated to another diagnostic or therapeutic agent.

13. The antibody of claim 1 that is purified to at least 95% homogeneity by weight.

14. The antibody according to claim 1 that binds the extracellular domain of human PRLR with an equilibrium dissociation constant ($K_D$) of at least 10,000 to 15,000 fold lower than the extracellular domain of murine PRLR.

15. The antibody according to claim 1 that binds the extracellular domain of human PRLR, the extracellular domain of murine PRLR, and the extracellular domain of rat PRLR.

16. The antibody according to claim 15 that binds the extracellular domain of murine and rat PRLR with an equilibrium dissociation constant ($K_D$) of $10^{-6}$ M or lower.

17. The antibody of claim 16 that binds the same epitope as the heavy chain and light chain variable regions of the he.06.275-4 antibody.

18. A pharmaceutical composition comprising the antibody of claim 13 and a pharmaceutically acceptable carrier.

19. A kit comprising a therapeutically effective amount of an antibody of claim 1, packaged in a container, said kit containing a second therapeutic agent, and further comprising a label attached to or packaged with the container, the label describing the contents of the container and providing indications and/or instructions regarding use of the contents of the container to treat breast cancer.

20. The kit of claim 19 wherein the container is a vial or bottle or prefilled syringe.

21. An isolated antibody that binds the extracellular domain of PRLR comprising a variable light chain amino acid sequence SEQ ID NO: 91, and a variable heavy chain amino acid sequence of SEQ ID NO: 93.

22. An isolated antibody that binds the extracellular domain of PRLR comprising a variable light chain amino acid sequence SEQ ID NO: 91, and a variable heavy chain amino acid sequence of SEQ ID NO: 94.

23. An isolated antibody that binds the extracellular domain of PRLR comprising a variable light chain amino acid sequence SEQ ID NO: 92, and a variable heavy chain amino acid sequence of SEQ ID NO: 93.

24. An isolated antibody that binds the extracellular domain of PRLR comprising a variable light chain amino acid sequence SEQ ID NO: 92, and a variable heavy chain amino acid sequence of SEQ ID NO: 94.

* * * * *

SEQUENCE LISTING

```
<160> NUMBER OF SEQ ID NOS: 103

<210> SEQ ID NO 1
<211> LENGTH: 1846
<212> TYPE: DNA
<213> ORGANISM: Homo sapiens

<400> SEQUENCE: 1
atgaaggaaa atgtggcatc tgcaaccgtt ttcactctgc tactttttct caacacctgc      60
cttctgaatg acagttacc tcctggaaaa cctgagatct ttaaatgtcg ttctcccaat     120
aaggaaacat tcacctgctg gtggaggcct gggacagatg gaggacttcc taccaattat    180
```

```
tcactgactt accacaggga aggagagaca ctcatgcatg aatgtccaga ctacataacc    240
ggtggcccca actcctgcca ctttggcaag cagtacacct ccatgtggag gacatacatc    300
atgatggtca atgccactaa ccagatggga agcagtttct cggatgaact ttatgtggac    360
gtgacttaca tagttcagcc agaccctcct ttggagctgg ctgtggaagt aaaacagcca    420
gaagacagaa aaccctacct gtggattaaa tggtctccac ctaccctgat tgacttaaaa    480
actggttggt tcacgctcct gtatgaaatt cgattaaaac ccgagaaagc agctgagtgg    540
gagatccatt ttgctgggca gcaaacagag tttaagattc tcagcctaca tccaggacag    600
aaataccttg tccaggttcg ctgcaaacca gaccatggat actggagtgc atggagtcca    660
gcgaccttca ttcagatacc tagtgacttc accatgaatg atacaaccgt gtggatctct    720
gtggctgtcc tttctgctgt catctgtttg attattgtct gggcagtggc tttgaagggc    780
tatagcatgg tgacctgcat ctttccgcca gttcctgggc caaaaataaa aggatttgat    840
gctcatctgt tggagaaggg caagtctgaa gaactactga gtgccttggg atgccaagac    900
tttcctccca cttctgacta tgaggacttg ctggtggagt atttagaagt agatgatagt    960
gaggaccagc atctaatgtc agtccattca aaagaacacc caagtcaagg tatgaaaccc   1020
acatacctgg atcctgacac tgactcaggc cggggggagc tgtgacagcc ttcccttttg   1080
tctgaaaagt gtgaggaacc ccaggccaat ccctccacat tctatgatcc tgaggtcatt   1140
gagaagccag agaatcctga aacaacccac acctgggacc cccagtgcat aagcatggaa   1200
ggcaaaatcc cctatttttca tgctggtgga tccaaatgtt caacatggcc cttaccacag   1260
cccagccagc acaaccccag atcctcttac cacaatatta ctgatgtgtg tgagctggct   1320
gtgggccctg caggtgcacc ggccactctg ttgaatgaag caggtaaaga tgctttaaaa   1380
tcctctcaaa ccattaagtc tagagaagag ggaaaggcaa cccagcagag ggaggtagaa   1440
agcttccatt ctgagactga ccaggatacg ccctggctgc tgccccagga gaaaaccccc   1500
tttggctccg ctaaacccct tggattatgtg gagattcaca aggtcaacaa agatggtgca   1560
ttatcattgc taccaaaaca gagagagaac agcggcaagc caagaagcc cgggactcct   1620
gagaacaata aggagtatgc caaggtgtcc ggggtcatgg ataacaacat cctggtgttg   1680
gtgccagatc acatgctaaa aacgtggct tgctttgaag aatcagccaa agaggcccca   1740
ccatcacttg aacagaatca agctgagaaa gccctggcca acttcactgc aacatcaagc   1800
aagtgcaggc tccagctggg tggtttggat tacctggatc ccgcat               1846
```

<210> SEQ ID NO 2
<211> LENGTH: 622
<212> TYPE: PRT
<213> ORGANISM: Homo sapiens

<400> SEQUENCE: 2

```
Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
        35                  40                  45

Arg Pro Gly Thr Asp Gly Gly Leu Pro Thr Asn Tyr Ser Leu Thr Tyr
    50                  55                  60

His Arg Glu Gly Glu Thr Leu Met His Glu Cys Pro Asp Tyr Ile Thr
65                  70                  75                  80
```

```
Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp
        115                 120                 125

Pro Pro Leu Glu Leu Ala Val Glu Val Lys Gln Pro Glu Asp Arg Lys
    130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
    210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
                245                 250                 255

Ala Leu Lys Gly Tyr Ser Met Val Thr Cys Ile Phe Pro Pro Val Pro
            260                 265                 270

Gly Pro Lys Ile Lys Gly Phe Asp Ala His Leu Leu Glu Lys Gly Lys
        275                 280                 285

Ser Glu Glu Leu Leu Ser Ala Leu Gly Cys Gln Asp Phe Pro Pro Thr
    290                 295                 300

Ser Asp Tyr Glu Asp Leu Leu Val Glu Tyr Leu Glu Val Asp Asp Ser
305                 310                 315                 320

Glu Asp Gln His Leu Met Ser Val His Ser Lys Glu His Pro Ser Gln
                325                 330                 335

Gly Met Lys Pro Thr Tyr Leu Asp Pro Asp Thr Asp Ser Gly Arg Gly
            340                 345                 350

Ser Cys Asp Ser Pro Ser Leu Leu Ser Glu Lys Cys Glu Glu Pro Gln
        355                 360                 365

Ala Asn Pro Ser Thr Phe Tyr Asp Pro Glu Val Ile Glu Lys Pro Glu
    370                 375                 380

Asn Pro Glu Thr Thr His Thr Trp Asp Pro Gln Cys Ile Ser Met Glu
385                 390                 395                 400

Gly Lys Ile Pro Tyr Phe His Ala Gly Gly Ser Lys Cys Ser Thr Trp
                405                 410                 415

Pro Leu Pro Gln Pro Ser Gln His Asn Pro Arg Ser Ser Tyr His Asn
            420                 425                 430

Ile Thr Asp Val Cys Glu Leu Ala Val Gly Pro Ala Gly Ala Pro Ala
        435                 440                 445

Thr Leu Leu Asn Glu Ala Gly Lys Asp Ala Leu Lys Ser Ser Gln Thr
    450                 455                 460

Ile Lys Ser Arg Glu Glu Gly Lys Ala Thr Gln Gln Arg Glu Val Glu
465                 470                 475                 480

Ser Phe His Ser Glu Thr Asp Gln Asp Thr Pro Trp Leu Leu Pro Gln
                485                 490                 495
```

```
Glu Lys Thr Pro Phe Gly Ser Ala Lys Pro Leu Asp Tyr Val Glu Ile
            500                 505                 510

His Lys Val Asn Lys Asp Gly Ala Leu Ser Leu Leu Pro Lys Gln Arg
        515                 520                 525

Glu Asn Ser Gly Lys Pro Lys Lys Pro Gly Thr Pro Glu Asn Asn Lys
    530                 535                 540

Glu Tyr Ala Lys Val Ser Gly Val Met Asp Asn Asn Ile Leu Val Leu
545                 550                 555                 560

Val Pro Asp Pro His Ala Lys Asn Val Ala Cys Phe Glu Glu Ser Ala
                565                 570                 575

Lys Glu Ala Pro Pro Ser Leu Glu Gln Asn Gln Ala Gly Lys Ala Leu
            580                 585                 590

Ala Asn Phe Thr Ala Thr Ser Ser Lys Cys Arg Leu Gln Leu Gly Gly
        595                 600                 605

Leu Asp Tyr Leu Asp Pro Ala Cys Phe Thr His Ser Phe His
    610                 615                 620
```

<210> SEQ ID NO 3
<211> LENGTH: 70
<212> TYPE: DNA
<213> ORGANISM: Homo sapiens

<400> SEQUENCE: 3
gggacaagtt tgtacaaaaa agcaggctac gaaggagata tacatatgaa ggaaaatgtg    60
gcatctgcaa                                                           70

<210> SEQ ID NO 4
<211> LENGTH: 79
<212> TYPE: DNA
<213> ORGANISM: Homo sapiens

<400> SEQUENCE: 4
gggaccactt tgtacaagaa agctgggttt aagctccgtg atggtgatgg tgatgtgctc    60
catcattcat ggtgaagtc                                                 79

<210> SEQ ID NO 5
<211> LENGTH: 48
<212> TYPE: DNA
<213> ORGANISM: Homo sapiens

<400> SEQUENCE: 5
gggacaagtt tgtacaaaaa agcaggcttc gaaggagata gaaccatg                 48

<210> SEQ ID NO 6
<211> LENGTH: 50
<212> TYPE: DNA
<213> ORGANISM: Homo sapiens

<400> SEQUENCE: 6
caggcttcga aggagataga accatgaagg aaaatgtggc atctgcaacc                50

<210> SEQ ID NO 7
<211> LENGTH: 49
<212> TYPE: DNA
<213> ORGANISM: Homo sapiens

<400> SEQUENCE: 7
gaaggaaaat gtggcatctg caaccgtttt cactctgcta cttttctc                 49

```
<210> SEQ ID NO 8
<211> LENGTH: 50
<212> TYPE: DNA
<213> ORGANISM: Homo sapiens

<400> SEQUENCE: 8
cgttttcact ctgctacttt ttctcaacac ctgccttctg aatggaggag      50

<210> SEQ ID NO 9
<211> LENGTH: 50
<212> TYPE: DNA
<213> ORGANISM: Homo sapiens

<400> SEQUENCE: 9
caacacctgc cttctgaatg gaggagcaca tcaccatcac catcacggag      50

<210> SEQ ID NO 10
<211> LENGTH: 50
<212> TYPE: DNA
<213> ORGANISM: Homo sapiens

<400> SEQUENCE: 10
cacatcacca tcaccatcac ggagctcagt tacctcctgg aaaacctgag      50

<210> SEQ ID NO 11
<211> LENGTH: 55
<212> TYPE: DNA
<213> ORGANISM: Homo sapiens

<400> SEQUENCE: 11
gggaccactt tgtacaagaa agctgggttc actgaactat gtaagtcacg tccac      55

<210> SEQ ID NO 12
<211> LENGTH: 48
<212> TYPE: DNA
<213> ORGANISM: Homo sapiens

<400> SEQUENCE: 12
gggacaagtt tgtacaaaaa agcaggcttc gaaggagata gaaccatg      48

<210> SEQ ID NO 13
<211> LENGTH: 50
<212> TYPE: DNA
<213> ORGANISM: Homo sapiens

<400> SEQUENCE: 13
caggcttcga aggagataga accatgaagg aaaatgtggc atctgcaacc      50

<210> SEQ ID NO 14
<211> LENGTH: 49
<212> TYPE: DNA
<213> ORGANISM: Homo sapiens

<400> SEQUENCE: 14
gaaggaaaat gtggcatctg caaccgtttt cactctgcta cttttttctc      49

<210> SEQ ID NO 15
<211> LENGTH: 48
<212> TYPE: DNA
<213> ORGANISM: Homo sapiens

<400> SEQUENCE: 15
cgttttcact ctgctacttt ttctcaacac ctgccttctg aatgttca      48
```

<210> SEQ ID NO 16
<211> LENGTH: 49
<212> TYPE: DNA
<213> ORGANISM: Homo sapiens

<400> SEQUENCE: 16
tctcaacacc tgccttctga atgttcagcc agaccctcct ttggagctg            49

<210> SEQ ID NO 17
<211> LENGTH: 49
<212> TYPE: DNA
<213> ORGANISM: Homo sapiens

<400> SEQUENCE: 17
cgtgatggtg atggtgatgt gctccatcat tcatggtgaa gtcactagg            49

<210> SEQ ID NO 18
<211> LENGTH: 47
<212> TYPE: DNA
<213> ORGANISM: Homo sapiens

<400> SEQUENCE: 18
caagaaagct gggtttaagc tccgtgatgg tgatggtgat gtgctcc              47

<210> SEQ ID NO 19
<211> LENGTH: 37
<212> TYPE: DNA
<213> ORGANISM: Homo sapiens

<400> SEQUENCE: 19
gggaccactt tgtacaagaa agctgggttt aagctcc                         37

<210> SEQ ID NO 20
<211> LENGTH: 115
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Val Val Val Ala Pro Gly Tyr Trp Gly Gln Gly Thr Leu
            100                 105                 110

Val Thr Val
        115

<210> SEQ ID NO 21
<211> LENGTH: 110
<212> TYPE: PRT
<213> ORGANISM: Homo sapiens

<400> SEQUENCE: 21

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Asp Asn Asn Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Pro Val Phe Gly Gly Gly Thr Lys Leu Thr Val Leu
            100                 105                 110

<210> SEQ ID NO 22
<211> LENGTH: 114
<212> TYPE: PRT
<213> ORGANISM: Homo sapiens

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ala Ile Ile Ser Tyr Asp Gly Ser Tyr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ser Ser Thr Ser Asp Tyr Trp Gly Gln Gly Thr Leu Val
            100                 105                 110

Thr Val

<210> SEQ ID NO 23
<211> LENGTH: 110
<212> TYPE: PRT
<213> ORGANISM: Homo sapiens
<220> FEATURE:
<221> NAME/KEY: misc_feature
<222> LOCATION: (84)..(84)
<223> OTHER INFORMATION: Xaa can be any one naturally occurring amino
      acid

<400> SEQUENCE: 23

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Asp Asn Tyr Arg Arg Pro Pro Gly Ile Pro Asp Arg Phe Ser
50                  55                  60

Gly Ser Lys Ser Gly Thr Ala Ser Leu Ala Ile Ser Gly Leu Arg
65                  70                  75                  80

Ser Glu Asp Xaa Ala Asp Tyr Tyr Cys Ala Val Trp Asp Gly Arg Leu
                85                  90                  95

Asn Gly Pro Val Phe Gly Gly Gly Thr Lys Leu Thr Val Leu
            100                 105                 110

<210> SEQ ID NO 24
<211> LENGTH: 113
<212> TYPE: PRT
<213> ORGANISM: Homo sapiens

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Ser Trp Asn Ser Gly Val Val Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Thr Tyr Val Pro Tyr Ser Arg Trp Gly Gln Gly Thr Leu Val Thr
            100                 105                 110

Val

<210> SEQ ID NO 25
<211> LENGTH: 110
<212> TYPE: PRT
<213> ORGANISM: Homo sapiens

<400> SEQUENCE: 25

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Pro Leu Phe Gly Gly Gly Thr Lys Leu Thr Val Leu
            100                 105                 110

<210> SEQ ID NO 26
<211> LENGTH: 114
<212> TYPE: PRT
<213> ORGANISM: Homo sapiens

<400> SEQUENCE: 26

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Asn Ser Tyr
            20                  25                  30

Pro Val His Trp Val Arg Gln Ala Pro Gly Lys Gly Leu Glu Trp Val
        35                  40                  45

Ala Val Ile Ser Tyr Asp Gly Asn Thr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Pro Pro Phe Asp Tyr Trp Gly Gln Gly Thr Leu Ala
            100                 105                 110

Thr Val

<210> SEQ ID NO 27
<211> LENGTH: 112
<212> TYPE: PRT
<213> ORGANISM: Homo sapiens

<400> SEQUENCE: 27

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Glu Ala Trp Asp Asp Thr Leu
                85                  90                  95

Asn Gly Pro His Val Val Phe Gly Gly Gly Thr Lys Leu Thr Val Leu
            100                 105                 110

<210> SEQ ID NO 28
<211> LENGTH: 116
<212> TYPE: PRT
<213> ORGANISM: Homo sapiens

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Gly Met His Trp Val Arg Gln Ala Pro Gly Lys Gly Leu Glu Trp Val
        35                  40                  45

Ala Ala Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asp Ser Ser Gly Thr Val Asp Tyr Trp Gly Gln Gly Thr
            100                 105                 110
```

```
Leu Val Thr Val
        115

<210> SEQ ID NO 29
<211> LENGTH: 110
<212> TYPE: PRT
<213> ORGANISM: Homo sapiens

<400> SEQUENCE: 29

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Asp Asn Tyr Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Lys Asp Glu Ala Asp Tyr Tyr Cys Ala Ala Trp Asp Asp Ser Leu
                85                  90                  95

Asn Gly Leu Val Phe Gly Gly Gly Thr Lys Leu Thr Val Leu
            100                 105                 110

<210> SEQ ID NO 30
<211> LENGTH: 119
<212> TYPE: PRT
<213> ORGANISM: Homo sapiens

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Ile Gly Gly Arg Gly Val Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Asn Trp Thr His Ala Leu Gly Phe Asp Pro Trp Gly
            100                 105                 110

Gln Gly Thr Leu Val Thr Val
        115

<210> SEQ ID NO 31
<211> LENGTH: 110
<212> TYPE: PRT
<213> ORGANISM: Homo sapiens

<400> SEQUENCE: 31

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30
```

```
Thr Val Asn Trp Tyr Gln Gln Leu Pro Gly Thr Ala Pro Lys Leu Leu
         35                  40                  45

Ile Tyr Gly Asn Ser Asn Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Gly Trp Asp Gly Arg Leu
             85                  90                  95

Ile Gly Trp Val Phe Gly Gly Gly Thr Lys Leu Thr Val Leu
            100                 105                 110

<210> SEQ ID NO 32
<211> LENGTH: 116
<212> TYPE: PRT
<213> ORGANISM: Homo sapiens

<400> SEQUENCE: 32

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
         35                  40                  45

Ser Leu Ile Ser Trp Asp Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Thr Gly Ile Ala Val Ala Gly Phe Asp Tyr Trp Gly Gln Gly Thr
            100                 105                 110

Leu Val Thr Val
        115

<210> SEQ ID NO 33
<211> LENGTH: 110
<212> TYPE: PRT
<213> ORGANISM: Homo sapiens

<400> SEQUENCE: 33

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
            20                  25                  30

Ala Val Asn Trp Tyr Gln Gln Leu Pro Gly Thr Ala Pro Lys Leu Leu
         35                  40                  45

Ile Tyr Asp Ser Asn Lys Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asn Ser Leu
             85                  90                  95

Asn Gly Trp Val Phe Gly Gly Gly Thr Lys Leu Thr Val Leu
            100                 105                 110

<210> SEQ ID NO 34
<211> LENGTH: 114
```

```
<212> TYPE: PRT
<213> ORGANISM: Homo sapiens

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Leu Ile Ser Trp Asp Gly Tyr Arg Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Thr Thr Gly Ala Ser Tyr His Ala Leu Trp Gly Gln Gly Thr Leu Val
            100                 105                 110

Thr Val

<210> SEQ ID NO 35
<211> LENGTH: 110
<212> TYPE: PRT
<213> ORGANISM: Homo sapiens

<400> SEQUENCE: 35

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asp Ile Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Asn Gly Pro Val Phe Gly Gly Gly Thr Lys Leu Thr Val Leu
            100                 105                 110

<210> SEQ ID NO 36
<211> LENGTH: 112
<212> TYPE: PRT
<213> ORGANISM: Homo sapiens

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Leu Ile Ser Phe Asp Gly Ser Lys Thr Asn Tyr Gly Gly Pro Val
    50                  55                  60

Gln Gly Arg Phe Thr Ile Ser Arg Asp Asn Ser Glu Asn Thr Leu Tyr
65                  70                  75                  80
```

```
Leu Gln Met Asn Ser Leu Arg Ala Glu Asp Thr Ala Val Tyr Tyr Cys
                85                  90                  95

Thr Arg Gly Ala Phe Asp Ile Trp Gly Gln Gly Thr Leu Val Thr Val
            100                 105                 110
```

<210> SEQ ID NO 37
<211> LENGTH: 109
<212> TYPE: PRT
<213> ORGANISM: Homo sapiens

<400> SEQUENCE: 37

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Lys Pro Val Phe Gly Gly Gly Thr Lys Leu Thr Val Leu
            100                 105
```

<210> SEQ ID NO 38
<211> LENGTH: 115
<212> TYPE: PRT
<213> ORGANISM: Homo sapiens

<400> SEQUENCE: 38

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Phe Ile Ser Tyr Asp Gly Asn Lys Glu Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Tyr Gly Leu Phe Asp Tyr Trp Gly Gln Gly Thr Leu
            100                 105                 110

Val Thr Val
        115
```

<210> SEQ ID NO 39
<211> LENGTH: 110
<212> TYPE: PRT
<213> ORGANISM: Homo sapiens

<400> SEQUENCE: 39

```
Gln Ser Val Leu Thr Gln Pro Pro Ser Ala Ser Gly Pro Gly Gln
1               5                   10                  15
```

```
Arg Val Thr Ile Ser Cys Ser Gly Asn Ser Ser Asn Ile Gly Ser Asn
            20                  25                  30

Tyr Val Tyr Trp Tyr Gln Gln Leu Pro Gly Thr Ala Pro Lys Leu Leu
            35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Arg Val Phe Gly Gly Arg Thr Lys Leu Thr Val Leu
            100                 105                 110

<210> SEQ ID NO 40
<211> LENGTH: 118
<212> TYPE: PRT
<213> ORGANISM: Homo sapiens

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
            35                  40                  45

Ser Leu Ile Ser Trp Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ser Ile Ser Ala Ala Thr Gly Leu Asp Tyr Trp Gly Gln
            100                 105                 110

Gly Thr Leu Val Thr Val
            115

<210> SEQ ID NO 41
<211> LENGTH: 110
<212> TYPE: PRT
<213> ORGANISM: Homo sapiens

<400> SEQUENCE: 41

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Ser Asn
            20                  25                  30

Thr Val Asn Trp Tyr Gln Gln Leu Pro Gly Thr Val Pro Lys Leu Leu
            35                  40                  45

Ile Tyr Glu Asn Lys Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Thr Lys Leu Thr Val Leu
            100                 105                 110
```

-continued

<210> SEQ ID NO 42
<211> LENGTH: 119
<212> TYPE: PRT
<213> ORGANISM: Homo sapiens

<400> SEQUENCE: 42

Glu Val Gln Leu Leu Glu Ser Gly Gly Gly Leu Val Gln Pro Gly Gly
1               5                   10                  15

Phe Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Arg Arg Ala Ile Ala Val Ala Gly Ala Phe Asp Ile Trp Gly
            100                 105                 110

Gln Gly Thr Leu Val Thr Val
        115

<210> SEQ ID NO 43
<211> LENGTH: 111
<212> TYPE: PRT
<213> ORGANISM: Homo sapiens

<400> SEQUENCE: 43

Gln Ser Val Leu Thr Gln Pro Pro Ser Ala Ser Gly Thr Pro Gly Gln
1               5                   10                  15

Arg Val Thr Ile Ser Cys Ser Gly Ser Ala Ser Asn Ile Gly Ile Asn
            20                  25                  30

Gly Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Gln Val Val Phe Gly Gly Gly Thr Lys Leu Thr Val Leu
            100                 105                 110

<210> SEQ ID NO 44
<211> LENGTH: 118
<212> TYPE: PRT
<213> ORGANISM: Homo sapiens

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Val Pro Gly Lys Gly Leu Glu Trp Val
        35                  40                  45

```
Ser Leu Ile Ser Trp Asp Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Pro Ser Gly Ala Tyr Pro Thr Pro Phe Asp Asn Trp Gly Gln
            100                 105                 110

Gly Thr Leu Val Thr Val
            115

<210> SEQ ID NO 45
<211> LENGTH: 110
<212> TYPE: PRT
<213> ORGANISM: Homo sapiens

<400> SEQUENCE: 45

Gln Ser Val Leu Thr Gln Pro Pro Ser Ala Ser Gly Thr Pro Gly Gln
 1               5                  10                  15

Arg Val Thr Ile Ser Cys Ser Gly Ser Thr Ser Asn Ile Gly Ser Asn
             20                  25                  30

Tyr Val Tyr Trp Tyr Gln Gln Leu Pro Gly Thr Ala Pro Lys Leu Leu
         35                  40                  45

Ile Tyr Asp Asn Asn Lys Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Trp Val Phe Gly Gly Gly Thr Lys Leu Thr Val Leu
            100                 105                 110

<210> SEQ ID NO 46
<211> LENGTH: 114
<212> TYPE: PRT
<213> ORGANISM: Homo sapiens

<400> SEQUENCE: 46

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Ser Gly
             20                  25                  30

Pro Met Ser Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ala Glu Ile Phe Asp Ile Trp Gly Gln Gly Thr Leu Val
            100                 105                 110

Thr Val

<210> SEQ ID NO 47
<211> LENGTH: 110
<212> TYPE: PRT
```

```
<213> ORGANISM: Homo sapiens

<400> SEQUENCE: 47

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Asn Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
                85                  90                  95

Ser Gly Val Val Phe Gly Gly Gly Thr Lys Leu Thr Val Leu
            100                 105                 110

<210> SEQ ID NO 48
<211> LENGTH: 111
<212> TYPE: PRT
<213> ORGANISM: Homo sapiens

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Leu Ile Ser Trp Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Phe Asp Pro Trp Gly Gln Gly Thr Leu Val Thr Val
            100                 105                 110

<210> SEQ ID NO 49
<211> LENGTH: 108
<212> TYPE: PRT
<213> ORGANISM: Homo sapiens

<400> SEQUENCE: 49

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Met Ile Trp Pro Ser Asn Ala
                85                  90                  95
```

-continued

```
Trp Val Phe Gly Gly Arg Thr Lys Leu Thr Val Leu
            100                 105

<210> SEQ ID NO 50
<211> LENGTH: 114
<212> TYPE: PRT
<213> ORGANISM: Homo sapiens

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Ser
            20                  25                  30

Pro Met His Trp Val Arg Gln Ala Pro Gly Lys Gly Leu Glu Trp Val
        35                  40                  45

Ser Gly Val Ser Trp Asn Gly Ser Arg Thr His Tyr Val Asp Ser Val
    50                  55                  60

Lys Arg Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Ala Phe Asp Ile Trp Gly Gln Gly Thr Leu Val
            100                 105                 110

Thr Val

<210> SEQ ID NO 51
<211> LENGTH: 110
<212> TYPE: PRT
<213> ORGANISM: Homo sapiens

<400> SEQUENCE: 51

Gln Ser Val Leu Thr Gln Pro Pro Ser Ala Ser Gly Thr Pro Gly Gln
1               5                   10                  15

Arg Val Thr Ile Ser Cys Ser Gly Thr Thr Ser Ser Ile Gly Ser Asn
            20                  25                  30

Thr Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110

<210> SEQ ID NO 52
<211> LENGTH: 118
<212> TYPE: PRT
<213> ORGANISM: Homo sapiens

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
            35                  40                  45

Ser Gly Val Gly Ser Ser Gly Val Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Ala Thr Ser Ser Thr His Phe Asp Tyr Trp Gly Gln
            100                 105                 110

Gly Thr Leu Val Thr Val
            115
```

<210> SEQ ID NO 53
<211> LENGTH: 110
<212> TYPE: PRT
<213> ORGANISM: Homo sapiens

<400> SEQUENCE: 53

```
Gln Ser Val Leu Thr Gln Pro Pro Ser Ala Ser Gly Thr Pro Gly Gln
1               5                   10                  15

Arg Val Thr Ile Ser Cys Ser Gly Ser Arg Phe Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Arg Asn Glu Asn Arg Pro Ser Gly Val Pro Asp Arg Phe Ser
    50                  55                  60

Gly Ser Lys Ser Gly Ser Ser Ala Ser Leu Ala Ile Ser Gly Leu Arg
65                  70                  75                  80

Ser Glu Asp Glu Ala Asp Tyr Tyr Cys Ala Ala Trp Asp Gly Ser Leu
                85                  90                  95

Ser Ala Trp Val Phe Gly Gly Gly Thr Lys Leu Thr Val Leu
            100                 105                 110
```

<210> SEQ ID NO 54
<211> LENGTH: 116
<212> TYPE: PRT
<213> ORGANISM: Homo sapiens
<220> FEATURE:
<221> NAME/KEY: misc_feature
<222> LOCATION: (103)..(103)
<223> OTHER INFORMATION: Xaa can be any one naturally occurring amino
      acid

<400> SEQUENCE: 54

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Ala Ile Ser Tyr Glu Gly Ser Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Ser Gly Val Tyr Tyr Xaa Gly Met Asp Val Trp Gly Gln Gly Thr
                100                 105                 110

Leu Val Thr Val
        115

<210> SEQ ID NO 55
<211> LENGTH: 110
<212> TYPE: PRT
<213> ORGANISM: Homo sapiens

<400> SEQUENCE: 55

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Asn Ser
            20                  25                  30

His Val Tyr Trp Tyr Gln Leu Pro Gly Thr Ala Pro Lys Leu Leu
        35                  40                  45

Ile Tyr Asn Asp Asn Leu Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ile Gly Trp Met Phe Gly Gly Gly Thr Lys Leu Lys Val Leu
                100                 105                 110

<210> SEQ ID NO 56
<211> LENGTH: 116
<212> TYPE: PRT
<213> ORGANISM: Homo sapiens

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Leu Asn Arg Ala Gly Ala Phe Asp Ile Trp Gly Gln Gly Thr
                100                 105                 110

Leu Val Thr Val
        115

<210> SEQ ID NO 57
<211> LENGTH: 110
<212> TYPE: PRT
<213> ORGANISM: Homo sapiens

<400> SEQUENCE: 57

Gln Ser Val Leu Thr Gln Pro Pro Ser Ala Ser Gly Pro Gly Gln
1               5                   10                  15
```

```
Arg Val Thr Ile Ser Cys Ser Gly Arg Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Lys Asn Asn Gln Arg Pro Ser Gly Val Pro Asp Arg Phe Ser
50                      55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Val Trp Asp Gly Ser Leu
                85                  90                  95

Ser Gly Trp Ala Phe Gly Gly Arg Thr Lys Leu Thr Val Leu
                100                 105                 110

<210> SEQ ID NO 58
<211> LENGTH: 112
<212> TYPE: PRT
<213> ORGANISM: Homo sapiens

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ser Leu Ile Ser Trp Asp Gly Ser Thr Tyr Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Phe Asp Pro Trp Gly Gln Gly Thr Leu Val Thr Val
                100                 105                 110

<210> SEQ ID NO 59
<211> LENGTH: 110
<212> TYPE: PRT
<213> ORGANISM: Homo sapiens

<400> SEQUENCE: 59

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Tyr Val Tyr Trp Tyr Gln Gln Leu Pro Gly Thr Ala Pro Lys Leu Leu
            35                  40                  45

Ile Tyr Asp Asn Asn Lys Arg Pro Ser Gly Val Pro Asp Arg Phe Ser
50                      55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Gly Ser Leu
                85                  90                  95

Asn Gly Pro Val Phe Gly Gly Gly Thr Lys Leu Thr Val Leu
                100                 105                 110

<210> SEQ ID NO 60
<211> LENGTH: 111
```

```
<212> TYPE: PRT
<213> ORGANISM: Homo sapiens

<400> SEQUENCE: 60
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Thr Val Ser Leu Tyr Trp Gly Gln Gly Thr Leu Val Thr Val
            100                 105                 110

```
<210> SEQ ID NO 61
<211> LENGTH: 111
<212> TYPE: PRT
<213> ORGANISM: Homo sapiens

<400> SEQUENCE: 61
```

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Ser Ser
                85                  90                  95

Leu Ser Arg Trp Val Phe Gly Gly Gly Thr Lys Leu Thr Val Leu
            100                 105                 110

```
<210> SEQ ID NO 62
<211> LENGTH: 118
<212> TYPE: PRT
<213> ORGANISM: Homo sapiens

<400> SEQUENCE: 62
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ser Ile Ser Ser Ser Ser Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Gly Gly Gly Gln Gln Leu Gly Ala Phe Asp Ile Trp Gly Gln
            100                 105                 110

Gly Thr Leu Val Thr Val
        115
```

<210> SEQ ID NO 63
<211> LENGTH: 110
<212> TYPE: PRT
<213> ORGANISM: Homo sapiens

<400> SEQUENCE: 63

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Phe Val Thr Trp Tyr Gln Gln Leu Pro Gly Thr Ala Pro Lys Leu Leu
        35                  40                  45

Ile Tyr Gly Asn Asn Asn Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Gly Ser Leu
                85                  90                  95

Ser Gly Trp Val Phe Gly Gly Gly Thr Lys Leu Thr Val Leu
            100                 105                 110
```

<210> SEQ ID NO 64
<211> LENGTH: 117
<212> TYPE: PRT
<213> ORGANISM: Homo sapiens

<400> SEQUENCE: 64

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Ala Phe Thr Gly Pro Asp Ala Phe Asp Ile Trp Gly Gln Gly
            100                 105                 110

Thr Leu Val Thr Val
        115
```

<210> SEQ ID NO 65
<211> LENGTH: 110
<212> TYPE: PRT
<213> ORGANISM: Homo sapiens

<400> SEQUENCE: 65

-continued

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ala Val Asn Trp Tyr Gln Gln Leu Pro Gly Thr Ala Pro Lys Leu Leu
        35                  40                  45

Ile Tyr Thr Asn Thr Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu
            100                 105                 110
```

<210> SEQ ID NO 66
<211> LENGTH: 115
<212> TYPE: PRT
<213> ORGANISM: Homo sapiens

<400> SEQUENCE: 66

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Pro Met Thr Trp Val Arg Gln Ala Pro Gly Lys Gly Leu Glu Trp Val
        35                  40                  45

Ala Val Ile Ser Tyr Asp Ala Ser Gln Thr Tyr Tyr Ala Glu Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Tyr Gly Leu Leu Asp Tyr Trp Gly Gln Gly Thr Leu
            100                 105                 110

Val Thr Val
115
```

<210> SEQ ID NO 67
<211> LENGTH: 109
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any one naturally occurring amino
      acid
<220> FEATURE:
<221> NAME/KEY: misc_feature
<222> LOCATION: (38)..(38)
<223> OTHER INFORMATION: Xaa can be any one naturally occurring amino
      acid

<400> SEQUENCE: 67

```
Gln Ser Val Leu Thr Gln Pro Pro Ser Xaa Ser Gly Pro Gly Gln
1               5                   10                  15

Arg Val Thr Ile Ser Cys Ser Gly Ser Ser Asn Ile Gly Asn Asn
            20                  25                  30

Tyr Val Ser Trp Tyr Xaa Gln Leu Pro Gly Thr Ala Pro Lys Leu Leu
        35                  40                  45
```

Ile Tyr Asp Asn Asn Lys Arg Pro Ser Gly Val Pro Asp Arg Phe Ser
            50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Val Phe Gly Gly Arg Thr Lys Leu Thr Val Leu
            100                 105

<210> SEQ ID NO 68
<211> LENGTH: 112
<212> TYPE: PRT
<213> ORGANISM: Homo sapiens

<400> SEQUENCE: 68

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ser Leu Ile Ser Trp Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ile Gly Ser Trp Phe Asp Pro Trp Gly Gln Gly Thr Leu Val Thr Val
            100                 105                 110

<210> SEQ ID NO 69
<211> LENGTH: 110
<212> TYPE: PRT
<213> ORGANISM: Homo sapiens
<220> FEATURE:
<221> NAME/KEY: misc_feature
<222> LOCATION: (72)..(72)
<223> OTHER INFORMATION: Xaa can be any one naturally occurring amino
      acid
<220> FEATURE:
<221> NAME/KEY: misc_feature
<222> LOCATION: (82)..(82)
<223> OTHER INFORMATION: Xaa can be any one naturally occurring amino
      acid

<400> SEQUENCE: 69

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Asp Asn Asp Arg Arg Pro Leu Gly Val Pro Asp Arg Phe Ser
    50                  55                  60

Gly Ser Lys Ser Gly Thr Ser Xaa Ser Leu Ala Ile Ser Gly Leu Arg
 65                  70                  75                  80

Ser Xaa Asp Glu Ala Asp Tyr Tyr Cys Ala Ala Trp Asp Asp Ser Leu
                 85                  90                  95

Ser Gly Val Val Phe Gly Gly Thr Lys Leu Thr Val Leu
            100                 105                 110

<210> SEQ ID NO 70
<211> LENGTH: 116
<212> TYPE: PRT
<213> ORGANISM: Homo sapiens

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asn Tyr
            20                  25                  30

Gly Met Ser Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Trp Leu Gln Val Asp Ala Phe Asp Leu Trp Gly Gln Gly Thr
            100                 105                 110

Leu Val Thr Val
        115

<210> SEQ ID NO 71
<211> LENGTH: 110
<212> TYPE: PRT
<213> ORGANISM: Homo sapiens

<400> SEQUENCE: 71

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Asn Gly Trp Val Phe Gly Gly Gly Thr Lys Leu Thr Val Leu
            100                 105                 110

<210> SEQ ID NO 72
<211> LENGTH: 112
<212> TYPE: PRT
<213> ORGANISM: Homo sapiens

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

```
Gly Met His Trp Val Arg Gln Ala Pro Gly Lys Gly Leu Glu Trp Val
            35                  40                  45

Ala Leu Ile Ser Phe Asp Gly Ser Lys Thr Asn Tyr Gly Gly Pro Val
 50                  55                  60

Gln Gly Arg Phe Thr Ile Ser Arg Asp Asn Ser Glu Asn Thr Leu Tyr
 65                  70                  75                  80

Leu Gln Met Asn Ser Leu Arg Ala Glu Asp Thr Ala Val Tyr Tyr Cys
                85                  90                  95

Thr Arg Gly Ala Phe Asp Ile Trp Gly Gln Gly Thr Leu Val Thr Val
                100                 105                 110
```

<210> SEQ ID NO 73
<211> LENGTH: 109
<212> TYPE: PRT
<213> ORGANISM: Homo sapiens

<400> SEQUENCE: 73

```
Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
                20                  25                  30

Tyr Val Tyr Trp Tyr Gln Gln Leu Pro Gly Thr Ala Pro Lys Leu Leu
            35                  40                  45

Ile Tyr Asp Asn Asn Lys Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                85                  90                  95

Lys Pro Val Phe Gly Gly Gly Thr Lys Leu Thr Val Leu
                100                 105
```

<210> SEQ ID NO 74
<211> LENGTH: 115
<212> TYPE: PRT
<213> ORGANISM: Homo sapiens

<400> SEQUENCE: 74

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
            35                  40                  45

Ser Leu Ile Ser Trp Asp Gly Arg Thr Ser Tyr Thr Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Leu Ile Gly Asp Asn Trp Gly Gln Gly Thr Leu Val Thr
                100                 105                 110

Val Ser Ser
        115
```

<210> SEQ ID NO 75
<211> LENGTH: 111

<212> TYPE: PRT
<213> ORGANISM: Homo sapiens

<400> SEQUENCE: 75

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Trp Val Phe Gly Gly Gly Thr Lys Leu Thr Val Leu
            100                 105                 110
```

<210> SEQ ID NO 76
<211> LENGTH: 384
<212> TYPE: DNA
<213> ORGANISM: Homo sapiens

<400> SEQUENCE: 76

```
atgaagtcac agacccaggt cttcgtattt ctactgctct gtgtgtctgg tgctcatggg     60
agtattgtga tgacccagac tcccaaattc ctgcttgtat cagcaggaga cagggttacc    120
ataacctgca aggccagtca gggtgtgagt aatgatgtag cttggttcca gcagaagcca    180
gggcagtctc ctaaactgct gatatactct gcatccactc gctacactgg agtccctgat    240
cgcctcactg gcagtggata tgggacggat ttcactttca ccatcaacac tgtgcaggct    300
gaagacctgg cagtttactt ctgtcagcag gattatacct ctccgacgtt cggtggaggc    360
accaagctgg aaatcaaacg ggct                                           384
```

<210> SEQ ID NO 77
<211> LENGTH: 399
<212> TYPE: DNA
<213> ORGANISM: Homo sapiens

<400> SEQUENCE: 77

```
atggactcca ggctcaattt agttttcctt gtccttattt taaaaggtgt ccagtgtgac     60
gtgcagctgg tggagtctgg gggaggcttg gtgcagcctg agggtcccg gaaactctcc     120
tgtgcagcct ctggattcgc tttcagtagt tttggaatgc agtgggttcg tcaggctcca    180
gagaaggggc tggagtgggt cgcatatatt agtagtggca gtagtaccat ctactatgca    240
gacacagtga aggccgatt caccatctcc agagacaatc ccaagaacac cctgttcctg    300
caaatgacca gtctaaggtc tgaggacacg gccatgtatt actgtgtaag atctgggagg    360
gactactggg gtcaaggaac ctcagtcacc gtcagctca                           399
```

<210> SEQ ID NO 78
<211> LENGTH: 387
<212> TYPE: DNA
<213> ORGANISM: Homo sapiens

<400> SEQUENCE: 78

```
atgaggttcc aggttcaggt tctggggctc cttctgctct ggatatcagg tgcccagtgt     60
```
gatgtccaga taacccagtc tccatcttat cttgctgcat ctcctggaga aaccattact    120
cttaattgca gggcaagtaa gaacatttac aaatatttag cctggtatca agaaaaacct    180
gggaaaacta ataaccttct tatctactct ggatccactt tgcattctgg aattccatca    240
aggttcagtg gcagtggatc tggtacagat ttcactctca ccatcagtag cctggatcct    300
gaagattttg caatgtatta ctgtcaacag cataatgatt acccgtacac gttcggaggg    360
gggaccaagc tggagataaa acgggct                                       387

<210> SEQ ID NO 79
<211> LENGTH: 405
<212> TYPE: DNA
<213> ORGANISM: Homo sapiens

<400> SEQUENCE: 79
atgagagtgc tgattctttt gtggctgttc acagcctttc ctggtatcct gtctgatgtg     60
cagcttcagg agtcgggacc tggcctggtg aagccttctc agtctctgtc cctcacctgc    120
actgtcactg gctactcaat caccagtgat tatgcctgga ctggatccg gcagtttcca    180 ggaaacaaac tggagtggat gggctacata agttacagtg gtagtactag ctacaaccca    240
tctctcaaaa gtcgaatctc tatcactcga gacacatcca agaaccagtt cttcctgcag    300
ttgaattctg tgactactga ggacacagcc acatattttt gtgcaagaga ctacggctac    360
gtctttgact actggggcca aggcaccact ctcacagtct cctca                    405

<210> SEQ ID NO 80
<211> LENGTH: 399
<212> TYPE: DNA
<213> ORGANISM: Homo sapiens

<400> SEQUENCE: 80
atggagacag acacactcct gttatgggta ctgctgctct gggttccagg ttccactggt     60
gacattgtgc tgacacagtc tcctgcttcc ttagctgtat ctctggggca gggggccacc    120
atctcatgca gggccagcaa aagtgtcagt acatctggct atacttatat gcactggtac    180
caacagaaac caggacagcc acccaaactc ctcatctatc ttgcatccaa cctagaatct    240
ggggtccctg ccaggttcag tggcagtggg tctgggacag acttcaccct caacatccat    300
cctgtggagg aggaggatgc tgcaacctat tactgtcagc acagtgggga gcttcctccc    360
tcgttcggag gggggaccaa gctggaaata aaacgggct                          399

<210> SEQ ID NO 81
<211> LENGTH: 429
<212> TYPE: DNA
<213> ORGANISM: Homo sapiens

<400> SEQUENCE: 81
atgaacttcg ggctcagctt gattttcctt gccctcattt taaaaggtgt ccagtgtgag     60
gtgcagctgg tggagtctgg gggagactta gtgaagcctg agggtccct gaaactctcc    120 tgtgcagtct ctggattcac tttcagtagc tatggcatgt cttgggttcg ccagactcca    180
gacaagaggc tggagtgggt cgcaaccgtt agtagtggtg gtacttacac ctactatcca    240
gacagtgtga aggggcgatt caccatctcc agagacaatg ccaagaacac cctgtacctg    300
caaatgagca gtctgaagtc tgaggactca gccatgtatt actgtgcaag acatagggga    360
aactactatg ctacttatta ctatgctatg gactactggg gtcaaggaac ctcagtcacc    420

```
gtctcctcg                                                                         429
```

<210> SEQ ID NO 82
<211> LENGTH: 108
<212> TYPE: PRT
<213> ORGANISM: Homo sapiens

<400> SEQUENCE: 82

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Gly Val Ser Asn Asp
            20                  25                  30

Val Ala Trp Phe Gln Gln Lys Pro Gly Gln Ser Pro Lys Leu Leu Ile
        35                  40                  45

Tyr Ser Ala Ser Thr Arg Tyr Thr Gly Val Pro Asp Arg Leu Thr Gly
    50                  55                  60

Ser Gly Tyr Gly Thr Asp Phe Thr Phe Thr Ile Asn Thr Val Gln Ala
65                  70                  75                  80

Glu Asp Leu Ala Val Tyr Phe Cys Gln Gln Asp Tyr Thr Ser Pro Thr
                85                  90                  95

Phe Gly Gly Gly Thr Lys Leu Glu Ile Lys Arg Ala
            100                 105

<210> SEQ ID NO 83
<211> LENGTH: 114
<212> TYPE: PRT
<213> ORGANISM: Homo sapiens

<400> SEQUENCE: 83

Asp Val Gln Leu Val Glu Ser Gly Gly Leu Val Gln Pro Gly Gly
1               5                   10                  15

Ser Arg Lys Leu Ser Cys Ala Ala Ser Gly Phe Ala Phe Ser Ser Phe
            20                  25                  30

Gly Met Gln Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Val Arg Ser Gly Arg Asp Tyr Trp Gly Gln Gly Thr Ser Val Thr Val
            100                 105                 110

Ser Ser

<210> SEQ ID NO 84
<211> LENGTH: 109
<212> TYPE: PRT
<213> ORGANISM: Homo sapiens

<400> SEQUENCE: 84

Asp Val Gln Ile Thr Gln Ser Pro Ser Tyr Leu Ala Ala Ser Pro Gly
1               5                   10                  15

Glu Thr Ile Thr Leu Asn Cys Arg Ala Ser Lys Asn Ile Tyr Lys Tyr
            20                  25                  30

Leu Ala Trp Tyr Gln Glu Lys Pro Gly Lys Thr Asn Asn Leu Leu Ile
        35                  40                  45

```
Tyr Ser Gly Ser Thr Leu His Ser Gly Ile Pro Ser Arg Phe Ser Gly
     50                  55                  60

Ser Gly Ser Gly Thr Asp Phe Thr Leu Thr Ile Ser Ser Leu Asp Pro
 65                  70                  75                  80

Glu Asp Phe Ala Met Tyr Tyr Cys Gln Gln His Asn Asp Tyr Pro Tyr
                 85                  90                  95

Thr Phe Gly Gly Gly Thr Lys Leu Glu Ile Lys Arg Ala
                100                 105
```

<210> SEQ ID NO 85
<211> LENGTH: 117
<212> TYPE: PRT
<213> ORGANISM: Homo sapiens

<400> SEQUENCE: 85

```
Asp Val Gln Leu Gln Glu Ser Gly Pro Gly Leu Val Lys Pro Ser Gln
 1               5                  10                  15

Ser Leu Ser Leu Thr Cys Thr Val Thr Gly Tyr Ser Ile Thr Ser Asp
                 20                  25                  30

Tyr Ala Trp Asn Trp Ile Arg Gln Phe Pro Gly Asn Lys Leu Glu Trp
             35                  40                  45

Met Gly Tyr Ile Ser Tyr Ser Gly Ser Thr Ser Tyr Asn Pro Ser Leu
 50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Phe Cys
                 85                  90                  95

Ala Arg Asp Tyr Gly Tyr Val Phe Asp Tyr Trp Gly Gln Gly Thr Thr
                100                 105                 110

Leu Thr Val Ser Ser
            115
```

<210> SEQ ID NO 86
<211> LENGTH: 113
<212> TYPE: PRT
<213> ORGANISM: Homo sapiens

<400> SEQUENCE: 86

```
Asp Ile Val Leu Thr Gln Ser Pro Ala Ser Leu Ala Val Ser Leu Gly
 1               5                  10                  15

Gln Gly Ala Thr Ile Ser Cys Arg Ala Ser Lys Ser Val Ser Thr Ser
                 20                  25                  30

Gly Tyr Thr Tyr Met His Trp Tyr Gln Gln Lys Pro Gly Gln Pro Pro
             35                  40                  45

Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Gly
                 85                  90                  95

Glu Leu Pro Pro Ser Phe Gly Gly Gly Thr Lys Leu Glu Ile Lys Arg
                100                 105                 110

Ala
```

<210> SEQ ID NO 87
<211> LENGTH: 124
<212> TYPE: PRT

-continued

<213> ORGANISM: Homo sapiens

<400> SEQUENCE: 87

Glu Val Gln Leu Val Glu Ser Gly Gly Asp Leu Val Lys Pro Gly Gly
1               5                   10                  15

Ser Leu Lys Leu Ser Cys Ala Val Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Val Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Ser Ala Met Tyr Tyr Cys
                85                  90                  95

Ala Arg His Arg Gly Asn Tyr Tyr Ala Thr Tyr Tyr Tyr Ala Met Asp
            100                 105                 110

Tyr Trp Gly Gln Gly Thr Ser Val Thr Val Ser Ser
        115                 120

<210> SEQ ID NO 88
<211> LENGTH: 111
<212> TYPE: PRT
<213> ORGANISM: Homo sapiens

<400> SEQUENCE: 88

Asp Ile Val Leu Thr Gln Ser Pro Asp Ser Leu Ala Val Ser Leu Gly
1               5                   10                  15

Glu Arg Ala Thr Ile Asn Cys Lys Ala Ser Lys Ser Val Ser Thr Ser
            20                  25                  30

Gly Tyr Thr Tyr Met His Trp Tyr Gln Gln Lys Pro Gly Gln Pro Pro
        35                  40                  45

Lys Leu Leu Ile Tyr Leu Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Pro Val Gln Ala Glu Asp Val Ala Thr Tyr Tyr Cys Gln His Ser Gly
                85                  90                  95

Glu Leu Pro Pro Ser Phe Gly Gln Gly Thr Lys Leu Glu Ile Lys
            100                 105                 110

<210> SEQ ID NO 89
<211> LENGTH: 124
<212> TYPE: PRT
<213> ORGANISM: Homo sapiens

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Gly Met Ser Trp Val Arg Gln Ala Pro Gly Lys Arg Leu Glu Trp Val
        35                  40                  45

Ala Thr Val Ser Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Met Tyr Tyr Cys
            85                  90                  95

Ala Arg His Arg Gly Asn Tyr Tyr Ala Thr Tyr Tyr Tyr Ala Met Asp
            100                 105                 110

Tyr Trp Gly Gln Gly Thr Leu Val Thr Val Ser Ser
        115                 120
```

<210> SEQ ID NO 90
<211> LENGTH: 124
<212> TYPE: PRT
<213> ORGANISM: Homo sapiens

<400> SEQUENCE: 90

```
Glu Val Gln Leu Val Glu Ser Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Gly Met Ser Trp Val Arg Gln Ala Pro Gly Lys Gly Leu Glu Trp Val
            35                  40                  45

Ala Thr Val Ser Ser Gly Gly Thr Tyr Thr Tyr Tyr Pro Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg His Arg Gly Asn Tyr Tyr Ala Thr Tyr Tyr Tyr Ala Met Asp
            100                 105                 110

Tyr Trp Gly Gln Gly Thr Leu Val Thr Val Ser Ser
        115                 120
```

<210> SEQ ID NO 91
<211> LENGTH: 107
<212> TYPE: PRT
<213> ORGANISM: Homo sapiens

<400> SEQUENCE: 91

```
Asp Val Gln Ile Thr Gln Ser Pro Ser Ser Leu Ser Ala Ser Pro Gly
1               5                   10                  15

Asp Arg Ile Thr Leu Thr Cys Arg Ala Ser Lys Asn Ile Tyr Lys Tyr
            20                  25                  30

Leu Ala Trp Tyr Gln Glu Lys Pro Gly Lys Thr Asn Asn Leu Leu Ile
            35                  40                  45

Tyr Ser Gly Ser Thr Leu His Ser Gly Ile Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Met Tyr Tyr Cys Gln Gln His Asn Asp Tyr Pro Tyr
            85                  90                  95

Thr Phe Gly Gln Gly Thr Lys Leu Glu Ile Lys
            100                 105
```

<210> SEQ ID NO 92
<211> LENGTH: 107
<212> TYPE: PRT
<213> ORGANISM: Homo sapiens

<400> SEQUENCE: 92

-continued

Asp Val Gln Ile Thr Gln Ser Pro Ser Ser Leu Ser Ala Ser Pro Gly
1               5                   10                  15

Asp Arg Ile Thr Leu Thr Cys Arg Ala Ser Lys Asn Ile Tyr Lys Tyr
            20                  25                  30

Leu Ala Trp Tyr Gln Glu Lys Pro Gly Lys Ala Asn Lys Leu Leu Ile
        35                  40                  45

Tyr Ser Gly Ser Thr Leu His Ser Gly Ile Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Met Tyr Tyr Cys Gln Gln His Asn Asp Tyr Pro Tyr
                85                  90                  95

Thr Phe Gly Gln Gly Thr Lys Leu Glu Ile Lys
            100                 105

<210> SEQ ID NO 93
<211> LENGTH: 117
<212> TYPE: PRT
<213> ORGANISM: Homo sapiens

<400> SEQUENCE: 93

Asp Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Lys Lys Leu Glu Trp
        35                  40                  45

Met Gly Tyr Ile Ser Tyr Ser Gly Ser Thr Tyr Asn Pro Ser Leu
50                  55                  60

Lys Ser Arg Ile Thr Ile Ser Arg Asp Thr Ser Lys Asn Gln Phe Ser
65                  70                  75                  80

Leu Gln Leu Asn Ser Val Thr Ala Ala Asp Thr Ala Thr Tyr Phe Cys
                85                  90                  95

Ala Arg Asp Tyr Gly Tyr Val Phe Asp Tyr Trp Gly Gln Gly Thr Thr
            100                 105                 110

Leu Thr Val Ser Ser
            115

<210> SEQ ID NO 94
<211> LENGTH: 117
<212> TYPE: PRT
<213> ORGANISM: Homo sapiens

<400> SEQUENCE: 94

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Phe Pro Gly Lys Gly Leu Glu Trp
        35                  40                  45

Met Gly Tyr Ile Ser Tyr Ser Gly Ser Thr Tyr Asn Pro Ser Leu
50                  55                  60

Lys Ser Arg Ile Thr Ile Ser Arg Asp Thr Ser Lys Asn Gln Phe Ser
65                  70                  75                  80

Leu Gln Leu Asn Ser Val Thr Ala Ala Asp Thr Ala Val Tyr Phe Cys
                85                  90                  95

Ala Arg Asp Tyr Gly Tyr Val Phe Asp Tyr Trp Gly Gln Gly Thr Thr
            100                 105                 110

Leu Thr Val Ser Ser
        115

<210> SEQ ID NO 95
<211> LENGTH: 106
<212> TYPE: PRT
<213> ORGANISM: Homo sapiens

<400> SEQUENCE: 95

Asp Ile Val Met Thr Gln Ser Pro Asp Ser Leu Ala Val Ser Ala Gly
1               5                   10                  15

Glu Arg Val Thr Ile Asn Cys Lys Ala Ser Gln Gly Val Ser Asn Asp
            20                  25                  30

Val Ala Trp Phe Gln Gln Lys Pro Gly Gln Ser Pro Lys Leu Leu Ile
        35                  40                  45

Tyr Ser Ala Ser Thr Arg Tyr Thr Gly Val Pro Asp Arg Leu Ser Gly
    50                  55                  60

Ser Gly Ser Gly Thr Asp Phe Thr Phe Thr Ile Ser Ser Val Gln Ala
65                  70                  75                  80

Glu Asp Val Ala Val Tyr Phe Cys Gln Gln Asp Tyr Thr Ser Pro Thr
                85                  90                  95

Phe Gly Gln Gly Thr Lys Leu Glu Ile Lys
            100                 105

<210> SEQ ID NO 96
<211> LENGTH: 106
<212> TYPE: PRT
<213> ORGANISM: Homo sapiens

<400> SEQUENCE: 96

Asp Ile Val Met Thr Gln Ser Pro Asp Ser Leu Ala Val Ser Leu Gly
1               5                   10                  15

Glu Arg Val Thr Ile Asn Cys Lys Ala Ser Gln Gly Val Ser Asn Asp
            20                  25                  30

Val Ala Trp Phe Gln Gln Lys Pro Gly Gln Ser Pro Lys Leu Leu Ile
        35                  40                  45

Tyr Ser Ala Ser Thr Arg Glu Ser Gly Val Pro Asp Arg Leu Ser Gly
    50                  55                  60

Ser Gly Ser Gly Thr Asp Phe Thr Phe Thr Ile Ser Ser Val Gln Ala
65                  70                  75                  80

Glu Asp Val Ala Val Tyr Phe Cys Gln Gln Asp Tyr Thr Ser Pro Thr
                85                  90                  95

Phe Gly Gln Gly Thr Lys Leu Glu Ile Lys
            100                 105

<210> SEQ ID NO 97
<211> LENGTH: 114
<212> TYPE: PRT
<213> ORGANISM: Homo sapiens

<400> SEQUENCE: 97

Asp Val Gln Leu Val Glu Ser Gly Gly Gly Leu Val Gln Pro Gly Gly
1               5                   10                  15

Ser Arg Arg Leu Ser Cys Ala Ala Ser Gly Phe Ala Phe Ser Ser Phe
            20                  25                  30

Gly Met Gln Trp Val Arg Gln Ala Pro Gly Lys Gly Leu Glu Trp Val
         35                  40                  45

Ala Tyr Ile Ser Ser Gly Ser Ser Thr Ile Tyr Tyr Ala Asp Thr Val
 50                  55                  60

Lys Gly Arg Phe Thr Ile Ser Arg Asp Asn Pro Lys Asn Thr Leu Tyr
 65                  70                  75                  80

Leu Gln Met Asn Ser Leu Arg Ala Glu Asp Thr Ala Met Tyr Tyr Cys
                 85                  90                  95

Val Arg Ser Gly Arg Asp Tyr Trp Gly Gln Gly Thr Leu Val Thr Val
             100                 105                 110

Ser Ser

<210> SEQ ID NO 98
<211> LENGTH: 114
<212> TYPE: PRT
<213> ORGANISM: Homo sapiens

<400> SEQUENCE: 98

Glu Val Gln Leu Val Glu Ser Gly Gly Gly Leu Val Gln Pro Gly Gly
 1               5                  10                  15

Ser Arg Arg Leu Ser Cys Ala Ala Ser Gly Phe Ala Phe Ser Ser Phe
             20                  25                  30

Gly Met Gln Trp Val Arg Gln Ala Pro Gly Lys Gly Leu Glu Trp Val
         35                  40                  45

Ala Tyr Ile Ser Ser Gly Ser Ser Thr Ile Tyr Tyr Ala Asp Ser Val
 50                  55                  60

Lys Gly Arg Phe Thr Ile Ser Arg Asp Asn Pro Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Arg Ser Gly Arg Asp Tyr Trp Gly Gln Gly Thr Leu Val Thr Val
             100                 105                 110

Ser Ser

<210> SEQ ID NO 99
<211> LENGTH: 15
<212> TYPE: PRT
<213> ORGANISM: Artificial Sequence
<220> FEATURE:
<223> OTHER INFORMATION: Hypothetical Polypeptide

<400> SEQUENCE: 99

Ala Lys Lys Leu Val His Thr Pro Tyr Ser Phe Lys Glu Asp Phe
 1               5                  10                  15

<210> SEQ ID NO 100
<211> LENGTH: 15
<212> TYPE: PRT
<213> ORGANISM: Artificial Sequence
<220> FEATURE:
<223> OTHER INFORMATION: Hypothetical Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)

```
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 100

Ala Lys Xaa Leu Val Xaa Thr Pro Xaa Ser Phe Xaa Glu Asp Xaa
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Hypothetical Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 101

Ala Tyr Xaa Leu Tyr Xaa Thr Tyr Xaa Ser Tyr Xaa Glu Tyr Xaa
1               5                   10                  15

<210> SEQ ID NO 102
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 102

Cys Tyr Gly Gly Arg Gly Asp Thr Pro
1               5

<210> SEQ ID NO 103
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 103

Glu Leu Leu Gly Gly Pro
1               5
```